United States Patent

Shima

(10) Patent No.: US 8,178,246 B2
(45) Date of Patent: May 15, 2012

(54) NONAQUEOUS ELECTROLYTE SOLUTION, NONAQUEOUS ELECTROLYTE SECONDARY CELL, AND CARBONATE COMPOUNDS

(75) Inventor: Noriko Shima, Inashiki-gun (JP)

(73) Assignee: Mitsubishi Chemical Corporation, Tokyo (JP)

( * ) Notice: Subject to any disclaimer, the term of this patent is extended or adjusted under 35 U.S.C. 154(b) by 1120 days.

(21) Appl. No.: 11/917,017

(22) PCT Filed: Jun. 9, 2006

(86) PCT No.: PCT/JP2006/311646
§ 371 (c)(1),
(2), (4) Date: Dec. 10, 2007

(87) PCT Pub. No.: WO2006/132372
PCT Pub. Date: Dec. 14, 2006

(65) Prior Publication Data
US 2009/0253048 A1     Oct. 8, 2009

(30) Foreign Application Priority Data

| Jun. 10, 2005 | (JP) | 2005-170910 |
| Jun. 10, 2005 | (JP) | 2005 170911 |
| Jun. 10, 2005 | (JP) | 2005-170912 |
| Jun. 10, 2005 | (JP) | 2005-170913 |
| Jun. 29, 2005 | (JP) | 2005-190351 |

(51) Int. Cl.
*H01M 6/16* (2006.01)

(52) U.S. Cl. ........ 429/342; 429/199; 429/200; 429/330; 429/332; 429/331; 252/62.2

(58) Field of Classification Search .............. 429/342, 429/199, 200, 330, 332, 331; 252/62.2
See application file for complete search history.

(56) References Cited

U.S. PATENT DOCUMENTS

| 5,633,099 A | 5/1997 | Yokoyama et al. |
| 5,659,062 A | 8/1997 | Yokoyama et al. |
| 5,773,165 A | 6/1998 | Sugeno |

(Continued)

FOREIGN PATENT DOCUMENTS

EP     0 482 287 A1     4/1992

(Continued)

OTHER PUBLICATIONS

Koh et al. "Synthesis and electrochemical properties of the fluorine containing polymer electrolytes", Polymer Preprints (American Chemical Society, Division of Polymer Chemistry) (2005), 46 (2), 650.*

(Continued)

*Primary Examiner* — Laura Weiner
(74) *Attorney, Agent, or Firm* — Oblon, Spivak, McClelland, Maier & Neustadt, L.L.P.

(57) ABSTRACT

The present invention provides a nonaqueous electrolytic solution which can give excellent cycle characteristics. The nonaqueous electrolytic solution contains a linear carbonate represented by the formula (1):

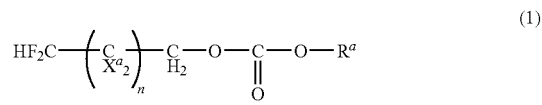

wherein, in the formula (1), $X^a$ represents each independently hydrogen or any group; $R^a$ represents optionally substituted alkyl; and n represents an integer of zero or more.

12 Claims, 8 Drawing Sheets

U.S. PATENT DOCUMENTS

| | | | |
|---|---|---|---|
| 5,847,188 | A | 12/1998 | Yokoyama et al. |
| 2001/0019800 | A1 | 9/2001 | Herreyre et al. |
| 2004/0013946 | A1 | 1/2004 | Abe et al. |
| 2006/0154149 | A1 | 7/2006 | Arai et al. |

FOREIGN PATENT DOCUMENTS

| | | |
|---|---|---|
| EP | 0 548 449 A1 | 6/1993 |
| EP | 0 599 534 A1 | 6/1994 |
| EP | 0 766 332 A1 | 4/1997 |
| EP | 1 009 057 A1 | 6/2000 |
| EP | 1 022 799 A2 | 7/2000 |
| EP | 1 806 806 A1 | 7/2007 |
| JP | 61 64082 | 4/1986 |
| JP | 1 311054 | 12/1989 |
| JP | 7 6786 | 1/1995 |
| JP | 8 45545 | 2/1996 |
| JP | 8-162152 | 6/1996 |
| JP | 9-63644 | 3/1997 |
| JP | 9 251861 | 9/1997 |
| JP | 10 189046 | 7/1998 |
| JP | 10 233345 | 9/1998 |
| JP | 11 176470 | 7/1999 |
| JP | 11 195429 | 7/1999 |
| JP | 2000 40526 | 2/2000 |
| JP | 2000 195544 | 7/2000 |
| JP | 2000188128 (A) | 7/2000 |
| JP | 2003 267931 | 9/2003 |
| JP | 2003 308838 | 10/2003 |
| JP | 2004-14134 | 1/2004 |
| JP | 2004 71459 | 3/2004 |
| JP | 2004 87284 | 3/2004 |
| JP | 2005 47875 | 2/2005 |
| JP | 2005-108724 | 4/2005 |
| JP | 2006 86058 | 3/2006 |
| JP | 2006 139951 | 6/2006 |
| JP | 2006 164867 | 6/2006 |
| KR | 10-2005-0022044 | 3/2005 |
| KR | 10-2005-0040974 | 5/2005 |

OTHER PUBLICATIONS

U.S. Appl. No. 12/677,075, filed Mar. 8, 2010, Ohashi, et al.
European Office Action issued May 23, 2011, in Patent Application No. 06 766 558.8.
Partial European Search Report issued May 23, 2011, in Patent Application No. 11156962.0.
Office Action issued Jun. 27, 2011, in Korean Patent Application No. 2010-7010692 (with English translation).
Notice of Reasons for Rejection issued Feb. 14, 2012, in Japanese Patent Application No. 2006-161355, filed Jun. 9, 2006 (with English-language Translation).

* cited by examiner

NONAQUEOUS ELECTROLYTE SOLUTION, NONAQUEOUS ELECTROLYTE SECONDARY CELL, AND CARBONATE COMPOUNDS

TECHNICAL FIELD

The present invention relates to nonaqueous electrolytic solutions, secondary cells containing the nonaqueous electrolytic solutions, and fluorine-containing carbonate compounds.

BACKGROUND ART

In recent years, size and weight reduction of electrical appliances has propelled the development of lithium secondary cells with high energy density. Further improvements in cell property have been required with extension of the application fields of such secondary cells.

Under such circumstances, secondary cells containing metallic lithium as the negative electrode, have intensively studied as candidates capable of achieving high capacities. However, during repeated charge and discharge cycles, metallic lithium grows into a dendritic crystal. When the dendritic crystal reaches the positive electrode, short circuiting occurs in the cell. This is the most serious obstacle inputting lithium secondary cells with metallic lithium negative electrodes to practical use.

There have also been provided nonaqueous electrolyte secondary cells containing carbonous materials as negative electrodes, which are capable of occluding and discharging lithium, such as cokes, artificial graphite, or natural graphite, in place of metallic lithium. Such secondary cells can exhibit improved service life and safety since lithium does not grow into the dendritic crystal. In particular, nonaqueous electrolyte secondary cells made from graphite-based carbonous materials, such as artificial graphite and natural graphite, have attracted attention as ones capable of meeting the need for high capacities.

Further, negative-electrode active materials made from alloys such as, for example, silicon (Si), tin (Sn), and lead (Pb) have lately been proposed in order to achieve higher capacities (see, for example, Patent Documents 1 and 2).

Furthermore, electrolytic solutions containing different compounds in addition to electrolytes and main solvents have been proposed in order to enhance properties of nonaqueous electrolyte secondary cells, such as load, cycle, storage, and low-temperature characteristics.

For example, electrolytic solutions containing carbonate derivatives having unsaturated bonds have been provided, such as ones containing certain amounts of vinylene carbonate and its derivatives in order to inhibit decomposition of the electrolytic solutions for nonaqueous electrolyte secondary cells including graphite negative electrodes (see, for example, Patent Document 3), and ones containing certain amounts of ethylene carbonate derivatives having a non-conjugated, unsaturated bond at the side chain thereof (see, for example, Patent Document 4).

For electrolytic solutions containing such compounds, the compounds are reductively decomposed on the surfaces of the negative electrodes to form films thereon, and the films inhibit extra decomposition of the electrolytic solutions. Electrolytic solutions containing halogen-containing carbonates have also been proposed (see, for example, Patent Document 5).

Patent Document 6 describes that an electrolytic solutions containing a single solvent, i.e., fluoromethyl ethylene carbonate (4-(monofluoromethyl)-1,3-dioxolan-2-one) in combination with various PF6 and $BF_4$ salts, is excellent in oxidation resistance compared to propylene carbonate or trifluoropropylene carbonate, and thus is useful as an electrolytic solution for a variety of devices. This document also describes that lithium secondary cells containing the electrolytic solution exhibit excellent cycle characteristics and that electric double-layer capacitors containing the electrolytic solution excel in continuous application characteristics at elevated temperatures.

Patent Document 7 describes that electrolytic solutions which contain 60% by volume or more of fluoromethyl ethylene carbonate in their solvents, or difluoromethyl ethylene carbonate and contain $(C_2H_5)_4NBF_4$ or $(C_2H_5)_4NPF_6$ as a supporting electrolyte are excellent in oxidation resistance, and thus is useful as electrolytic solutions for electric double-layer capacitors.

Linear carbonate compounds have generally been used as materials for polycarbonates, and as materials and diluent solvents for medicines and agrichemicals. These have also been used in a broad range of applications, including electrolyte solvents and solid electrolytes for energy storage devices such as Li cells, electrolytic capacitors, and electric double-layer capacitors; and electrode compositions (see, for example, Patent Documents 8 and 9).

For currently used carbonate compounds, further improved performances and added functionalities are still needed because of improvements in synthetic and purification processes or development of advanced processes in the fine chemical field; technological innovation in the fields of agrichemicals and fertilizers; and needs for highly functionalized semiconductors and energy devices subsequent to the downsizing and densifying in the field of electrical and electronic equipment.

[Patent Document 1] Japanese Patent Application Laid-open No. HEI 11-176470

[Patent Document 2] Japanese Patent Application Laid-open No. 2004-87284

[Patent Document 3] Japanese Patent Application Laid-open No. HEI 8-45545

[Patent Document 4] Japanese Patent Application Laid-open No. 2000-40526

[Patent Document 5] Japanese Patent Application Laid-open No. HEI 11-195429

[Patent Document 6] Japanese Patent Application Laid-open No. HEI 9-251861

[Patent Document 7] Japanese Patent Application Laid-open No. HEI 10-233345

[Patent Document 8] Japanese Patent Application Laid-open No. HEI 1-311054

[Patent Document 9] Japanese Patent Application Laid-open No. SHO 61-64082

DISCLOSURE OF INVENTION

Problems to be Solved by the Invention

A further improvement in cycle characteristics is required for technologies on nonaqueous electrolytic solutions.

The present invention has been made in consideration of the problems, and a first object thereof is to provide a non-aqueous electrolytic solution and a secondary cell containing the nonaqueous electrolytic solution which can give more excellent cycle characteristics.

As described above, the conventional linear carbonate compounds have many excellent characteristics. However, a novel linear carbonate compound with a higher boiling point, dielectric constant, and electrochemical stability is needed so as to impart higher performances and functionalities to the conventional compounds and thereby to enhance the added value of the compounds.

The present invention has been made in consideration of the need, and a second object thereof is to provide a novel carbonate compound not yet found.

Means for Solving the Problem

As a result of extensive study to solve such problems, the inventors have discovered the following fact in consideration of the first object and accomplished the present invention: A nonaqueous electrolytic solution containing at least any one of a linear carbonate represented by the formula (1), a compound represented by the formula (2), and a compound represented by the formula (3) can be used for a nonaqueous electrolyte secondary cell in order to achieve much more excellent effects than those of conventional improvements.

As a result of the extensive study to solve such problems, the inventors have also accomplished the present invention under the following investigation in consideration of the second object:

A fluorine atom, in general, has a van der Waals' radius close to that of a hydrogen atom, and also a relatively small covalent radius. Therefore, hydrogen atoms attached to carbon atoms in an organic compound can be readily substituted by fluorine atoms due to such steric configuration.

The bonding electron pair in the carbon-fluorine bond is largely attracted to the fluorine atom having high electronegativity. Therefore, organic fluorine compounds have unique properties which are significantly different from fluorine-free organic compounds. In particular, organic fluorine compounds of which hydrogen atoms attached to the carbon atoms are partially substituted by fluorine atoms may enhance the originally incompatible properties, for example, increased boiling points, decreased viscosities, increased polarities, and increased lipophilicities compared to similar fluorine-free organic compounds. Besides, organic fluorine compounds can also be expected to improve electrical or chemical resistance to oxidation.

When fluorine atoms are introduced to organic compounds in a sterically asymmetric manner, decreased melting points and further decreased viscosities can also be expected because of the steric asymmetry and the symmetry of electron conformation, like when hydrogen is substituted by substituents other than fluorine.

In consideration of general properties of these organic fluorine compounds, introduction of fluorine atoms to linear carbonate compounds will allow improvements in properties of the compounds, for example, increased boiling point, increased dielectric constant, and enhanced electrochemical stability due to enhanced oxidation resistance.

As a result of extensive study to solve such problems in consideration of the above mentioned findings, the inventors have synthesized various linear carbonate compounds each having a 2,2-difluoroethyl group and have accomplished the present invention.

That is, a nonaqueous electrolytic solution in accordance with a first aspect of the present invention comprises a linear carbonate of the following formula (1):

[Chemical Formula 1]

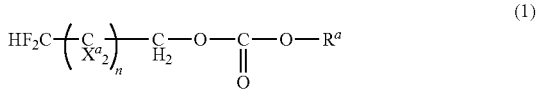

(1)

wherein $X^a$ represents each independently hydrogen or any group; $R^a$ represents optionally substituted alkyl; and n represents an integer of zero or more.

In this case, in the formula (1), the group $R^a$ is preferably different from:

[Chemical Formula 2]

In the nonaqueous electrolytic solution in accordance with the first aspect of the present invention, the linear carbonate is preferably bis(2,2-difluoroethyl)carbonate.

In addition, in the formula (1), n is preferably an integer of from 0 to 7.

A nonaqueous electrolytic solution in accordance with a second aspect of the present invention comprises 0.01% by weight to 10% by weight of a compound of the following formula (2) in a nonaqueous solvent:

[Chemical Formula 3]

(2)

wherein $X^1$ represents oxygen, sulfur, $CD^1D^2$, or $NE^1$, wherein $D^1$ and $D^2$ represent each independently hydrogen, or any group capable of being attached to carbon, and $E^1$ represents hydrogen, or a group capable of being attached to nitrogen;

$X^2$ represents oxygen, sulfur, or $NE^1$;

$Z^1$ and $Z^2$ represent each independently hydrogen, or a group capable of being attached to carbon, with the proviso that at least one of $Z^1$, $Z^2$, $D^1$, $D^2$, and $E^1$ represents alkyl in which both at least one hydrogen atom and at least one fluorine atom are attached to at least one terminal carbon; and m represents a natural number.

In this case, m in the formula (2) preferably represents two or three.

Preferably, $Z^1$, $Z^2$, $D^1$, $D^2$ and $E^1$ in the formula (2) represent each independently any of hydrogen, fluorine, and unsubstituted alkyl or fluorine-substituted alkyl.

Preferably, in the second nonaqueous electrolytic solution of the present invention, the "alkyl in which both at least one hydrogen atom and at least one fluorine atom are attached to at least one terminal carbon" is substituted by fluorine alone.

A nonaqueous electrolytic solution in accordance with a third aspect of the present invention comprises a compound of the following formula (3) in a nonaqueous solvent:

[Chemical Formula 4]

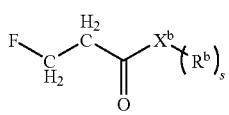

(3)

wherein $X^b$ represents oxygen or nitrogen; $R^b$ represents hydrogen, or substituted or unsubstituted alkyl, and s is one when $X^b$ represents oxygen or two when $X^b$ represents nitrogen.

In this case, in the formula (3), $R^b$ is preferably unsubstituted alkyl or alkyl substituted by fluorine alone.

Preferably, in the nonaqueous electrolytic solution in accordance with the third aspect of the present invention, the concentration of the compound in the nonaqueous electrolytic solution is 0.01% by weight to 10% by weight.

Preferably, the nonaqueous electrolytic solution of each of the first, second, and third aspects of the present invention further comprises a carbonate having at least one of an unsaturated bond and a halogen atom (hereinafter referred to as a "predetermined carbonate"), with the proviso that carbonates which also fall into the definition of the linear carbonates of the formula (1) are excluded from the predetermined carbonates when they are contained in the nonaqueous electrolytic solution in accordance with the first aspect of the present invention, and that carbonates which also fall into the definition of the linear carbonates of the formula (2) are also excluded from the predetermined carbonates when the predetermined carbonates are contained in the nonaqueous electrolytic solution in accordance with the second aspect of the present invention.

Preferably, the concentration of the predetermined carbonate in the nonaqueous electrolytic solution is 0.01% by weight to 70% by weight.

Preferably, the predetermined carbonates are at least one carbonate selected from the group consisting of vinylene carbonate, vinyl ethylene carbonate, fluoroethylene carbonate, difluoroethylene carbonate, and derivatives thereof.

Preferably, the nonaqueous electrolytic solution of each of the first, second, and third aspects of the present invention comprises ethylene carbonate and/or propylene carbonate.

Preferably, the nonaqueous electrolytic solution of the first, second, and third aspects of the present invention comprises at least one selected from the group consisting of dimethyl carbonate, ethyl methyl carbonate, diethyl carbonate, methyl n-propyl carbonate, ethyl n-propyl carbonate, and di-n-propyl carbonate.

A nonaqueous electrolyte secondary cell of the present invention comprises a negative electrode and a positive electrode capable of occluding and discharging lithium ions, and any of the nonaqueous electrolytic solutions of the first, second, and third aspects of the present invention.

A carbonate compound of the present invention is represented by the following formula (4):

[Chemical Formula 5]

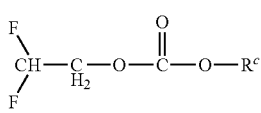

(4)

wherein $R^c$ represents linear unsubstituted alkyl having one to four carbon atoms.

That is, the carbonate compound of the present invention is selected from the group consisting of 2,2-difluoroethyl methyl carbonate, 2,2-difluoroethyl ethyl carbonate, 2,2-difluoroethyl n-propyl carbonate, and n-butyl 2,2-difluoroethyl carbonate.

ADVANTAGES OF THE INVENTION

When contained in a nonaqueous electrolyte secondary cell, the nonaqueous electrolytic solution in accordance with the first aspect of the present invention can give superior cycle characteristics to the conventional one.

The nonaqueous electrolyte secondary cell of the first aspect of the present invention can also exhibit superior cycle characteristics to the conventional one.

Furthermore, when contained in a nonaqueous electrolyte secondary cell, the nonaqueous electrolytic solution in accordance with the second aspect of the present invention can give high capacities and excellent charge and discharge cycle characteristics over a long period.

The nonaqueous electrolyte secondary cell in accordance with the second aspect of the present invention can also exhibit high capacities and excellent charge and discharge cycle characteristics over a long period.

Furthermore, when contained in a nonaqueous electrolyte secondary cell, the nonaqueous electrolytic solution in accordance with the third aspect of the present invention can give excellent charge and discharge cycle characteristics.

The nonaqueous electrolyte secondary cell in accordance with the third aspect of the present invention can exhibit excellent charge and discharge cycle characteristics.

According to the present invention, a novel carbonate compound is provided. The carbonate compound can be inferred to have advantages such as increased boiling point, increased dielectric constant, and enhanced electrochemical stability due to enhanced oxidation resistance.

BEST MODE FOR CARRYING OUT THE INVENTION

Figure 1:
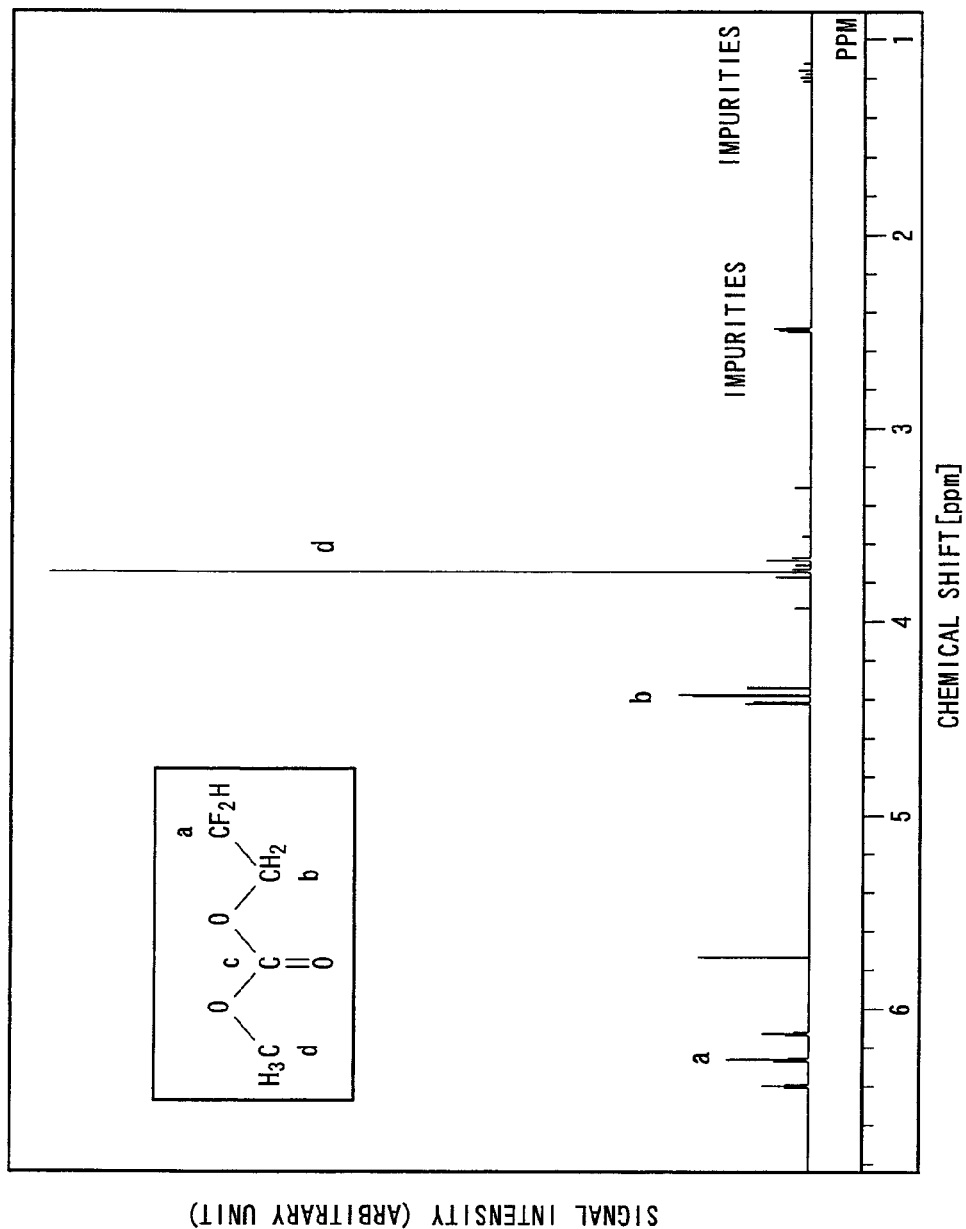
FIG. 1 shows a $^1$H NMR spectrum of a product prepared according to Example IV-1 of the present invention.

The present invention will now be described in detail by reference to preferred embodiments; however, the following description on elements of the invention is only for illustration of (representative) embodiments of the invention, and any variations of the embodiments can be modified unless departing from the spirit of the invention.

[I. Nonaqueous Electrolytic Solution of First Aspect]

The nonaqueous electrolytic solution in accordance with the first aspect of the present invention comprises at least one linear carbonate represented by the following formula (1) (hereinafter referred to as a "particular linear carbonate"):

[Chemical Formula 6]

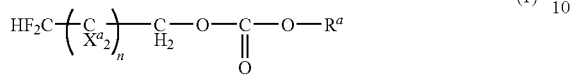

(1)

wherein $X^a$ represents each independently hydrogen or any group; $R^a$ represents optionally substituted alkyl; and n represents an integer of zero or more. The particular linear carbonate can be contained as a nonaqueous solvent in the nonaqueous electrolytic solution in accordance with the first aspect of the present invention. Alternatively, a suitable separate nonaqueous solvent may be contained in the nonaqueous electrolytic solution in accordance with the first aspect of the present invention. The nonaqueous electrolytic solution in accordance with the first aspect of the present invention typically contains an electrolyte, and may optionally contain a predetermined carbonate and any additive.

[I-1. Particular Linear Carbonate]

The particular linear carbonate contained in the nonaqueous electrolytic solution in accordance with the first aspect of the present invention is represented by the formula (1).

$X^a$ in the formula (1) represents hydrogen or any group, wherein $X^a$s in the formula (1) may be the same or different.

$X^a$ may be any group that does not significantly impair the advantages of the present invention. Specific examples of the group include halogens such as fluorine (fluoro), chlorine (chloro), bromine (bromo), and iodine (iodo); linear alkyls such as methyl, ethyl, n-propyl, and i-propyl; cycloalkyls such as cyclohexyl; and aryls such as phenyl and naphthyl. Any hydrogen in the alkyl, cycloalkyl, and aryl groups may be substituted by halogen.

In consideration of the stability as an organic substance of the particular linear carbonate, and the stability of a protective layer formed from the carbonate in use for a nonaqueous electrolyte secondary cell, $X^a$ preferably represents hydrogen or fluorine.

In the above formula (1), n represents any integer of zero or more. Since the particular linear carbonate represented by the formula (1) having a significantly high molecular weight may not exhibit advantages comparable to the amount of the carbonate used, n represents usually seven or less, preferably four or less, and more preferably three or less.

$R^a$ in the formula (1) represents optionally substituted alkyl.

Unless significantly impairing the advantages of the present invention, the carbon number of $R^a$ may also be any number. Since the particular linear carbonate represented by the formula (1) having a significantly high molecular weight may not exhibit effects comparable to the amount of the carbonate used, the number is usually ten or less, preferably five or less, and more preferably three or less.

In consideration of the stability as an organic substance of the particular linear carbonate, and a stability of protective layer formed from the carbonate in use for a nonaqueous electrolyte secondary cell, $R^a$ preferably represents non-branched alkyl, and unsubstituted alkyl or alkyl substituted by fluorine alone.

Specific examples of $R^a$ include methyl, fluoromethyl, ethyl, 2-fluoroethyl, 2,2-difluoroethyl, 2,2,2-trifluoroethyl, n-propyl, 3-fluoro-n-propyl, 3,3-difluoro-n-propyl, 3,3,3-trifluoro-n-propyl, i-propyl, and 1,1,1,3,3,3-hexafluoro-i-propyl.

Among them, methyl, ethyl, 2-fluoroethyl, 2,2-difluoroethyl, 2,2,2-trifluoroethyl, n-propyl, 3-fluoro-n-propyl, and 3,3-difluoro-n-propyl are preferred, and methyl, ethyl, and n-propyl are more preferred in view of ready production of the carbonate.

In the particular linear carbonate represented by the formula (1), the configuration of the formula may preferably be left-right asymmetric. That is, $R^a$ in the above formula (1) preferably has a structure different from

[Chemical Formula 7]

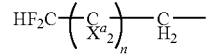

wherein n represents the same number as that of the formula (1) The asymmetry allows for a decreased boiling point of the solvent. In addition, such an asymmetric carbonate can enhance storage characteristics and cycle characteristics (Japanese Patent Application Laid-open Nos. HEI 2-148665 and HEI 4-104468).

However, among the carbonates having left-right symmetric configuration in the formula (1), bis(2,2-difluoroethyl) carbonate can be preferably used. That is, it is also preferred that in the formula (1), X represents hydrogen, n represents 0, and $R^a$ represents 2,2-difluoroethyl.

More preferably, among the particular linear carbonates, carbonates having a structure of left-right asymmetric configuration of the formula (1) are usually used.

Specific examples of the particular linear carbonate represented by the formula (1) include 2,2-difluoroethyl methyl carbonate, 2,2-difluoroethyl ethyl carbonate, 2,2-difluoroethyl-2'-fluoroethyl carbonate, bis(2,2-difluoroethyl)carbonate, 2,2-difluoroethyl-2',2',2'-trifluoroethyl carbonate, 2,2-difluoroethyl n-propyl carbonate, 2,2-difluoroethyl-3'-fluoro-n-propyl carbonate, 2,2-difluoro-3',3',3'-trifluoro-n-propyl carbonate, 3,3-difluoro-n-propyl methyl carbonate, 3,3-difluoro-n-propyl ethyl carbonate, 3,3-difluoro-n-propyl 2'-fluoroethyl carbonate, 3,3-difluoro-n-propyl-2',2'-difluoroethyl carbonate, 3,3-difluoro-n-propyl-2',2',2'-trifluoroethyl carbonate, 3,3-difluoro-n-propyl-n-propyl carbonate, 3,3-difluoro-n-propyl-3'-fluoro-n-propyl carbonate, bis(3,3-difluoro-n-propyl)carbonate, 3,3-difluoro-n-propyl-3',3',3'-trifluoro-n-propyl carbonate, methyl-2,2,3,3-tetrafluoro-n-propyl carbonate, ethyl-2,2,3,3-tetrafluoro-n-propyl carbonate, 2-fluoro-2',2',3',3'-tetrafluoro-n-propyl carbonate, 2,2-difluoroethyl-2',2',3',3'-tetrafluoro-n-propyl carbonate, 2,2,3,3-tetrafluoro-n-propyl-2',2',2'-trifluoroethyl carbonate, n-propyl-2,2,3,3-tetrafluoro-n-propyl carbonate, 3-fluoro-n-propyl-2',2',3',3'-tetrafluoro-n-propyl carbonate, 3,3-difluoro-n-propyl-2',2',3',3'-tetrafluoro-n-propyl carbonate, and bis(2,2,3,3-tetrafluoro-n-propyl)carbonate.

In particular, preferred are the particular linear carbonates having left-right asymmetric configuration of the formula (1), and bis(2,2-difluoroethyl)carbonate, as described above.

Among these, 2,2-difluoroethyl methyl carbonate, 2,2-difluoroethyl ethyl carbonate, bis(2,2-difluoroethyl)carbonate, and 2,2-difluoroethyl n-propyl carbonate are more preferred because these can be readily prepared.

More preferred are 2,2-difluoroethyl methyl carbonate, 2,2-difluoroethyl ethyl carbonate, and 2,2-difluoroethyl n-propyl carbonate among these.

When contained in the nonaqueous electrolytic solution in accordance with the first aspect of the present invention, the particular linear carbonates may be used either alone or in any combination thereof at any proportion.

When contained in the nonaqueous electrolytic solution in accordance with the first aspect of the present invention, the particular linear carbonate may be used in any amount unless significantly impairing the advantages of the present invention, but usually in an amount of 0.01% by weight or more and preferably 0.1% by weight or more. Below the lower limit, the nonaqueous electrolyte secondary cell containing the nonaqueous electrolytic solution in accordance with the first aspect of the present invention may not exhibit sufficiently enhanced cycle characteristics.

In particular, when contained as nonaqueous solvents in the nonaqueous electrolytic solution in accordance with the first aspect of the present invention, the amount of the particular linear carbonate is usually 95% by volume or less, and preferably 70% by volume or less based on the total amount of nonaqueous solvents other than electrolytes in the nonaqueous electrolytic solution. Above the upper limit, the electrolytes become insufficiently soluble, the electrolytic solution properties such as electric conductivity are impaired, and, as a result, the cell characteristics will be impaired.

When a nonaqueous electrolytic solution containing the above particular linear carbonate is contained in a nonaqueous electrolyte secondary cell, the charge and discharge cycle characteristics of the cell can be enhanced.

The reason for the improved charge and discharge cycle characteristics may be inferred as follows, although the detail is not clear: That is, when a nonaqueous electrolytic solution containing the particular linear carbonate is contained in a nonaqueous electrolyte secondary cell, the particular linear carbonate will react in the cell to form an excellent protective layer on the surface of a negative-electrode active material, thereby inhibiting side reactions and preventing the cycle degradation. In this case, both hydrogen and fluorine present on at least one terminal carbon atom in the particular linear carbonate represented by the formula (1), and it is considered to contribute to enhanced properties of the protective layer in any way.

Any known method can be used without limitation for producing the particular linear carbonate.

[I-2. Predetermined Carbonate]

Preferably, the nonaqueous electrolytic solution in accordance with the first aspect of the present invention further comprises a predetermined carbonate, in addition to the particular linear carbonate. The predetermined carbonate in the nonaqueous electrolytic solution in accordance with the first aspect of the present invention has at least one of an unsaturated bond and a halogen atom. That is, the predetermined carbonate in the nonaqueous electrolytic solution in accordance with the first aspect of the present invention may have only an unsaturated bond or only a halogen atom, or may have the both.

However, the particular linear carbonates should be excluded from the predetermined carbonates when they are contained in the nonaqueous electrolytic solution in accordance with the first aspect of the present invention. That is, in the nonaqueous electrolytic solution in accordance with the first aspect of the present invention, compounds that fall into the definition of the particular linear carbonates described above are not considered as the predetermined carbonates.

Among the predetermined carbonates other than the particular linear carbonates, any predetermined carbonate having an unsaturated bond (arbitrarily abbreviated as "predetermined unsaturated carbonate") may be used without limitation with the proviso that the predetermined carbonate has a carbon-carbon unsaturated bond, i.e. a carbon-carbon double bond or triple bond. The predetermined unsaturated carbonates having such unsaturated bonds also include carbonates having aromatic rings.

Examples of the predetermined unsaturated carbonate include vinylene carbonate derivatives, substituted ethylene carbonate derivatives by substituents with aromatic rings or carbon-carbon unsaturated bonds, phenyl carbonates, vinyl carbonates, and allyl carbonates.

Specific examples of the vinylene carbonate derivatives include vinylene carbonate, methyl vinylene carbonate, 4,5-dimethyl vinylene carbonate, phenyl vinylene carbonate, and 4,5-diphenyl vinylene carbonate.

Specific examples of the substituted ethylene carbonate derivatives by substituents with aromatic rings or carbon-carbon unsaturated bonds include such as vinyl ethylene carbonate, 4,5-divinyl ethylene carbonate, phenyl ethylene carbonate, and 4,5-diphenyl ethylene carbonate.

Specific examples of the phenyl carbonates include diphenyl carbonate, ethyl phenyl carbonate, methyl phenyl carbonate, and t-butyl phenyl carbonate.

Specific examples of the vinyl carbonates include divinyl carbonate and methyl vinyl carbonate.

Specific examples of the allyl carbonates include diallyl carbonate and allyl methyl carbonate.

Among these predetermined unsaturated carbonates preferred as the predetermined carbonate are the vinylene carbonate derivatives and the substituted ethylene carbonate derivatives by substituents with aromatic rings or carbon-carbon unsaturated bonds. Particularly preferred are vinylene carbonate, 4,5-diphenyl vinylene carbonate, 4,5-dimethyl vinylene carbonate, and vinyl ethylene carbonate because these can form stable surface protective films.

Among the predetermined carbonate having halogen atoms (arbitrarily abbreviated as "predetermined halogenated carbonate"), any halogenated carbonate other than the particular linear carbonates can be used without limitation.

Specific examples of the halogen atom contained in the predetermined halogenated carbonate include fluorine, chlorine, bromine, and iodine atoms. Among these preferred is fluorine or chlorine atom and in particular, fluorine atom is more preferable.

The number of the halogen atoms in the predetermined halogenated carbonate may be at least one without limitation, but usually six or less and preferably four or less. When the predetermined halogenated carbonate has multiple halogen atoms, they may be the same or different.

Examples of the predetermined halogenated carbonate include such as ethylene carbonate derivatives, dimethyl carbonate derivatives, ethyl methyl carbonate derivatives, and diethyl carbonate derivatives.

Specific examples of the ethylene carbonate derivatives include fluoroethylene carbonate, chloroethylene carbonate, 4,4-difluoroethylene carbonate, 4,5-difluoroethylene carbonate, 4,4-dichloroethylene carbonate, 4,5-dichloroethylene carbonate, 4-fluoro-4-methylethylene carbonate, 4-chloro-4-methylethylene carbonate, 4,5-difluoro-4-methylethylene carbonate, 4,5-dichloro-4-methylethylene carbonate, 4-fluoro-5-methylethylene carbonate, 4-chloro-5-methylethylene carbonate, 4,4-difluoro-5-methylethylene carbonate, 4,4-dichloro-5-methylethylene carbonate, 4-(fluoromethyl)-ethylene carbonate, 4-(chloromethyl)-ethylene carbonate, 4-(difluoromethyl)-ethylene carbonate, 4-(dichloromethyl)-ethylene carbonate, 4-(trifluoromethyl)-ethylene carbonate, 4-(trichloromethyl)-ethylene carbonate, 4-(fluoromethyl)-4-fluoroethylene carbonate, 4-(chloromethyl)-4-chloroethylene carbonate, 4-(fluoromethyl)-5-fluoroethylene carbonate, 4-(chloromethyl)-5-chloroethylene carbonate, 4-fluoro-4,5-dimethylethylene carbonate, 4-chloro-4,5-dimethylethylene carbonate, 4,5-difluoro-4,5-dimethylethylene carbonate, 4,5-dichloro-4,5-dimethylethylene carbonate, 4,4-difluoro-5,5-dimethylethylene carbonate, and 4,4-dichloro-5,5-dimethylethylene carbonate.

Specific examples of the dimethyl carbonate derivatives include such as fluoromethyl methyl carbonate, difluoromethyl methyl carbonate, trifluoromethyl methyl carbonate, bis(fluoromethyl)carbonate, bis(difluoro)methyl carbonate, bis(trifluoro)methyl carbonate, chloromethyl methyl carbonate, dichloromethyl methyl carbonate, trichloromethyl methyl carbonate, bis(chloromethyl)carbonate, bis(dichloro)methyl carbonate, and bis(trichloro)methyl carbonate.

Specific examples of the ethyl methyl carbonate derivatives include such as 2-fluoroethyl methyl carbonate, ethyl fluoromethyl carbonate, 2-fluoroethyl fluoromethyl carbonate, ethyl difluoromethyl carbonate, 2,2,2-trifluoroethyl methyl carbonate, 2-fluoroethyl difluoromethyl carbonate, ethyl trifluoromethyl carbonate, 2-chloroethyl methyl carbonate, ethyl chloromethyl carbonate, 2,2-dichloroethyl methyl carbonate, 2-chloroethyl chloromethyl carbonate, ethyl dichloromethyl carbonate, 2,2,2-trichloroethyl methyl carbonate, 2,2-dichloroethyl chloromethyl carbonate, 2-chloroethyl dichloromethyl carbonate, and ethyl trichloromethyl carbonate.

Specific examples of the diethyl carbonate derivatives include such as ethyl-(2-fluoroethyl)carbonate, bis(2-fluoroethyl)carbonate, ethyl-(2,2,2-trifluoroethyl)carbonate, 2,2,2-trifluoroethyl-2'-fluoroethyl carbonate, bis(2,2,2-trifluoroethyl)carbonate, ethyl-(2-chloroethyl)carbonate, ethyl-(2,2-dichloroethyl)carbonate, bis(2-chloroethyl)carbonate, ethyl-(2,2,2-trichloroethyl)carbonate, 2,2-dichloroethyl-2'-chloroethyl carbonate, bis(2,2-dichloroethyl)carbonate, 2,2,2-trichloroethyl-2'-chloroethyl carbonate, 2,2,2-trichloroethyl-2',2'-dichloroethyl carbonate, and bis(2,2,2-trichloroethyl)carbonate.

Among these predetermined halogenated carbonates, preferred are carbonates having fluorine atoms, and more preferred are ethylene carbonate derivatives having fluorine atoms. In particular, fluoroethylene carbonate, 4-(fluoromethyl)-ethylene carbonate, 4,4-difluoroethylene carbonate, and 4,5-difluoroethylene carbonate are preferably used because they can form surface protective films.

In addition, the predetermined carbonate can have both an unsaturated bond and a halogen atom (arbitrarily abbreviated as "predetermined halogenated unsaturated carbonate"). The predetermined halogenated unsaturated carbonate may be any halogenated unsaturated carbonate that does not significantly impair the advantages of the present invention.

Examples of the predetermined halogenated unsaturated carbonate include such as vinylene carbonate derivatives, substituted ethylene carbonate derivatives by substituents with aromatic rings or carbon-carbon unsaturated bonds, phenyl carbonates, vinyl carbonates, and allyl carbonates.

Specific examples of the vinylene carbonate derivatives include such as fluorovinylene carbonate, 4-fluoro-5-methylvinylene carbonate, 4-fluoro-5-phenylvinylene carbonate, chlorovinylene carbonate, 4-chloro-5-methylvinylene carbonate, and 4-chloro-5-phenylvinylene carbonate.

Specific examples of the substitutedethylene carbonate derivatives by substituents with aromatic rings or carbon-carbon unsaturated bonds include such as 4-fluoro-4-vinylethylene carbonate, 4-fluoro-5-vinylethylene carbonate, 4,4-difluoro-4-vinylethylene carbonate, 4,5-difluoro-4-vinylethylene carbonate, 4-chloro-5-vinylethylene carbonate, 4,4-dichloro-4-vinylethylene carbonate, 4,5-dichloro-4-vinylethylene carbonate, 4-fluoro-4,5-divinylethylene carbonate, 4,5-difluoro-4,5-divinylethylene carbonate, 4-chloro-4,5-divinylethylene carbonate, 4,5-dichloro-4,5-divinylethylene carbonate, 4-fluoro-4-phenylethylene carbonate, 4-fluoro-5-phenylethylene carbonate, 4,4-difluoro-5-phenylethylene carbonate, 4,5-difluoro-4-phenylethylene carbonate, 4-chloro-4-phenylethylene carbonate, 4-chloro-5-phenylethylene carbonate, 4,4-dichloro-5-phenylethylene carbonate, 4,5-dichloro-4-phenylethylene carbonate, 4,5-difluoro-4,5-diphenylethylene carbonate, and 4,5-dichloro-4,5-diphenylethylene carbonate.

Specific examples of the phenyl carbonates include such as fluoromethyl phenyl carbonate, 2-fluoroethyl phenyl carbonate, 2,2-difluoroethyl phenyl carbonate, 2,2,2-trifluoroethyl phenyl carbonate, chloromethyl phenyl carbonate, 2-chloroethyl phenyl carbonate, 2,2-dichloroethyl phenyl carbonate, and 2,2,2-trichloroethyl phenyl carbonate.

Specific examples of the vinyl carbonates include such as fluoromethyl vinyl carbonate, 2-fluoroethyl vinyl carbonate, 2,2-difluoroethyl vinyl carbonate, 2,2,2-trifluoroethyl vinyl carbonate, chloromethyl vinyl carbonate, 2-chloroethyl vinyl carbonate, 2,2-dichloroethyl vinyl carbonate, and 2,2,2-trichloroethyl vinyl carbonate.

Specific examples of the allyl carbonates include such as fluoromethyl allyl carbonate, 2-fluoroethyl allyl carbonate, 2,2-difluoroethyl allyl carbonate, 2,2,2-trifluoroethyl allyl carbonate, chloromethyl allyl carbonate, 2-chloroethyl allyl carbonate, 2,2-dichloroethyl allyl carbonate, and 2,2,2-trichloroethyl allyl carbonate.

Among the exemplary predetermined halogenated unsaturated carbonates mentioned above, it is especially preferred to use at least one selected from the group consisting of vinylene carbonate, vinyl ethylene carbonate, fluoroethylene carbonate, 4,5-difluoroethylene carbonate, and derivatives thereof as the predetermined carbonate because of high effects thereof when used alone.

The predetermined carbonate may have any molecular weight that does not significantly impair the advantages of the present invention, and the molecular weight is usually 50 or more and preferably 80 or more, and usually 250 or less, and preferably 150 or less. At a higher molecular weight of the predetermined carbonate, the solubility of the carbonate in a nonaqueous electrolytic solution may be too poor to exhibit the advantages of the present invention sufficiently.

The predetermined carbonates can be prepared by any known method without limitation.

The predetermined carbonates as described above may also be used either alone or in any combination thereof at any proportion in the nonaqueous electrolytic solution in accordance with the first aspect of the present invention.

The predetermined carbonate may be used in any amount in the nonaqueous electrolytic solution in accordance with the first aspect of the present invention without limitation within the scope that does not significantly impair the advantages of the present invention, and the amount of the predetermined carbonate is usually 0.01% by weight or more, preferably 0.1% by weight or more, and more preferably 0.3% by weight or more, and usually 70% by weight or less, preferably 50% by weight or less, and more preferably 40% by weight or less of the nonaqueous electrolytic solution in accordance with the first aspect of the present invention. Below the lower limit, a nonaqueous electrolyte secondary cell containing the nonaqueous electrolytic solution in accordance with the first aspect of the present invention may not exhibit sufficiently enhanced cycle characteristics. At a higher proportion of the predetermined carbonate, a nonaqueous electrolyte secondary cell containing the nonaqueous electrolytic solution in accordance with the first aspect of the present invention tends to impair its high-temperature preservation characteristics and trickle charge characteristics, and particularly may increase the amount of gas generation and decrease its discharge capacity maintenance rate.

In the nonaqueous electrolytic solution in accordance with the first aspect of the present invention, the particular linear carbonate and the predetermined carbonate may be used in any ratio. The ratio of "the weight of the particular linear carbonate to the weight of the predetermined carbonate" is usually 0.0001 or more, preferably 0.001 or more, and more preferably 0.01 or more, and usually 1000 or less, preferably 100 or less, and more preferably 10 or less. At a ratio that is lower or higher than this range, synergistic effects by the combination may not be exhibited.

When a nonaqueous electrolytic solution containing both the above described particular linear carbonate and the predetermined carbonate is contained in a nonaqueous electrolyte secondary cell, charge and discharge cycle characteristics of the cell can be enhanced. The reason for this may be inferred as follows, although the detail is not clear: The particular linear carbonate and the predetermined carbonate in the nonaqueous electrolytic solution will react together, and form an excellent protective film on the surface of a negative-electrode active material, thereby inhibiting side reactions and preventing the cycle degradation. In addition, an electrolytic solution containing both the particular linear carbonate and the predetermined carbonate is considered to contribute to enhanced properties of the protective film in any way.

[I-3. Nonaqueous Solvent]

The nonaqueous electrolytic solution in accordance with the first aspect of the present invention can comprises any nonaqueous solvent that does not significantly impair the advantages of the present invention. The particular linear carbonates or the predetermined carbonates mentioned above can also be used as the nonaqueous solvent. The nonaqueous solvents including the particular linear carbonates or the predetermined carbonates may be used either alone or in any combination thereof at any proportion.

Examples of the nonaqueous solvents that are commonly used include such as cyclic carbonates, linear carbonates, linear and cyclic carboxylic esters, linear and cyclic ethers, phosphorus-containing organic solvents, and sulfur-containing organic solvents.

Nonlimiting examples of the cyclic carbonates that are commonly used include such as ethylene carbonate, propylene carbonate, and butylene carbonate. Among these preferred are ethylene carbonate and propylene carbonate having high dielectric constants, which facilitate dissolution of solutes and improve cycle characteristics of nonaqueous electrolyte secondary cells.

Examples of the linear carbonates that are commonly used include, but not limited to, such as dimethyl carbonate, ethyl methyl carbonate, diethyl carbonate, methyl n-propyl carbonate, ethyl n-propyl carbonate, and di-n-propyl carbonate. Among these preferred are dimethyl carbonate, ethyl methyl carbonate, diethyl carbonate, methyl n-propyl carbonate, and ethyl n-propyl carbonate, and especially preferred are dimethyl carbonate, ethyl methyl carbonate and diethyl carbonate because these carbonates ensure improved cycle characteristics of nonaqueous electrolyte secondary cells.

Examples of the linear carboxylic acid esters that are commonly used include, but not limited to, such as methyl acetate, ethyl acetate, n-propyl acetate, i-propyl acetate, n-butyl acetate, i-butyl acetate, t-butyl acetate, methyl propionate, ethyl propionate, n-propyl propionate, i-propyl propionate, n-butyl propionate, i-butyl propionate, and t-butyl propionate. Among these, more preferred are ethyl acetate, methyl propionate, and ethyl propionate. In addition, the particular linear carbonates represented by the above formula (1) as the linear carbonates can also be used.

Examples of the cyclic carboxylic acid esters that are commonly used include, but not limited to, γ-butyrolactone, γ-valerolactone, and δ-valerolactone. Among these, γ-butyrolactone is more preferred.

Examples of the linear ethers that are commonly used include, but not limited to, such as dimethoxymethane, dimethoxyethane, diethoxymethane, diethoxyethane, ethoxymethoxymethane, and ethoxymethoxyethane. Among these, dimethoxyethane and diethoxyethane are more preferred.

Examples of the cyclic ethers that are commonly used include, but not limited to, such as tetrahydrofuran and 2-methyltetrahydrofuran.

Examples of the phosphorus-containing organic solvents that are commonly used include, but not limited to, phosphate esters such as trimethyl phosphate, triethyl phosphate, and triphenyl phosphate; phosphite esters such as trimethyl phosphite, triethyl phosphite, and triphenyl phosphite; phosphine oxides such as trimethylphosphine oxide, triethylphosphine oxide, and triphenylphosphine oxide.

Examples of the sulfur-containing organic solvents that are commonly used include, but not limited to, such as ethylene sulfite, 1,4-propane sultone, 1,4-butane sultone, methyl methanesulfonate, busulfan, sulfolane, sulfolene, dimethyl sulfone, diphenyl sulfone, methyl phenyl sulfone, dibutyl disulfide, dicyclohexyl disulfide, tetramethylthiuram monosulfide, N,N-dimethylmethanesulfonamide, and N,N-diethylmethanesulfonamide.

Among these, the cyclic carbonates, i.e., ethylene carbonate and/or propylene carbonate are preferably used, and more preferably used as a mixture with the linear carbonates.

In such combined use of the cyclic carbonates and the linear carbonates as the nonaqueous solvent, the suitable amount of the linear carbonate in the nonaqueous solvent in the nonaqueous electrolytic solution in accordance with the first aspect of the present invention is usually 30% by volume or more and preferably 50% by volume or more, and usually 95% by volume or less and preferably 90% by volume or less. The suitable amount of the cyclic carbonate in the nonaqueous solvent in the nonaqueous electrolytic solution in accordance with the first aspect of the present invention is usually 5% by volume or more and preferably 10% by volume or more, and usually 50% by volume or less and preferably 40% by volume or less. When containing the linear carbonate in a lower amount than this range, the nonaqueous electrolytic solution in accordance with the first aspect of the present invention may have an increased viscosity. When containing the linear carbonate in a higher amount than this range, the nonaqueous electrolytic solution may have a decreased degree of dissociation of the electrolyte, i.e., lithium salt, and then may have a decreased electric conductivity.

[I-4. Electrolyte]

The nonaqueous electrolytic solution in accordance with the first aspect of the present invention may contain any known electrolyte that is contained in an intended nonaqueous electrolyte secondary cell as electrolyte. Lithium secondary cells containing nonaqueous electrolytic solutions in accordance with the first aspect of the present invention typically contain lithium salts as the electrolytes.

Specific examples of the electrolytes include inorganic lithium salts such as $LiClO_4$, $LiAsF_6$, $LiPF_6$, $Li_2CO_3$, and $LiBF_4$; fluorine-containing organic lithium salts such as $LiCF_3SO_3$, $LiN(CF_3SO_2)_2$, $LiN(C_2F_5SO_2)_2$, lithium cyclic-1,4-perfluoropropanedisulfonylimide, $LiN(CF_3SO_2)(C_4F_9SO_2)$, $LiC(CF_3SO_2)_3$, $LiPF_4(CF_3)_2$, $LiPF_4(C_2F_5)_2$, $LiPF_4(CF_3SO_2)_2$, $LiPF_4(C_2F_5SO_2)_2$, $LiBF_2(CF_3)_2$, $LiBF_2(C_2F_5)_2$, $LiBF_2(CF_3SO_2)_2$, $LiBF_2(C_2F_5SO_2)_2$, and lithium bis(oxalato)borate; sodium or potassium salts such as $KPF_6$, $NaPF_6$, $NaBF_4$, and $Na_2CF_3SO_3$. Among these preferred are $LiPF_6$, $LiBF_4$, $LiCF_3SO_3$, $LiN(CF_3SO_2)_2$, and $LiN(C_2F_5SO_2)_2$, and especially preferred are $LiPF_6$ and $LiBF_4$.

The electrolytes may be used either alone or in any combination thereof at any proportion. In particular, combined use of two specific inorganic lithium salts or combined use of an inorganic lithium salt with a fluorine-containing organic lithium salt is preferred because gas generation is suppressed during a continuous charging mode or degradation is suppressed during high-temperature preservation. Especially preferred are combined use of $LiPF_6$ with $LiBF_4$ or combined use of an inorganic lithium salt, e.g. $LiPF_6$ or $LiBF_4$, with a fluorine-containing organic lithium salt, e.g. $LiCF_3SO_3$, $LiN(CF_3SO_2)_2$, or $LiN(C_2F_5SO_2)_2$.

When both $LiPF_6$ and $LiBF_4$ are used together, the amount of $LiBF_4$ in a preferred embodiment ranges from 0.01% by weight to 20% by weight based on the total amount of electrolytes. Since $LiBF_4$ has a low degree of dissociation, an electrolytic solution containing a significantly high proportion of $LiBF_4$ would have an increased resistance.

When an inorganic lithium salts such as $LiPF_6$ and $LiBF_4$ and fluorine-containing organic lithium salts such as $LiCF_3SO_3$, $LiN(CF_3SO_2)_2$, and $LiN(C_2F_5SO_2)_2$ are used together, it is desirable that the amount of the inorganic lithium salt is usually in a range from 70% by weight to 99% by weight based on the total amount of the electrolytes. In general, the fluorine-containing organic lithium salts have a higher molecular weight than the inorganic lithium salts and an electrolyte containing a significantly high proportion of the fluorine-containing organic lithium salt may reduce the proportion of the solvent to the entire electrolytic solution and increase its resistance.

The lithium salt in a nonaqueous electrolytic solution in accordance with the present invention may be used in any concentration that does not significantly impair the advantages of the present invention, and the concentration of the lithium salt is usually 0.5 $mol \cdot dm^{-3}$ or more, preferably 0.6 $mol \cdot dm^{-3}$ or more, and more preferably 0.8 $mol \cdot dm^{-3}$ or more, and usually 3 $mol \cdot dm^{-3}$ or less, preferably 2 $mol \cdot dm^{-3}$ or less, and more preferably 1.5 $mol \cdot dm^{-3}$ or less. A nonaqueous electrolytic solution containing a significantly low concentration of lithium salt may have an insufficient electric conductivity. A nonaqueous electrolytic solution containing a significantly high concentration of lithium salt may also have a decreased electric conductivity due to rise in viscosity, so that a nonaqueous electrolyte secondary cell containing the nonaqueous electrolytic solution in accordance with the first aspect of the present invention may have low performance.

[I-5. Additive]

Preferably, the nonaqueous electrolytic solution in accordance with the first aspect of the present invention contains various additives that do not significantly impair the advantages of the present invention. Any conventional known additive can be used either alone or in any combination thereof at any proportion. Examples of such additives include such as overcharge protection agents, and aids for improving capacity maintenance and cycle characteristics after high-temperature preservation.

Examples of the overcharge protection agents include aromatic compounds such as biphenyls, alkylbiphenyls, terphenyls, partially hydrogenated terphenyls, cyclohexylbenzene, t-butylbenzene, t-amylbenzene, diphenyl ether, and dibenzofuran; partially fluorinated aromatic compounds mentioned above such as 2-fluorobiphenyl, o-cyclohexylfluorobenzene, and p-cyclohexylfluorobenzene; and fluorine-containing anisoles such as 2,4-difluoroanisole, 2,5-difluoroanisole, and 2,6-difluoroanisole.

The overcharge protection agents may be used either alone or in any combination thereof at any proportion.

The nonaqueous electrolytic solution in accordance with the first aspect of the present invention may contain the overcharge protection agents in any concentration that does not significantly impair the advantages of the present invention, and the concentration of the overcharge protection agents is usually 0.1% by weight to 5% by weight based on the entire nonaqueous electrolytic solution. Incorporation of overcharge protection agents into a nonaqueous electrolytic solution is preferred because these agents can inhibit a nonaqueous electrolyte secondary cell from exploding and igniting even when the cell is overcharged, thereby enhancing the safety of the cell.

Examples of aids for improving capacity maintenance and cycle characteristics after high-temperature preservation include carbonate compounds such as vinylene carbonate, vinyl ethylene carbonate, fluoroethylene carbonate, 4-(trifluoromethyl)-ethylene carbonate, phenyl ethylene carbonate, erythritan carbonate, and spiro-bis-dimethylene carbonate; carboxylic anhydrides such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride, and phenylsuccinic anhydride; sulfur-containing compounds such as ethylene sulfite, 1,4-propane sultone, 1,4-butane sultone, methyl methanesulfonate, busulfan, sulfolane, sulfolene, dimethyl sulfone, diphenyl sulfone, methyl phenyl sulfone, dibutyl disulfide, dicyclohexyl disulfide, tetramethylthiuram monosulfide, N,N-dimethylmethanesulfonamide, and N,N-diethylmethanesulfonamide; nitrogen-containing compounds such as 1-methyl-2-pyrrolidinone, 1-methyl-2-piperidone, 4-methyl-2-oxazolidinone, 1,4-dimethyl-2-imidazolidinone, and N-methylsuccinimide; hydrocarbons such as heptane, octane, and cycloheptane; and fluorine-containing aromatic compounds such as fluorobenzene, difluorobenzene, and benzotrifluoride.

The aids may be used either alone or in any combination thereof at any proportion.

The nonaqueous electrolytic solution in accordance with the first aspect of the present invention can contain the aids in any concentration that does not significantly impair the advantages of the present invention, and the concentration of the aids is usually 0.1% by weight to 5% by weight based on the entire nonaqueous electrolytic solution.

[II. Nonaqueous Electrolytic Solution of Second Aspect]

The nonaqueous electrolytic solution in accordance with the second aspect of the present invention comprises 0.01% by weight to 10% by weight of a compound represented by the following formula (2) (hereinafter arbitrarily referred to as "particular compound (2)"):

[Chemical Formula 8]

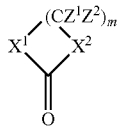
(2)

wherein $X^1$ represents oxygen, sulfur, $CD^1D^2$ or $NE^1$, wherein $D^1$ and $D^2$ represent each independently hydrogen, or any group capable of being attached to carbon, and $E^1$ represents hydrogen, or a group capable of being attached to nitrogen;

$X^2$ represents oxygen, sulfur, or $NE^1$;

$Z^1$ and $Z^2$ represent each independently hydrogen, or a group capable of being attached to carbon, with the proviso that at least one of $Z^1$, $Z^2$, $D^1$, $D^2$, and $E^1$ represents alkyl in which both at least one hydrogen atom and at least one fluorine atom are attached to at least one terminal carbon; and m represents a natural number.

[II-1. Particular Compound (2)]

The particular compound (2) contained in the nonaqueous electrolytic solution in accordance with the second aspect of the present invention is represented by the formula (2).

$X^1$ in the formula (2) represents oxygen, sulfur, $CD^1D^2$ or $NE^1$.

In the units (atomic groups) represented by $CD^1D^2$, $D^1$ and $D^2$ represent hydrogen, or any group capable of being attached to carbon. $D^1$ and $D^2$ may be the same or different from each other. They may also be combined together to form a ring.

Specific examples of $D^1$ and $D^2$ include halogen atoms such as fluorine, chloride, and bromine; and substituted or unsubstituted alkyl, alkoxy, alkylcarboxyl, and alkoxycarboxyl groups such as methyl, ethyl, fluoromethyl, trifluoromethyl, and 2,2,2-trifluoroethyl.

Preferably, $D^1$ and $D^2$ represent hydrogen, fluorine, unsubstituted alkyl, or fluorine-substituted alkyl in particular. In this case, preferred unsubstituted alkyls or fluorine-substituted alkyls are methyl, ethyl, fluoromethyl, trifluoromethyl, and 2,2,2-trifluoroethyl in view of ready production and safety.

In the units represented by $NE^1$, $E^1$ represents hydrogen, or a group capable of being attached to nitrogen.

Specific examples of $E^1$ include halogen atoms such as fluorine, chloride, and bromine; and substituted or unsubstituted alkyl, alkoxy, alkylcarboxyl, and alkoxycarboxyl groups such as methyl, ethyl, fluoromethyl, trifluoromethyl, and 2,2,2-trifluoroethyl.

Preferably, $E^1$ also represents hydrogen, fluorine, unsubstituted alkyl, or fluorine-substituted alkyl. In this case, preferred unsubstituted alkyls or fluorine-substituted alkyls are methyl, ethyl, fluoromethyl, trifluoromethyl, 2-fluoroethyl, and 2,2,2-trifluoroethyl in view of ready production and safety.

Among these, more preferred are the units having no substituent, or having unsubstituted alkyl or fluorine-substituted alkyl as the substituent as $X^1$ in view of electrochemical stability. That is, $X^1$ may preferably be at least one selected from the group consisting of oxygen, sulfur, $CD^1D^2$ having only unsubstituted alkyl or alkyl substituted by fluorine alone as $D^1$ and $D^2$, and $NE^1$ having only unsubstituted alkyl or alkyl substituted by fluorine alone as $E^1$.

More preferably, $X^1$ is oxygen.

$X^2$ in the formula (2) represents oxygen, sulfur, or $NE^1$.

In $NE^1$, $E^1$ is the same as described above for $X^1$.

Among these, more preferred are the units having no substituent, or having unsubstituted alkyl or fluorine-substituted alkyl as the substituent as $X^2$ in view of electrochemical stability. That is, $X^2$ may preferably be at least one selected from the group consisting of oxygen, sulfur, and $NE^1$ having only unsubstituted alkyl or alkyl substituted by fluorine alone as $E^1$.

More preferably, $X^2$ is also oxygen in view of electrochemical stability.

In the formula (2), $Z^1$ and $Z^2$ represent hydrogen, or any group capable of being attached to carbon, like $D^1$ and $D^2$. $Z^1$ and $Z^2$ may be the same or different from each other. They may be also be combined together to form a ring.

Specific examples of $Z^1$ and $Z^2$ include halogen atoms such as fluorine, chloride, and bromine; and substituted or unsubstituted alkyl, alkoxy, alkylcarboxyl, and alkoxycarboxyl groups such as methyl, ethyl, fluoromethyl, trifluoromethyl, and 2,2,2-trifluoroethyl.

Preferably, $Z^1$ and $Z^2$ represent hydrogen, fluorine, unsubstituted alkyl, or fluorine-substituted alkyl in particular. In this case, preferred unsubstituted alkyls or fluorine-substituted alkyls are methyl, ethyl, fluoromethyl, trifluoromethyl, and 2,2,2-trifluoroethyl. This can provide an advantage of enhancing the electrical stability of particular compounds (2) represented by the formula (2).

In the formula (2), m represents a natural number. In view of the ring stability of the cyclic compound represented by the formula (2), i.e., the particular compound (2), especially preferably, m represents two or three such that the compound (2) is a five- or six-membered ring. More preferably, for similar reason, m represents two such that the particular compound (2) is a five-membered ring when neither $X^1$ nor $X^2$ in the formula (2) represents the units containing carbon.

In the formula (2), at least one of $Z^1$, $Z^2$, $D^1$, $D^2$, and $E^1$ is alkyl in which both at least one hydrogen atom and at least one fluorine atom are attached to at least one of the terminal carbon atoms (hereinafter arbitrarily referred to as "particular substituted alkyl $R^f$").

The particular substituted alkyls $R^f$ may have any substituent that does not significantly impair the advantages of the present invention. That is, at least one of the terminal carbon atoms in the particular substituted alkyl $R^f$ has at least one fluorine atom and at least one hydrogen atom left unsubstituted, and may have a substituent other than the fluorine atom. Examples of the substituents that the particular substituted alkyls $R^f$ have include such as fluorine, alkyl, allyl, alkoxy, alkylcarboxy, and alkoxycarboxy.

Preferably, the particular substituted alkyls $R^f$ have no substituent other than fluorine in view of the electrochemical stability of the particular compounds (2) represented by the formula (2). That is, the particular substituted alkyls $R^f$ are preferably substituted by fluorine alone.

The carbon number of the particular substituted alkyl $R^f$ may also be unlimited with the proviso that the number is usually ten or less, preferably five or less, and more preferably three or less since the particular substituted alkyl $R^f$ having a significantly high molecular weight may not exhibit effects comparable to the amount of the particular compound (2) used.

Examples of the particular substituted alkyls $R^f$ that meet the above requirements include fluoromethyl, difluoromethyl, 2-fluoroethyl, 2,2-difluoroethyl, 1,2-difluoroethyl, 1,1,2-trifluoroethyl, 1,2,2-trifluoroethyl, 1,1,2,2-tetrafluoroethyl, 3-fluoro-n-propyl, 1,3-difluoro-n-propyl, 2,3-difluoro-n-propyl, 3,3-difluoro-n-propyl, 1,1,3-trifluoro-n-propyl, 1,2,3-trifluoro-n-propyl, 1,3,3-trifluoro-n-propyl, 2,2,3-trifluoro-n-propyl, 1,1,2,3-tetrafluoro-n-propyl, 1,1,3,3-tetrafluoro-n-propyl, 1,2,2,3-tetrafluoro-n-propyl, 1,2,3,3-tetrafluoro-n-propyl, 2,2,3,3-tetrafluoro-n-propyl, 1,1,2,2,3-pentafluoro-n-propyl, 1,1,2,3,3-pentafluoro-n-propyl, 1,2,2,3,3-pentafluoro-n-propyl, 1,1,2,2,3,3-hexafluoro-n-propyl, 1-fluoro-i-propyl, 1,2-difluoro-i-propyl, 1,3-difluoro-i-propyl, 1,1,2-trifluoro-i-propyl, 1,1,3-trifluoro-i-propyl, 1,2,3-trifluoro-i-propyl, 1,1,1,3-tetrafluoro-i-propyl, 1,1,2,3-tetrafluoro-i-propyl, 1,1,3,3-tetrafluoro-i-propyl, 1,1,1,2,3-pentafluoro-i-propyl, 1,1,1,3,3-pentafluoro-i-propyl, 1,1,2,3,3-pentafluoro-i-propyl, and 1,1,1,2,3,3-hexafluoro-i-propyl.

Among these preferred are fluoromethyl, difluoromethyl, 2-fluoroethyl, 2,2-difluoroethyl, 1,1,2,2-tetrafluoroethyl, and 3-fluoro-n-propyl group, and more preferred are fluoromethyl and difluoromethyl in view of ready production.

The particular substituted alkyls $R^f$ may be used either alone or in any combination thereof at any proportion.

The particular compound (2) may have any molecular weight that does not significantly impair the advantages of the present invention, and the molecular weight is usually 119 or more. The upper limit of the molecular weight is not defined, but is preferably as low as possible. It is practical to use particular compounds (2) having a molecular weight of usually 300 or less and preferably 200 or less.

Examples of the particular compounds (2) that meet the above requirements include fluoromethyl ethylene carbonate, difluoromethyl ethylene carbonate, (2-fluoroethyl)ethylene carbonate, (2,2-difluoroethyl)ethylene carbonate, 4-(fluoromethyl)-4-fluoroethylene carbonate, 4-(fluoromethyl)-5-fluoroethylene carbonate, 4-(2-fluoroethyl)-4-fluoroethylene carbonate, 4-(2-fluoroethyl)-5-fluoroethylene carbonate, 4-fluoromethyl-2-oxazolidinone, 5-fluoromethyl-2-oxazolidinone, 4-difluoromethyl-2-oxazolidinone, 5-difluoromethyl-2-oxazolidinone, 4-fluoromethyl-4-fluoro-2-oxazolidinone, 4-fluoromethyl-5-fluoro-2-oxazolidinone, 4-(2-fluoroethyl)-2-oxazolidinone, 5-(2-fluoroethyl)-2-oxazolidinone, 4-(2,2-difluoroethyl)-2-oxazolidinone, 5-(2,2-difluoroethyl)-2-oxazolidinone, 4-fluoromethyl-3-methyl-2-oxazolidinone, 5-fluoromethyl-3-methyl-2-oxazolidinone, 4-difluoromethyl-3-methyl-2-oxazolidinone, 5-difluoromethyl-3-methyl-2-oxazolidinone, 4-fluoromethyl-4-fluoro-3-methyl-2-oxazolidinone, 4-fluoromethyl-5-fluoro-3-methyl-2-oxazolidinone, 4-(2-fluoroethyl)-3-methyl-2-oxazolidinone, 5-(2-fluoroethyl)-3-methyl-2-oxazolidinone, 4-(2,2-difluoroethyl)-3-methyl-2-oxazolidinone, 5-(2,2-difluoroethyl)-3-methyl-2-oxazolidinone, 4-fluoromethyl-3-ethyl-2-oxazolidinone, 5-fluoromethyl-3-ethyl-2-oxazolidinone, 4-difluoromethyl-3-ethyl-2-oxazolidinone, 5-difluoromethyl-3-ethyl-2-oxazolidinone, 4-fluoromethyl-4-fluoro-3-ethyl-2-oxazolidinone, 4-fluoromethyl-5-fluoro-3-ethyl-2-oxazolidinone, 4-(2-fluoroethyl)-3-ethyl-2-oxazolidinone, 5-(2-fluoroethyl)-3-ethyl-2-oxazolidinone, 4-(2,2-difluoroethyl)-3-ethyl-2-oxazolidinone, 5-(2,2-difluoroethyl)-3-ethyl-2-oxazolidinone, 3-fluoromethyl-2-oxazolidinone, 3-difluoromethyl-2-oxazolidinone, 3-(2-fluoroethyl)-2-oxazolidinone, 3-(2,2-difluoroethyl)-2-oxazolidinone, 4-fluoromethyl-3-fluoromethyl-2-oxazolidinone, 5-fluoromethyl-3-fluoromethyl-2-oxazolidinone, 4-(2-fluoroethyl)-3-fluoromethyl-2-oxazolidinone, 5-(2-fluoroethyl)-3-fluoromethyl-2-oxazolidinone, 4-fluoromethyl-3-(2,2,2-trifluoroethyl)-2-oxazolidinone, 4-fluoromethyl-2-imidazolidinone, 4-difluoromethyl-2-imidazolidinone, 4-(2-fluoroethyl)-2-imidazolidinone, 4-(2,2-difluoroethyl)-2-imidazolidinone, 4-fluoromethyl-1-methyl-2-imidazolidinone, 4-difluoromethyl-1-methyl-2-imidazolidinone, 4-(2-fluoroethyl)-1-methyl-2-imidazolidinone, 4-(2,2-difluoroethyl)-1-methyl-2-imidazolidinone, 5-fluoromethyl-1-methyl-2-imidazolidinone, 5-difluoromethyl-1-methyl-2-imidazolidinone, 5-(2-fluoroethyl)-1-methyl-2-imidazolidinone, 5-(2,2-difluoroethyl)-1-methyl-2-imidazolidinone, 4-fluoromethyl-1,3-dimethyl-2-imidazolidinone, 4-difluoromethyl-1,3-dimethyl-2-imidazolidinone, 4-(2-fluoroethyl)-1,3-dimethyl-2-imidazolidinone, 4-(2,2-difluoroethyl)-1,3-dimethyl-2-imidazolidinone, 1-fluoromethyl-2-imidazolidinone, 1-difluoromethyl-2-imidazolidinone, 1-(2-fluoroethyl)-2-imidazolidinone, 1-(2,2-difluoroethyl)-2-imidazolidinone, 3-fluoromethyltetrahydrofuran-2-one, 3-difluoromethyltetrahydrofuran-2-one, 3-(2-fluoroethyl)tetrahydrofuran-2-one, 3-(2,2-difluoroethyl)tetrahydrofuran-2-one, 4-fluoromethyltetrahydrofuran-2-one, 4-difluoromethyltetrahydrofuran-2-one, 4-(2-fluoroethyl)tetrahydrofuran-2-one, 4-(2,2-difluoroethyl)tetrahydrofuran-2-one, 5-fluoromethyltetrahydrofuran-2-one, 5-difluoromethyltetrahydrofuran-2-one, 5-(2-fluoroethyl)tetrahydrofuran-2-one, 5-(2,2-difluoroethyl)tetrahydrofuran-2-one, 3-fluoromethyltetrahydropyrrol-2-one, 3-difluoromethyltetrahydropyrrol-2-one, 3-(2-fluoroethyl)tetrahydropyrrol-2-one, 3-(2,2-difluoroethyl)tetrahydropyrrol-2-one, 4-fluoromethyltetrahydropyrrol-2-one, 4-difluoromethyltetrahydropyrrol-2-one, 4-(2-fluoroethyl)tetrahydropyrrol-2-one, 4-(2,2-difluoroethyl)tetrahydropyrrol-2-one, 5-fluoromethyltetrahydropyrrol-2-one, 5-difluoromethyltetrahydropyrrol-2-one, 5-(2-fluoroethyl)tetrahydropyrrol-2-one, 5-(2,2-difluoroethyl)tetrahydropyrrol-2-one, 3-fluoromethyl-1-methyltetrahydropyrrol-2-one, 3-difluoromethyl-1-methyltetrahydropyrrol-2-one, 3-(2-fluoroethyl)-1-methyltetrahydropyrrol-2-one, 3-(2,2-difluoroethyl)-1-methyltetrahydropyrrol-2-one, 4-fluoromethyl-1-methyltetrahydropyrrol-2-one, 4-difluoromethyl-1-methyltetrahydropyrrol-2-one, 4-(2-fluoroethyl)-1-methyltetrahydropyrrol-2-one, 4-(2,2-difluoroethyl)-1-methyltetrahydropyrrol-2-one, 5-fluoromethyl-1-methyltetrahydropyrrol-2-one, 5-difluoromethyl-1-methyltetrahydropyrrol-2-one, 5-(2-fluoroethyl)-1-methyltetrahydropyrrol-2-one, 5-(2,2-difluoroethyl)-1-methyltetrahydropyrrol-2-one, 3-fluoromethyl-1-ethyltetrahydropyrrol-2-one, 3-difluoromethyl-1-ethyltetrahydropyrrol-2-one, 3-(2-fluoroethyl)-1-ethyltetrahydropyrrol-2-one, 3-(2,2-difluoroethyl)-1-ethyltetrahydropyrrol-2-one, 4-fluoromethyl-1-ethyltetrahydropyrrol-2-one, 4-difluoromethyl-1-ethyltetrahydropyrrol-2-one, 4-(2-fluoroethyl)-1-ethyltetrahydropyrrol-2-one, 4-(2,2-difluoroethyl)-1-ethyltetrahydropyrrol-2-one, 5-fluoromethyl-1-ethyltetrahydropyrrol-2-one, 5-difluoromethyl-1-ethyltetrahydropyrrol-2-one, 5-(2-fluoroethyl)-1-ethyltetrahydropyrrol-2-one, 5-(2,2-difluoroethyl)-1-ethyltetrahydropyrrol-2-one, 1-fluoromethyletrahydropyrrol-2-one, 1-difluoromethyletrahydropyrrol-2-one, 1-(2-fluoroethyl)tetrahydropyrrol-2-one, 1-(2,2-difluoroethyl)tetrahydropyrrol-2-one, 3-difluoromethyl-1-methyltetrahydropyrrol-2-one, 3-(2-fluoroethyl)-1-methyltetrahydropyrrol-2-one, 3-(2,2-difluoroethyl)-1-methyltetrahydropyrrol-2-one, 3-fluoromethyl-1-fluoromethyltetrahydropyrrol-2-one, 3-difluoromethyl-1-fluoromethyltetrahydropyrrol-2-one, 3-(2-fluoroethyl)-1-fluoromethyltetrahydropyrrol-2-one, 3-(2,2- difluoroethyl)-1-fluoromethyltetrahydropyrrol-2-one, 4-fluoromethyl-1-fluoromethyltetrahydropyrrol-2-one, 4-difluoromethyl-1-fluoromethyltetrahydropyrrol-2-one, 4-(2-fluoroethyl)-1-fluoromethyltetrahydropyrrol-2-one, 4-(2,2-difluoroethyl)-1-fluoromethyltetrahydropyrrol-2-one, 5-fluoromethyl-1-fluoromethyltetrahydropyrrol-2-one, 5-difluoromethyl-1-fluoromethyltetrahydropyrrol-2-one, 5-(2-fluoroethyl)-1-fluoromethyltetrahydropyrrol-2-one, and 5-(2,2-difluoroethyl)-1-fluoromethyltetrahydropyrrol-2-one.

Among these preferred are those not containing nitrogen, e.g. fluoromethyl ethylene carbonate, difluoromethyl ethylene carbonate, (2-fluoroethyl)ethylene carbonate, (2,2-difluoroethyl)ethylene carbonate, 4-(fluoromethyl)-4-fluoroethylene carbonate, 4-(fluoromethyl)-5-fluoroethylene carbonate, 3-fluoromethyltetrahydrofuran-2-one, 3-difluoromethyltetrahydrofuran-2-one, 3-(2-fluoroethyl)tetrahydrofuran-2-one, 3-(2,2-difluoroethyl)tetrahydrofuran-2-one, 4-fluoromethyltetrahydrofuran-2-one, 4-difluoromethyltetrahydrofuran-2-one, 4-(2-fluoroethyl)tetrahydrofuran-2-one, 4-(2,2-difluoroethyl)tetrahydrofuran-2-one, 5-fluoromethyltetrahydrofuran-2-one, 5-difluoromethyltetrahydrofuran-2-one, 5-(2-fluoroethyl)tetrahydrofuran-2-one, and 5-(2,2-difluoroethyl)tetrahydrofuran-2-one for their stability.

More preferred are fluoromethyl ethylene carbonate, difluoromethyl ethylene carbonate, 3-fluoromethyltetrahydrofuran-2-one, 4-fluoromethyltetrahydrofuran-2-one, and 5-fluoromethyltetrahydrofuran-2-one, which have a high stability.

The particular compound (2) represented by the formula (2) may be used either alone or in any combination thereof at any proportion in a nonaqueous electrolytic solution.

When contained in the nonaqueous electrolytic solution in accordance with the second aspect of the present invention, the amount of the particular compound (2) is usually 0.01% by weight or more and preferably 0.1% by weight or more, and usually 10% by weight or less and preferably 5% by weight or less based on the nonaqueous electrolytic solution in accordance with the second aspect of the present invention. Below the lower limit, a nonaqueous electrolyte secondary cell containing the nonaqueous electrolytic solution in accordance with the second aspect of the present invention may not exhibit sufficiently enhanced cycle characteristics. Above the upper limit, an increased reactivity in the nonaqueous electrolytic solution will impair the cell characteristics of a nonaqueous electrolyte secondary cell.

When the particular compound (2) is contained in a nonaqueous electrolytic solution, a nonaqueous electrolyte secondary cell containing the nonaqueous electrolytic solution will enhance charge and discharge cycle characteristics. The reason for this may be inferred as follows, although the detail is not clear:

That is, when a nonaqueous electrolytic solution containing the particular compound (2) is contained in a nonaqueous electrolyte secondary cell, the particular compound (2) will react in the cell to form an excellent protective layer on the surface of a negative-electrode active material, thereby inhibiting side reactions and preventing the cycle degradation. Moreover, both hydrogen and fluorine present on at least one terminal carbon atom in the particular substituted alkyl Rf in the particular compound (2) represented by the formula (2), it is considered to contribute to enhanced properties of the protective layer in any way.

Nonaqueous electrolytic solutions containing compounds included in the group of the particular compounds (2) represented by the formula (2) are also described in Patent Documents 6 and 7. These documents 6 and 7, however, do not disclose such a constitution that provides significant advantages as in the present invention by using a predetermined amount of 0.01% by weight to 10% by weight of the particular compound (2).

In addition, through evaluation conducted with actual devices, the advantages are confirmed from the physical storage devices, i.e., electric double-layer capacitors in Patent Document 6. The advantages are not observed from the chemical cells in Patent Document 7.

Any known method can be used without limitation for producing the particular compound (2).

[II-2. Predetermined Carbonate]

Preferably, the nonaqueous electrolytic solution in accordance with the second aspect of the present invention further comprises a predetermined carbonate. The predetermined carbonate in the nonaqueous electrolytic solution in accordance with the second aspect of the present invention has at least one of an unsaturated bond and a halogen atom. That is, the predetermined carbonate in the nonaqueous electrolytic solution in accordance with the second aspect of the present invention may have only an unsaturated bond or only a halogen atom, or may have the both.

However, the particular compounds (2) should be excluded from the predetermined carbonates when they are contained in the nonaqueous electrolytic solution in accordance with the second aspect of the present invention. That is, in the nonaqueous electrolytic solution in accordance with the second aspect of the present invention, compounds that fall into the definition of the particular compounds (2) described above are not considered as the predetermined carbonates.

Among the predetermined carbonates other than the particular compounds (2), any predetermined carbonate having an unsaturated bond (arbitrarily abbreviated as "predetermined unsaturated carbonate") may be used without limitation with the proviso that the predetermined carbonate has a carbon-carbon unsaturated bond, i.e. a carbon-carbon double bond or triple bond. The predetermined unsaturated carbonates having such unsaturated bonds also include carbonates having aromatic rings.

Examples of the predetermined unsaturated carbonate include such as vinylene carbonate derivatives substituted, ethylene carbonate derivatives by substituents with aromatic rings or carbon-carbon unsaturated bonds, phenyl carbonates, vinyl carbonates, and allyl carbonates.

Specific examples of vinylene carbonate derivatives include such as vinylene carbonate, methyl vinylene carbonate, 4,5-dimethyl vinylene carbonate, phenyl vinylene carbonate, and 4,5-diphenyl vinylene carbonate.

Specific examples of substituted ethylene carbonate derivatives by substituents with aromatic rings or carbon-carbon unsaturated bonds include such as vinyl ethylene carbonate, 4,5-divinyl ethylene carbonate, phenyl ethylene carbonate, and 4,5-diphenyl ethylene carbonate.

Specific examples of phenyl carbonates include such as diphenyl carbonate, ethyl phenyl carbonate, methyl phenyl carbonate, and t-butyl phenyl carbonate.

Specific examples of vinyl carbonates include such as divinyl carbonate and methyl vinyl carbonate.

Specific examples of allyl carbonates include such as diallyl carbonate and allyl methyl carbonate.

Among these predetermined unsaturated carbonates preferred as the predetermined carbonate are the vinylene carbonate derivatives and the substituted ethylene carbonate derivatives by substituents with aromatic rings or carbon-carbon unsaturated bonds. Particularly preferred are vinylene carbonate, 4,5-diphenyl vinylene carbonate, 4,5-dimethyl vinylene carbonate, and vinyl ethylene carbonate because these can form stable surface protective films.

Among the predetermined carbonate having halogen atoms (arbitrarily abbreviated as "predetermined halogenated carbonate"), any halogenated carbonate can be used without limitation.

Specific examples of the halogen atom contained in the predetermined halogenated carbonate include fluorine, chlorine, bromine, and iodine atoms. Among these preferred is fluorine or chlorine atom and in particular, fluorine atom.

The number of the halogen atoms in the predetermined halogenated carbonate may be at least one without limitation, but usually no more than six, and preferably no more than four. When the predetermined halogenated carbonate has multiple halogen atoms, they may be the same or different.

Examples of the predetermined halogenated carbonate include ethylene carbonate derivatives, dimethyl carbonate derivatives, ethyl methyl carbonate derivatives, and diethyl carbonate derivatives.

Specific examples of the ethylene carbonate derivatives include such as fluoroethylene carbonate, chloroethylene carbonate, 4,4-difluoroethylene carbonate, 4,5-difluoroethylene carbonate, 4,4-dichloroethylene carbonate, 4,5-dichloroethylene carbonate, 4-fluoro-4-methylethylene carbonate, 4-chloro-4-methylethylene carbonate, 4,5-difluoro-4-methylethylene carbonate, 4,5-dichloro-4-methylethylene carbonate, 4-fluoro-5-methylethylene carbonate, 4-chloro-5-methylethylene carbonate, 4,4-difluoro-5-methylethylene carbonate, 4,4-dichloro-5-methylethylene carbonate, 4-(chloromethyl)-ethylene carbonate, 4-(dichloromethyl)-ethylene carbonate, 4-(trifluoromethyl)-ethylene carbonate, 4-(trichloromethyl)-ethylene carbonate, 4-(chloromethyl)-4-chloroethylene carbonate, 4-(chloromethyl)-5-chloroethylene carbonate, 4-fluoro-4,5-dimethylethylene carbonate, 4-chloro-4,5-dimethylethylene carbonate, 4,5-difluoro-4,5-dimethylethylene carbonate, 4,5-dichloro-4,5-dimethylethylene carbonate, 4,4-difluoro-5,5-dimethylethylene carbonate, and 4,4-dichloro-5,5-dimethylethylene carbonate.

Specific examples of the dimethyl carbonate derivatives include such as fluoromethyl methyl carbonate, difluoromethyl methyl carbonate, trifluoromethyl methyl carbonate, bis(fluoromethyl)carbonate, bis(difluoro)methyl carbonate, bis(trifluoro)methyl carbonate, chloromethyl methyl carbonate, dichloromethyl methyl carbonate, trichloromethyl methyl carbonate, bis(chloromethyl)carbonate, bis(dichloro)methyl carbonate, and bis(trichloro)methyl carbonate.

Specific examples of the ethyl methyl carbonate derivatives include such as 2-fluoroethyl methyl carbonate, ethyl fluoromethyl carbonate, 2-fluoroethyl fluoromethyl carbonate, 2,2-difluoroethyl methyl carbonate, ethyl difluoromethyl carbonate 2,2,2-trifluoroethyl methyl carbonate, 2-fluoroethyl difluoromethyl carbonate, ethyl trifluoromethyl carbonate, 2-chloroethyl methyl carbonate, ethyl chloromethyl carbonate, 2,2-dichloroethyl methyl carbonate, 2-chloroethyl chloromethyl carbonate, ethyl dichloromethyl carbonate, 2,2,2-trichloroethyl methyl carbonate, 2,2-dichloroethyl chloromethyl carbonate, 2-chloroethyl dichloromethyl carbonate, and ethyl trichloromethyl carbonate.

Specific examples of the diethyl carbonate derivatives include such as ethyl-(2-fluoroethyl)carbonate, bis(2-fluoroethyl)carbonate, 2,2-difluoroethyl ethyl carbonate, 2,2-difluoroethyl-2'-fluoroethyl carbonate, bis(2,2-difluoroethyl) carbonate, ethyl-(2,2,2-trifluoroethyl)carbonate, 2,2,2-trifluoroethyl-2'-fluoroethyl carbonate, 2,2,2-trifluoroethyl-2',2'-difluoroethyl carbonate, bis(2,2,2-trifluoroethyl) carbonate, ethyl-(2-chloroethyl)carbonate, ethyl-(2,2-dichloroethyl)carbonate, bis(2-chloroethyl)carbonate, ethyl-(2,2,2-trichloroethyl)carbonate, 2,2-dichloroethyl-2'-chloroethyl carbonate, bis(2,2-dichloroethyl)carbonate, 2,2,2-trichloroethyl-2'-chloroethyl carbonate, 2,2,2-trichloroethyl-2',2'-dichloroethyl carbonate, and bis(2,2,2-trichloroethyl) carbonate.

Among these predetermined halogenated carbonates, preferred are carbonates having fluorine atoms, and more preferred are ethylene carbonate derivatives having fluorine atoms. In particular, fluoroethylene carbonate, 4-(fluoromethyl)-ethylene carbonate, 4,4-difluoroethylene carbonate, and 4,5-difluoroethylene carbonate are preferably used because they can form surface protective films.

In addition, the predetermined carbonate can have both an unsaturated bond and a halogen atom (arbitrarily abbreviated as "predetermined halogenated unsaturated carbonate"). The predetermined halogenated unsaturated carbonate may be any halogenated unsaturated carbonate that does not significantly impair the advantages of the present invention.

Examples of the predetermined halogenated unsaturated carbonate include such as vinylene carbonate derivatives, substituted ethylene carbonate derivatives by substituents with aromatic rings or carbon-carbon unsaturated bonds, phenyl carbonates, vinyl carbonates, and allyl carbonates.

Specific examples of the vinylene carbonate derivatives include such as fluorovinylene carbonate, 4-fluoro-5-methylvinylene carbonate, 4-fluoro-5-phenylvinylene carbonate, chlorovinylene carbonate, 4-chloro-5-methylvinylene carbonate, and 4-chloro-5-phenylvinylene carbonate.

Specific examples of the substituted ethylene carbonate derivatives by substituents with aromatic rings or carbon-carbon unsaturated bonds include such as 4-fluoro-4-vinylethylene carbonate, 4-fluoro-5-vinylethylene carbonate, 4,4-difluoro-4-vinylethylene carbonate, 4,5-difluoro-4-vinylethylene carbonate, 4-chloro-5-vinylethylene carbonate, 4,4-dichloro-4-vinylethylene carbonate, 4,5-dichloro-4-vinylethylene carbonate, 4-fluoro-4,5-divinylethylene carbonate, 4,5-difluoro-4,5-divinylethylene carbonate, 4-chloro-4,5-divinylethylene carbonate, 4,5-dichloro-4,5-divinylethylene carbonate, 4-fluoro-4-phenylethylene carbonate, 4-fluoro-5-phenylethylene carbonate, 4,4-difluoro-5-phenylethylene carbonate, 4,5-difluoro-4-phenylethylene carbonate, 4-chloro-4-phenylethylene carbonate, 4-chloro-5-phenylethylene carbonate, 4,4-dichloro-5-phenylethylene carbonate, 4,5-dichloro-4-phenylethylene carbonate, 4,5-difluoro-4,5-diphenylethylene carbonate, and 4,5-dichloro-4,5-diphenylethylene carbonate.

Specific examples of the phenyl carbonates include such as fluoromethyl phenyl carbonate, 2-fluoroethyl phenyl carbonate, 2,2-difluoroethyl phenyl carbonate, 2,2,2-trifluoroethyl phenyl carbonate, chloromethyl phenyl carbonate, 2-chloroethyl phenyl carbonate, 2,2-dichloroethyl phenyl carbonate, and 2,2,2-trichloroethyl phenyl carbonate.

Specific examples of the vinyl carbonates include such as fluoromethyl vinyl carbonate, 2-fluoroethyl vinyl carbonate, 2,2-difluoroethyl vinyl carbonate, 2,2,2-trifluoroethyl vinyl carbonate, chloromethyl vinyl carbonate, 2-chloroethyl vinyl carbonate, 2,2-dichloroethyl vinyl carbonate, and 2,2,2-trichloroethyl vinyl carbonate.

Specific examples of the allyl carbonates include such as fluoromethyl allyl carbonate, 2-fluoroethyl allyl carbonate, 2,2-difluoroethyl allyl carbonate, 2,2,2-trifluoroethyl allyl carbonate, chloromethyl allyl carbonate, 2-chloroethyl allyl carbonate, 2,2-dichloroethyl allyl carbonate, and 2,2,2-trichloroethyl allyl carbonate.

Among the exemplary predetermined halogenated unsaturated carbonates mentioned above, it is especially preferred to use at least one selected from the group consisting of vinylene carbonate, vinyl ethylene carbonate, fluoroethylene carbonate, difluoroethylene carbonates, and derivatives thereof as the predetermined carbonate because of high effects thereof when used alone. Among the difluoroethylene carbonates, especially preferred is 4,5-difluoroethylene carbonate.

The predetermined carbonate may have any molecular weight that does not significantly impair the advantages of the present invention, and the molecular weight is usually 50 or more and preferably 80 or more, and usually 250 or less and preferably 150 or less. At a higher molecular weight of the predetermined carbonate, the solubility of the carbonate in a nonaqueous electrolytic solution may be too poor to exhibit the advantages of the present invention sufficiently.

The predetermined carbonates can be prepared by any known method without limitation.

The predetermined carbonates as described above may also be used either alone or in any combination thereof at any proportion in the nonaqueous electrolytic solution in accordance with the second aspect of the present invention.

The predetermined carbonate may be used in any amount in the nonaqueous electrolytic solution in accordance with the second aspect of the present invention without limitation within the scope that does not significantly impair the advantages of the present invention, and the amount of the predetermined carbonate is usually 0.01% by weight or more, preferably 0.1% by weight or more, and more preferably 0.3% by weight or more, and usually 70% by weight or less, preferably 50% by weight or less, and more preferably 40% by weight or less of the nonaqueous electrolytic solution in accordance with the second aspect of the present invention. Below the lower limit, a nonaqueous electrolyte secondary cell containing the nonaqueous electrolytic solution in accordance with the second aspect of the present invention may not exhibit sufficiently enhanced cycle characteristics. At a higher proportion of the predetermined carbonate, a nonaqueous electrolyte secondary cell containing the nonaqueous electrolytic solution in accordance with the second aspect of the present invention tends to impair its high-temperature preservation characteristics and trickle charge characteristics, and particularly may increase the amount of gas generation and decrease its discharge capacity maintenance rate.

In the nonaqueous electrolytic solution in accordance with the second aspect of the present invention, the particular compound (2) and the predetermined carbonate may be used in any ratio. The ratio of "the amount of the particular compound (2) to the amount of the predetermined carbonate" is usually 0.0001 or more, preferably 0.001 or more, and more preferably 0.01 or more, and usually 1000 or less, preferably 100 or less, and more preferably 10 or less. At a ratio that is lower or higher than this range, synergistic effects by the combination may not be exhibited.

When a nonaqueous electrolytic solution containing both the particular compound (2) and the predetermined carbonate is contained in a nonaqueous electrolyte secondary cell, charge and discharge cycle characteristics of the cell can be enhanced. The reason for this may be inferred as follows, although the detail is not clear: The particular compound (2) and the predetermined carbonate in the nonaqueous electrolytic solution will react together, and form an excellent protective film on the surface of a negative-electrode active material, thereby inhibiting side reactions and preventing the cycle degradation. In addition, an electrolytic solution containing both the particular compound (2) and the predetermined carbonate is considered to contribute to enhanced properties of the protective film in any way.

[II-3. Nonaqueous Solvent]

The nonaqueous electrolytic solution in accordance with the second aspect of the present invention can comprise any nonaqueous solvent that does not significantly impair the advantages of the present invention. The particular compounds (2) or the predetermined carbonates mentioned above can also be used as the nonaqueous solvent. The nonaqueous solvents including the particular compounds (2) or the predetermined carbonates may be used either alone or in any combination thereof at any proportion.

Examples of the nonaqueous solvents that are commonly used include such as cyclic carbonates, linear carbonates, linear and cyclic carboxylic esters, linear and cyclic ethers, phosphorus-containing organic solvents, and sulfur-containing organic solvents.

Nonlimiting examples of the cyclic carbonates that are commonly used include such as ethylene carbonate, propylene carbonate, and butylene carbonate. Among these preferred are ethylene carbonate and propylene carbonate having high dielectric constants, which facilitate dissolution of solutes and improve cycle characteristics of nonaqueous electrolyte secondary cells.

Examples of the linear carbonates that are commonly used include, but not limited to, such as dimethyl carbonate, ethyl methyl carbonate, diethyl carbonate, methyl n-propyl carbonate, ethyl n-propyl carbonate, and di-n-propyl carbonate. Among these preferred are dimethyl carbonate, ethyl methyl carbonate, diethyl carbonate, methyl n-propyl carbonate, and ethyl n-propyl carbonate, dimethyl carbonate, and especially preferred are ethyl methyl carbonate and diethyl carbonate because these carbonates ensures improved cycle characteristics of nonaqueous electrolyte secondary cells.

Examples of the linear carboxylic acid esters that are commonly used include, but not limited to, such as methyl acetate, ethyl acetate, n-propyl acetate, i-propyl acetate, n-butyl acetate, i-butyl acetate, t-butyl acetate, methyl propionate, ethyl propionate, n-propyl propionate, i-propyl propionate, n-butyl propionate, i-butyl propionate, and t-butyl propionate. Among these, more preferred are ethyl acetate, methyl propionate, and ethyl propionate.

Examples of the cyclic carboxylic acid esters that are commonly used include, but not limited to, such as γ-butyrolactone, γ-valerolactone, and δ-valerolactone. Among these, γ-butyrolactone is more preferred.

Examples of the linear ethers that are commonly used include, but not limited to, such as dimethoxymethane, dimethoxyethane, diethoxymethane, diethoxyethane, ethoxymethoxymethane, and ethoxymethoxyethane. Among these, dimethoxyethane and diethoxyethane are more preferred.

Examples of the cyclic ethers that are commonly used include, but not limited to, such as tetrahydrofuran and 2-methyltetrahydrofuran.

Examples of the phosphorus-containing organic solvents that are commonly used include, but not limited to, such as phosphate esters such as trimethyl phosphate, triethyl phosphate, and triphenyl phosphate; phosphite esters such as trimethyl phosphite, triethyl phosphite, and triphenyl phosphite; phosphine oxides such as trimethylphosphine oxide, triethylphosphine oxide, and triphenylphosphine oxide.

Examples of the sulfur-containing organic solvents that are commonly used include, but not limited to, such as ethylene sulfite, 1,4-propane sultone, 1,4-butane sultone, methyl methanesulfonate, busulfan, sulfolane, sulfolene, dimethyl sulfone, diphenyl sulfone, methyl phenyl sulfone, dibutyl disulfide, dicyclohexyl disulfide, tetramethylthiuram monosulfide, N,N-dimethylmethanesulfonamide, and N,N-diethylmethanesulfonamide.

Among these, the cyclic carbonates, i.e., ethylene carbonate and/or propylene carbonate is preferably used, and more preferably is used as a mixture with a linear carbonate.

In such combined use of the cyclic carbonates and the linear carbonates as the nonaqueous solvent, the suitable amount of the linear carbonate in the nonaqueous solvent in the nonaqueous electrolytic solution in accordance with the second aspect of the present invention is usually 30% by volume or more and preferably 50% by volume or more, and usually 95% by volume or less and preferably 90% by volume or less. The suitable amount of the cyclic carbonate in the nonaqueous solvent in the nonaqueous electrolytic solution in accordance with the second aspect of the present invention is usually 5% by volume or more and preferably 10% by volume or more, and usually 50% by volume or less and preferably 40% by volume or less. When containing the linear carbonate in a lower amount than this range, the nonaqueous electrolytic solution in accordance with the second aspect of the present invention may have an increased viscosity. When containing the linear carbonate in a higher amount than this range, the nonaqueous electrolytic solution may have a decreased degree of dissociation of the electrolyte, i.e., lithium salt, and then have a decreased electric conductivity.

[II-4. Electrolyte]

The nonaqueous electrolytic solution in accordance with the second aspect of the present invention may contain the same electrolytes for the nonaqueous electrolytic solution in accordance with the first aspect of the present invention.

[II-5. Additive]

Preferably, the nonaqueous electrolytic solution in accordance with the second aspect of the present invention contains various additives that do not significantly impair the advantages of the present invention. Any conventional known additive can be used either alone or in any combination thereof at any proportion. Examples of such additives include overcharge protection agents, and aids for improving capacity maintenance and cycle characteristics after high-temperature preservation.

Examples of the overcharge protection agents include such as aromatic compounds such as biphenyls, alkylbiphenyls, terphenyls, partially hydrogenated terphenyls, cyclohexylbenzene, t-butylbenzene, t-amylbenzene, diphenyl ether, and dibenzofuran; partially fluorinated aromatic compounds mentioned above such as 2-fluorobiphenyl, o-cyclohexylfluorobenzene, and p-cyclohexylfluorobenzene; and fluorine-containing anisoles such as 2,4-difluoroanisole, 2,5-difluoroanisole, and 2,6-difluoroanisole.

The overcharge protection agents may be used either alone or in any combination thereof at any proportion.

The nonaqueous electrolytic solution in accordance with the second aspect of the present invention may contain the overcharge protection agents in any concentration that does not significantly impair the advantages of the present invention, and the concentration of the overcharge protection agents is usually 0.1% by weight to 5% by weight based on the entire nonaqueous electrolytic solution. Incorporation of overcharge protection agents into a nonaqueous electrolytic solution is preferred because these agents can inhibit a nonaqueous electrolyte secondary cell from exploding and igniting even when the cell is overcharged, thereby enhancing the safety of the cell.

Examples of aids for improving capacity maintenance and cycle characteristics after high-temperature preservation include carbonate compounds such as vinylene carbonate, vinyl ethylene carbonate, fluoroethylene carbonate, difluoroethylene carbonate, 4-(trifluoromethyl)-ethylene carbonate, phenyl ethylene carbonate, erythritan carbonate, and spiro-bis-dimethylene carbonate; carboxylic anhydrides such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride, and phenylsuccinic anhydride; sulfur-containing compounds such as ethylene sulfite, 1,4-propane sultone, 1,4-butane sultone, methyl methanesulfonate, busulfan, sulfolane, sulfolene, dimethyl sulfone, diphenyl sulfone, methyl phenyl sulfone, dibutyl disulfide, dicyclohexyl disulfide, tetramethylthiuram monosulfide, N,N-dimethylmethanesulfonamide, and N,N-diethylmethanesulfonamide; nitrogen-containing compounds such as 1-methyl-2-pyrrolidinone, 1-methyl-2-piperidone, 4-methyl-2-oxazolidinone, 1,4-dimethyl-2-imidazolidinone, and N-methylsuccinimide; hydrocarbons such as heptane, octane, and cycloheptane, and fluorine-containing aromatic compounds such as fluorobenzene, difluorobenzene, and benzotrifluoride.

The aids may be used either alone or in any combination thereof at any proportion.

The nonaqueous electrolytic solution in accordance with the second aspect of the present invention can contain the aids in any concentration that does not significantly impair the advantages of the present invention, and the concentration of the aids is usually 0.1% by weight to 5% by weight based on the entire nonaqueous electrolytic solution.

[III. Nonaqueous Electrolytic Solution of Third Aspect]

The nonaqueous electrolytic solution in accordance with the third aspect of the present invention comprises at least one compound represented by the following formula (3) (hereinafter arbitrarily referred to as "particular compound (3)") in a nonaqueous solvent:

[Chemical Formula 9]

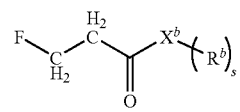

(3)

wherein $X^b$ represents oxygen or nitrogen; $R^b$ represents hydrogen, or substituted or unsubstituted alkyl, and s is one when $X^b$ represents oxygen or two when $X^b$ represents nitrogen. The nonaqueous electrolytic solution in accordance with the third aspect of the present invention typically contains an electrolyte, and may optionally contain a predetermined carbonate and any additive.

[III-1. Particular Compound (3)]

The particular compound (3) contained in the nonaqueous electrolytic solution in accordance with the third aspect of the present invention is represented by the formula (3).

$X^b$ in the formula (3) represents oxygen or nitrogen.

$R^b$ in the formula (3) represents hydrogen, or substituted or unsubstituted alkyl.

When $R^b$ is alkyl, the alkyl may be linear, branched, or cyclic. Since branched alkyls may have high degradability, the alkyl is preferably linear that does not have branched-chain.

When $R^b$ is substituted alkyl, the substituents may be any group that does not significantly impair the advantages of the present invention. Examples of the group include fluorine, alkoxy, alkoxycarboxyl, and alkylcarboxyl. These substituents may be used either alone or in any combination thereof at any proportion.

Unless significantly impairing the advantages of the present invention, the carbon number of $R^b$ may also be any number. Since the particular compound (3) with $R^b$ having a significantly high molecular weight may not exhibit advantages comparable to the amount of the compound (3) contained in the nonaqueous electrolytic solution in accordance with the third aspect of the present invention, the number is preferably ten or less, more preferably five or less, and most preferably three or less.

In the formula (3), s represents one or two. Particularly, is one when $X^b$ represents oxygen or two when $X^b$ represents nitrogen. When s is two, $R^b$ in the formula (3) may be the same kind or different.

In general, preferred $R^b$ is unsubstituted alkyl or alkyl substituted by fluorine alone since it can enhance the stability as an organic substance of the particular compound (3) and the stability of a protective layer formed when the compound (3) is contained in an electrolytic solution.

Specific examples of $R^b$ include such as hydrogen atom, methyl, fluoromethyl, difluoromethyl, ethyl, 2-fluoroethyl, 2,2-difluoroethyl, 2,2,2-trifluoroethyl, n-propyl, 3-fluoro-n-propyl, 3,3-difluoro-n-propyl, 3,3,3-trifluoro-n-propyl, i-propyl, and 1,1,1,3,3,3-hexafluoro-i-propyl.

Among these preferred are methyl, ethyl, 2-fluoroethyl, 2,2-difluoroethyl, 2,2,2-trifluoroethyl, n-propyl, and 3-fluoro-n-propyl, and most preferred are methyl and ethyl, which are readily available due to production with ease.

Specific examples of the particular compounds (3) include such as methyl-3-fluoropropionate, ethyl-3-fluoropropionate, 2-fluoroethyl-3-fluoropropionate, 2,2-difluoroethyl-3-fluoropropionate, 2,2,2-trifluoroethyl-3-fluoropropionate, n-propyl-3-fluoropropionate, 3-fluoro-n-propyl-3-fluoropropionate, 3-fluoropropionamide, N-methyl-3-fluoropropionamide, N,N-dimethyl-3-fluoropropionamide, N-ethyl-3-fluoropropionamide, N,N-diethyl-3-fluoropropionamide, N-fluoromethyl-3-fluoropropionamide, N,N-bis(fluoromethyl)-3-fluoropropionamide, N-(2-fluoroethyl)-3-fluoropropionamide, N,N-bis(2-fluoroethyl)-3-fluoropropionamide, N-(2,2-difluoroethyl)-3-fluoropropionamide, N,N-bis(2,2-difluoroethyl)-3-fluoropropionamide, N-(2,2,2-trifluoroethyl)-3-fluoropropionamide, N,N-bis(2,2,2-trifluoroethyl)-3-fluoropropionamide, N-n-propyl-3-fluoropropionamide, N,N-di-n-propyl-3-fluoropropionamide, N-(3-fluoro-n-propyl)-3-fluoropropionamide, and N,N-bis(3-fluoro-n-propyl)-3-fluoropropionamide.

Among these preferred are methyl-3-fluoropropionate, ethyl-3-fluoropropionate, 2-fluoroethyl-3-fluoropropionate, 2,2,2-trifluoroethyl-3-fluoropropionate, 3-fluoropropionamide, methyl-3-fluoropropionamide, and ethyl-3-fluoropropionamide.

When contained in the nonaqueous electrolytic solution in accordance with the third aspect of the present invention, the particular compounds (3) may be used either alone or in any combination thereof at any proportion.

When contained in the nonaqueous electrolytic solution in accordance with the third aspect of the present invention, the amount of the particular compound (3) is usually 0.01% by weight or more and preferably 0.1% by weight or more, and usually 10% by volume or less, and preferably 5% by volume or less based on the nonaqueous electrolytic solution. Below the lower limit, a nonaqueous electrolyte secondary cell containing the nonaqueous electrolytic solution in accordance with the third aspect of the present invention will not exhibit sufficiently enhanced cycle characteristics. Above the upper limit, an increased reactivity in the nonaqueous electrolytic solution will impair the cell characteristics of a nonaqueous electrolyte secondary cell.

When a nonaqueous electrolytic solution containing the particular compound (3) is contained in a nonaqueous electrolyte secondary cell, charge and discharge cycle characteristics of the cell can be enhanced. The reason for this may be inferred as follows, although the detail is not clear: When a nonaqueous electrolytic solution containing the particular compound (3) is contained in a nonaqueous electrolyte secondary cell, the particular compound (3) will react in the cell to form an excellent protective layer on the surface of a negative-electrode active material, thereby inhibiting side reactions and preventing the cycle degradation. In this case, both hydrogen and fluorine are present on at least one terminal carbon atom in the particular compound (3) represented by the formula (3), and it is considered to contribute to enhanced properties of the protective film in any way.

Any known method can be used without limitation for producing the particular compound (3).

[III-2. Predetermined Carbonate]

Preferably, the nonaqueous electrolytic solution in accordance with the third aspect of the present invention further comprises a predetermined carbonate. The predetermined carbonate in the nonaqueous electrolytic solution in accordance with the third aspect of the present invention has at least one of an unsaturated bond and a halogen atom. That is, the predetermined carbonate in the nonaqueous electrolytic solution in accordance with the third aspect of the present invention may have only an unsaturated bond or only a halogen atom, or may have the both.

Among the predetermined carbonates other than the particular compounds (3), any predetermined carbonate having an unsaturated bond (arbitrarily abbreviated as "predetermined unsaturated carbonate") may be used without limitation with the proviso that the predetermined carbonate has a carbon-carbon unsaturated bond, i.e. a carbon-carbon double bond or triple bond. The predetermined unsaturated carbonates having such unsaturated bonds also include carbonates having aromatic rings.

Examples of the predetermined unsaturated carbonate include vinylene carbonate derivatives, substituted ethylene carbonate derivatives by substituents with aromatic rings or carbon-carbon unsaturated bonds, phenyl carbonates, vinyl carbonates, and allyl carbonates.

Specific examples of vinylene carbonate derivatives include vinylene carbonate, methyl vinylene carbonate, 4,5-dimethyl vinylene carbonate, phenyl vinylene carbonate, and 4,5-diphenyl vinylene carbonate.

Specific examples of substituted ethylene carbonate derivatives by substituents with aromatic rings or carbon-carbon unsaturated bonds include such as vinyl ethylene carbonate, 4,5-divinyl ethylene carbonate, phenyl ethylene carbonate, and 4,5-diphenyl ethylene carbonate.

Specific examples of phenyl carbonates include such as diphenyl carbonate, ethyl phenyl carbonate, methyl phenyl carbonate, and t-butyl phenyl carbonate.

Specific examples of vinyl carbonates include such as divinyl carbonate and methyl vinyl carbonate.

Specific examples of allyl carbonates include such as diallyl carbonate and allyl methyl carbonate.

Among these predetermined unsaturated carbonates preferred as the predetermined carbonate are the vinylene carbonate derivatives and the substituted ethylene carbonate derivatives by substituents with aromatic rings or carbon-carbon unsaturated bonds. Particularly preferred are vinylene carbonate, 4,5-diphenyl vinylene carbonate, 4,5-dimethyl vinylene carbonate, and vinyl ethylene carbonate because these can form stable surface protective films.

Among the predetermined carbonate having halogen atoms (arbitrarily abbreviated as "predetermined halogenated carbonate"), any halogenated carbonate can be used without limitation.

Specific examples of the halogen atom contained in the predetermined halogenated carbonate include fluorine, chlorine, bromine, and iodine atoms. Among these preferred is a fluorine or chlorine atom and in particular, a fluorine atom.

The number of the halogen atoms in the predetermined halogenated carbonate may be at least one without limitation, but usually six or less, and preferably four or less. When the predetermined halogenated carbonate has multiple halogen atoms, they may be the same or different.

Examples of the predetermined halogenated carbonate include ethylene carbonate derivatives, dimethyl carbonate derivatives, ethyl methyl carbonate derivatives, and diethyl carbonate derivatives.

Specific examples of the ethylene carbonate derivatives include such as fluoroethylene carbonate, chloroethylene carbonate, 4,4-difluoroethylene carbonate, 4,5-difluoroethylene carbonate, 4,4-dichloroethylene carbonate, 4,5-dichloroethylene carbonate, 4-fluoro-4-methylethylene carbonate, 4-chloro-4-methylethylene carbonate, 4,5-difluoro-4-methylethylene carbonate, 4,5-dichloro-4-methylethylene carbonate, 4-fluoro-5-methylethylene carbonate, 4-chloro-5-methylethylene carbonate, 4,4-difluoro-5-methylethylene carbonate, 4,4-dichloro-5-methylethylene carbonate, 4-(fluoromethyl)-ethylene carbonate, 4-(chloromethyl)-ethylene carbonate, 4-(difluoromethyl)-ethylene carbonate, 4-(dichloromethyl)-ethylene carbonate, 4-(trifluoromethyl)-ethylene carbonate, 4-(trichloromethyl)-ethylene carbonate, 4-(fluoromethyl)-4-fluoroethylene carbonate, 4-(chloromethyl)-4-chloroethylene carbonate, 4-(fluoromethyl)-5-fluoroethylene carbonate, 4-(chloromethyl)-5-chloroethylene carbonate, 4-fluoro-4,5-dimethylethylene carbonate, 4-chloro-4,5-dimethylethylene carbonate, 4,5-difluoro-4,5-dimethylethylene carbonate, 4,5-dichloro-4,5-dimethylethylene carbonate, 4,4-difluoro-5,5-dimethylethylene carbonate, and 4,4-dichloro-5,5-dimethylethylene carbonate.

Specific examples of the dimethyl carbonate derivatives include such as fluoromethyl methyl carbonate, difluoromethyl methyl carbonate, trifluoromethyl methyl carbonate, bis(fluoromethyl)carbonate, bis(difluoro)methyl carbonate, bis(trifluoro)methyl carbonate, chloromethyl methyl carbonate, dichloromethyl methyl carbonate, trichloromethyl methyl carbonate, bis(chloromethyl)carbonate, bis(dichloro) methyl carbonate, and bis(trichloro)methyl carbonate.

Specific examples of the ethyl methyl carbonate derivatives include such as 2-fluoroethyl methyl carbonate, ethyl fluoromethyl carbonate, 2-fluoroethyl fluoromethyl carbonate, 2,2-difluoroethyl methyl carbonate, ethyl difluoromethyl carbonate, 2,2,2-trifluoroethyl methyl carbonate, 2-fluoroethyl difluoromethyl carbonate, ethyl trifluoromethyl carbonate, 2-chloroethyl methyl carbonate, ethyl chloromethyl carbonate, 2,2-dichloroethyl methyl carbonate, 2-chloroethyl chloromethyl carbonate, ethyl dichloromethyl carbonate, 2,2,2-trichloroethyl methyl carbonate, 2,2-dichloroethyl chloromethyl carbonate, 2-chloroethyl dichloromethyl carbonate, and ethyl trichloromethyl carbonate.

Specific examples of the diethyl carbonate derivatives include such as ethyl-(2-fluoroethyl)carbonate, bis(2-fluoroethyl)carbonate, 2,2-difluoroethyl ethyl carbonate, 2,2-difluoroethyl-2'-fluoroethyl carbonate, bis(2,2-difluoroethyl) carbonate, ethyl-(2,2,2-trifluoroethyl)carbonate, 2,2,2-trifluoroethyl-2'-fluoroethyl carbonate, 2,2,2-trifluoroethyl-2',2'-difluoroethyl carbonate, bis(2,2,2-trifluoroethyl) carbonate, ethyl-(2-chloroethyl)carbonate, ethyl-(2,2-dichloroethyl)carbonate, bis(2-chloroethyl)carbonate, ethyl-(2,2,2-trichloroethyl)carbonate, 2,2-dichloroethyl-2'-chloroethyl carbonate, bis(2,2-dichloroethyl)carbonate, 2,2,2-trichloroethyl-2'-chloroethyl carbonate, 2,2,2-trichloroethyl-2',2'-dichloroethyl carbonate, and bis(2,2,2-trichloroethyl)carbonate.

Among these predetermined halogenated carbonates, preferred are carbonates having fluorine atoms, and more preferred are ethylene carbonate derivatives having fluorine atoms. In particular, fluoroethylene carbonate, 4-(fluoromethyl)-ethylene carbonate, 4,4-difluoroethylene carbonate, and 4,5-difluoroethylene carbonate are preferably used because they can form surface protective films.

In addition, the predetermined carbonate can have both an unsaturated bond and a halogen atom (arbitrarily abbreviated as "predetermined halogenated unsaturated carbonate"). The predetermined halogenated unsaturated carbonate may be any halogenated unsaturated carbonate that does not significantly impair the advantages of the present invention.

Examples of the predetermined halogenated unsaturated carbonate include such as vinylene carbonate derivatives, substituted ethylene carbonate derivatives by substituents with aromatic rings or carbon-carbon unsaturated bonds, phenyl carbonates, vinyl carbonates, and allyl carbonates.

Specific examples of the vinylene carbonate derivatives include such as fluorovinylene carbonate, 4-fluoro-5-methylvinylene carbonate, 4-fluoro-5-phenylvinylene carbonate, chlorovinylene carbonate, 4-chloro-5-methylvinylene carbonate, and 4-chloro-5-phenylvinylene carbonate.

Specific examples of the substituted ethylene carbonate derivatives by substituents with aromatic rings or carbon-carbon unsaturated bonds include 4-fluoro-4-vinylethylene carbonate, 4-fluoro-5-vinylethylene carbonate, 4,4-difluoro-4-vinylethylene carbonate, 4,5-difluoro-4-vinylethylene carbonate, 4-chloro-5-vinylethylene carbonate, 4,4-dichloro-4-vinylethylene carbonate, 4,5-dichloro-4-vinylethylene carbonate, 4-fluoro-4,5-divinylethylene carbonate, 4,5-difluoro-4,5-divinylethylene carbonate, 4-chloro-4,5-divinylethylene carbonate, 4,5-dichloro-4,5-divinylethylene carbonate, 4-fluoro-4-phenylethylene carbonate, 4-fluoro-5-phenylethylene carbonate, 4,4-difluoro-5-phenylethylene carbonate, 4,5-difluoro-4-phenylethylene carbonate, 4-chloro-4-phenylethylene carbonate, 4-chloro-5-phenylethylene carbonate, 4,4-dichloro-5-phenylethylene carbonate, 4,5-dichloro-4-phenylethylene carbonate, 4,5-difluoro-4,5-diphenylethylene carbonate, and 4,5-dichloro-4,5-diphenylethylene carbonate.

Specific examples of the phenyl carbonates include such as fluoromethyl phenyl carbonate, 2-fluoroethyl phenyl carbonate, 2,2-difluoroethyl phenyl carbonate, 2,2,2-trifluoroethyl phenyl carbonate, chloromethyl phenyl carbonate, 2-chloroethyl phenyl carbonate, 2,2-dichloroethyl phenyl carbonate, and 2,2,2-trichloroethyl phenyl carbonate.

Specific examples of the vinyl carbonates include such as fluoromethyl vinyl carbonate, 2-fluoroethyl vinyl carbonate, 2,2-difluoroethyl vinyl carbonate, 2,2,2-trifluoroethyl vinyl carbonate, chloromethyl vinyl carbonate, 2-chloroethyl vinyl carbonate, 2,2-dichloroethyl vinyl carbonate, and 2,2,2-trichloroethyl vinyl carbonate.

Specific examples of the allyl carbonates include such as fluoromethyl allyl carbonate, 2-fluoroethyl allyl carbonate, 2,2-difluoroethyl allyl carbonate, 2,2,2-trifluoroethyl allyl carbonate, chloromethyl allyl carbonate, 2-chloroethyl allyl carbonate, 2,2-dichloroethyl allyl carbonate, and 2,2,2-trichloroethyl allyl carbonate.

Among the exemplary predetermined halogenated unsaturated carbonates mentioned above, it is especially preferred to use at least one selected from the group consisting of vinylene carbonate, vinyl ethylene carbonate, fluoroethylene carbonate, difluoroethylene carbonates, and derivatives thereof as the predetermined carbonate because of high effects thereof when used alone. Among the difluoroethylene carbonates, especially preferred is 4,5-difluoroethylene carbonate.

The predetermined carbonate may have any molecular weight that does not significantly impair the advantages of the present invention, and the molecular weight is usually 50 or more and preferably 80 or more, and usually 250 or less and preferably 150 or less. At a higher molecular weight of the predetermined carbonate, the solubility of the carbonate in a nonaqueous electrolytic solution may be too poor to exhibit the advantages of the present invention sufficiently.

The predetermined carbonates can be prepared by any known method without limitation.

The predetermined carbonates as described above may also be used either alone or in any combination thereof at any proportion in the nonaqueous electrolytic solution in accordance with the third aspect of the present invention.

The predetermined carbonate may be used in any amount in the nonaqueous electrolytic solution in accordance with the third aspect of the present invention without limitation within the scope that does not significantly impair the advantages of the present invention, and the amount of the predetermined carbonate is usually 0.01% by weight or more, preferably 0.1% by weight or more, and more preferably 0.3% by weight or more, and usually 70% by weight or less, preferably 50% by weight or less, and more preferably 40% by weight or less of the nonaqueous electrolytic solution in accordance with the third aspect of the present invention. Below the lower limit, a nonaqueous electrolyte secondary cell containing the nonaqueous electrolytic solution in accordance with the third aspect of the present invention may not exhibit sufficiently enhanced cycle characteristics. At a higher proportion of the predetermined carbonate, a nonaqueous electrolyte secondary cell containing the nonaqueous electrolytic solution in accordance with the third aspect of the present invention tends to impair its high-temperature preservation characteristics and trickle charge characteristics, and particularly may increase the amount of gas generation and decrease its discharge capacity maintenance rate.

In the nonaqueous electrolytic solution in accordance with the third aspect of the present invention, the particular compound (3) and the predetermined carbonate may be used in any ratio. The ratio of "the amount of the particular compound (3) to the amount of the predetermined carbonate" is usually 0.0001 or more, preferably 0.001 or more, and more preferably 0.01 or more, and usually 1000 or less, preferably 100 or less, and more preferably 10 or less. At a ratio that is lower or higher than this range, synergistic effects by the combination may be not exhibited.

When a nonaqueous electrolytic solution containing both the particular compound (3) and the predetermined carbonate is contained in a nonaqueous electrolyte secondary cell, charge and discharge cycle characteristics of the cell can be enhanced. The reason for this may be inferred as follows, although the detail is not clear: The particular compound (3) and the predetermined carbonate in the nonaqueous electrolytic solution will react together, and form an excellent protective film on the surface of a negative-electrode active material, thereby inhibiting side reactions and preventing the cycle degradation. In addition, an electrolytic solution containing both the particular compound (3) and the predetermined carbonate is considered to contribute to enhanced properties of the protective film in any way.

[III-3. Nonaqueous Solvent]

The nonaqueous electrolytic solution in accordance with the third aspect of the present invention can comprise any nonaqueous solvent that does not significantly impair the advantages of the present invention. The particular compounds (3) or the predetermined carbonates mentioned above can also be used as the nonaqueous solvent. The nonaqueous solvents including the particular compounds (3) or the predetermined carbonates may be used either alone or in any combination thereof at any proportion.

Examples of the nonaqueous solvents that are commonly used include such as cyclic carbonates, linear carbonates, linear and cyclic carboxylic esters, linear and cyclic ethers, phosphorus-containing organic solvents, and sulfur-containing organic solvents.

Nonlimiting examples of the cyclic carbonates that are commonly used include such as ethylene carbonate, propylene carbonate, and butylene carbonate. Among these preferred are ethylene carbonate and propylene carbonate having high dielectric constants, which facilitate dissolution of solutes and improve cycle characteristics of nonaqueous electrolyte secondary cells.

Examples of the linear carbonates that are commonly used include, but not limited to, such as dimethyl carbonate, ethyl methyl carbonate, diethyl carbonate, methyl n-propyl carbonate, ethyl n-propyl carbonate, and di-n-propyl carbonate. Among these preferred are dimethyl carbonate, ethyl methyl carbonate, diethyl carbonate, methyl n-propyl carbonate, and ethyl n-propyl carbonate, and especially preferred are dimethyl carbonate, ethyl methyl carbonate and diethyl carbonate because these carbonates ensures improved cycle characteristics of nonaqueous electrolyte secondary cells.

Examples of the linear carboxylic acid esters that are commonly used include, but not limited to, such as methyl acetate, ethyl acetate, n-propyl acetate, i-propyl acetate, n-butyl acetate, i-butyl acetate, t-butyl acetate, methyl propionate, ethyl propionate, n-propyl propionate, i-propyl propionate, n-butyl propionate, i-butyl propionate, and t-butyl propionate. Among these, more preferred are ethyl acetate, methyl propionate, and ethyl propionate.

Examples of the cyclic carboxylic acid esters that are commonly used include, but not limited to, such as γ-butyrolactone, γ-valerolactone, and δ-valerolactone. Among these, γ-butyrolactone is more preferred.

Examples of the linear ethers that are commonly used include, but not limited to, such as dimethoxymethane, dimethoxyethane, diethoxymethane, diethoxyethane, ethoxymethoxymethane, and ethoxymethoxyethane. Among these, dimethoxyethane and diethoxyethane are more preferred.

Examples of the cyclic ethers that are commonly used include, but not limited to, such as tetrahydrofuran and 2-methyltetrahydrofuran.

Examples of the phosphorus-containing organic solvents that are commonly used include, but not limited to, such as phosphate esters such as trimethyl phosphate, triethyl phosphate, and triphenyl phosphate; phosphite esters such as trimethyl phosphite, triethyl phosphite, and triphenyl phosphite; phosphine oxides such as trimethylphosphine oxide, triethylphosphine oxide, and triphenylphosphine oxide.

Examples of the sulfur-containing organic solvents that are commonly used include, but not limited to, such as ethylene sulfite, 1,4-propane sultone, 1,4-butane sultone, methyl methanesulfonate, busulfan, sulfolane, sulfolene, dimethyl sulfone, diphenyl sulfone, methyl phenyl sulfone, dibutyl disulfide, dicyclohexyl disulfide, tetramethylthiuram monosulfide, N,N-dimethylmethanesulfonamide, and N,N-diethylmethanesulfonamide.

Among these, the cyclic carbonates, i.e., ethylene carbonate and/or propylene carbonate is preferably used, and more preferably is used as a mixture with a linear carbonate.

In such combined use of the cyclic carbonates and the linear carbonates as the nonaqueous solvent, the suitable amount of the linear carbonate in the nonaqueous solvent in the nonaqueous electrolytic solution in accordance with the third aspect of the present invention is usually 30% by volume or more and preferably 50% by volume or more, and usually 95% by volume or less and preferably 90% by volume or less. The suitable amount of the cyclic carbonate in the nonaqueous solvent in the nonaqueous electrolytic solution in accordance with the third aspect of the present invention is usually 5% by volume or more and preferably 10% by volume or more, and usually 50% by volume or less and preferably 40% by volume or less. When containing the linear carbonate in a lower amount than this range, the nonaqueous electrolytic solution in accordance with the third aspect of the present invention may have an increased viscosity. When containing the linear carbonate in a higher amount than this range, the nonaqueous electrolytic solution may have a decreased degree of dissociation of the electrolyte, i.e., lithium salt, and then have a decreased electric conductivity.

[III-4. Electrolyte]

The nonaqueous electrolytic solution in accordance with the third aspect of the present invention may contain the same electrolytes for the nonaqueous electrolytic solution in accordance with the first aspect of the present invention.

[III-5. Additive]

Preferably, the nonaqueous electrolytic solution in accordance with the third aspect of the present invention contains various additives that do not significantly impair the advantages of the present invention. Any conventional known additive can be used either alone or in any combination thereof at any proportion. Examples of such additives include overcharge protection agents, and aids for improving capacity maintenance and cycle characteristics after high-temperature preservation.

Examples of the overcharge protection agents include aromatic compounds such as biphenyls, alkylbiphenyls, terphenyls, partially hydrogenated terphenyls, cyclohexylbenzene, t-butylbenzene, t-amylbenzene, diphenyl ether, and dibenzofuran; partially fluorinated aromatic compounds mentioned above such as 2-fluorobiphenyl, o-cyclohexylfluorobenzene, and p-cyclohexylfluorobenzene; and fluorine-containing anisoles such as 2,4-difluoroanisole, 2,5-difluoroanisole, and 2,6-difluoroanisole.

The overcharge protection agents may be used either alone or in any combination thereof at any proportion.

The nonaqueous electrolytic solution in accordance with the third aspect of the present invention may contain the overcharge protection agents in any concentration that does not significantly impair the advantages of the present invention, and the concentration of the overcharge protection agents is usually 0.1% by weight to 5% by weight based on the entire nonaqueous electrolytic solution. Incorporation of overcharge protection agents into a nonaqueous electrolytic solution is preferred because these agents can inhibit a nonaqueous electrolyte secondary cell from exploding and igniting even when the cell is overcharged, thereby enhancing the safety of the cell.

Examples of aids for improving capacity maintenance and cycle characteristics after high-temperature preservation include carbonate compounds such as vinylene carbonate, vinyl ethylene carbonate, fluoroethylene carbonate, difluoroethylene carbonate, 4-(trifluoromethyl)-ethylene carbonate, phenyl ethylene carbonate, erythritan carbonate, and spirobis-dimethylene carbonate; carboxylic anhydrides such as succinic anhydride, glutaric anhydride, maleic anhydride, citraconic anhydride, glutaconic anhydride, itaconic anhydride, diglycolic anhydride, cyclohexanedicarboxylic anhydride, cyclopentanetetracarboxylic dianhydride, and phenylsuccinic anhydride; sulfur-containing compounds such as ethylene sulfite, 1,4-propane sultone, 1,4-butane sultone, methyl methanesulfonate, busulfan, sulfolane, sulfolene, dimethyl sulfone, diphenyl sulfone, methyl phenyl sulfone, dibutyl disulfide, dicyclohexyl disulfide, tetramethylthiuram monosulfide, N,N-dimethylmethanesulfonamide, and N,N-diethylmethanesulfonamide; nitrogen-containing compounds such as 1-methyl-2-pyrrolidinone, 1-methyl-2-piperidone, 4-methyl-2-oxazolidinone, 1,4-dimethyl-2-imidazolidinone, and N-methylsuccinimide; hydrocarbons such as heptane, octane, and cycloheptane, and fluorine-containing aromatic compounds such as fluorobenzene, difluorobenzene, and benzotrifluoride.

The aids may be used either alone or in any combination thereof at any proportion.

The nonaqueous electrolytic solution in accordance with the third aspect of the present invention can contain the aids in any concentration that does not significantly impair the advantages of the present invention, and the concentration of the aids is usually 0.1% by weight to 5% by weight based on the entire nonaqueous electrolytic solution.

[IV. Nonaqueous Electrolyte Secondary Cell]

A nonaqueous electrolyte secondary cell of the present invention comprises a negative electrode and a positive electrode capable of occluding and discharging lithium ions, and the above nonaqueous electrolytic solution of the present invention.

Except for the nonaqueous electrolytic solution, this nonaqueous electrolyte secondary cell of the present invention may have any constitution similar to those of known nonaqueous electrolyte secondary cells. Typically, the nonaqueous electrolyte secondary cell has a positive electrode and a negative electrode that are laminated separated by a porous membrane (a separator) impregnated with the nonaqueous electrolytic solution of the present invention and are accommodated in a case (an external housing).

[IV-1. Nonaqueous Electrolytic Solution]

At least any one of the nonaqueous electrolytic solutions of the first, second, and third aspects of the present invention containing at least any one of the above particular linear carbonate, particular compound (2), and particular compound (3) in a nonaqueous solvent is used as the nonaqueous electrolytic solution.

[IV-2. Negative Electrode]

Unless impairing the advantages of the present invention, any negative electrode capable of occluding and discharging lithium ions may be used for the nonaqueous electrolyte secondary cell of the present invention. Typically, the negative electrodes have negative-electrode active materials supported on a current collector.

Any negative-electrode active material can be used, for example carbonous materials, metallic materials, metallic lithium, and lithium alloy capable of occluding and discharging lithium. The negative-electrode active materials may be used either alone or in any combination thereof at any proportion.

Especially preferred are carbonous materials, alloys consisting of lithium and at least one metal capable of occluding and discharging lithium, and composite compound materials such as borides, oxides, nitrides, sulfides and phosphides of these metals.

The negative-electrode active material may be composed of any carbonous material, and preferred are, for example, graphite and graphite coated with amorphous carbon relative to graphite.

The uncoated graphite has a d-value (interplanar spacing) between the lattice planes (002) of usually 0.335 nm or more, and usually 0.338 nm or less and preferably 0.337 nm or less, as determined by X-ray diffractometry according to a method by Gakushin (the Japan Society for the Promotion of Science).

The graphite has also a crystallite size (Lc) of usually 30 nm or more, preferably 50 nm or more, and more preferably 100 nm or more, as determined by X-ray diffractometry according to the Gakushin method.

The uncoated graphite has also an ash content of usually 1% by weight or less, preferably 0.5% by weight or less, and more preferably 0.1% by weight or less.

The graphite coated with amorphous carbon preferably contains graphite having a d-value between the lattice planes (002) by X-ray diffractometry of usually 0.335 nm to 0.338 nm as the core material which is coated with a carbonous material having a higher d-value than that of the core material. More preferably, the ratio by weight of the core material to the carbonous material by weight ranges typically from 99/1 to 80/20. This can make negative electrodes which have a high capacity and barely react with a nonaqueous electrolytic solution.

The carbonous material has any particle size within the scope that does not impair the advantages of the present invention, and the size is usually 1 μm or more, preferably 3 μm or more, more preferably 5 μm or more, and even more preferably 7 μm or more in median diameter as determined by a laser diffraction-scattering method. The upper limit of the particle size is usually 100 μm or less, preferably 50 μm or less, more preferably 40 μm or less, and even more preferably 30 μm or less. Below the lower limit, the specific surface area of the carbonous material may be too large; above the upper limit, the specific surface area may be too small.

The carbonous material that does not significantly impair the advantages of the present invention has any specific surface area as determined by the BET method, and the area is usually 0.3 m$^2$/g or more, preferably 0.5 m$^2$/g or more, more preferably 0.7 m$^2$/g or more, and even more preferably 0.8 m$^2$/g or more. The upper limit of the area is usually 25.0 m$^2$/g or less, preferably 20.0 m$^2$/g or less, more preferably 15.0 m$^2$/g or less, and even more preferably 10.0 m$^2$/g or less. Below the lower limit, the carbonous material may fail to have a sufficient area to intercalate and deintercalate lithium ions; above the upper limit, the material may be too reactive with an electrolytic solution.

When analyzed for R-value ($=I_B/I_A$) which is given by the ratio of the peak intensity $I_A$ of a peak $P_A$ in the range between 1570 cm$^{-1}$ and 1620 cm$^{-1}$ to the peak intensity $I_B$ of a peak $P_B$ in the range between 1300 cm$^{-1}$ and 1400 cm$^{-1}$ of a Raman spectrum obtained by argon ion laser light, carbonous materials typically having a R-value ranging from 0.01 to 0.7 are preferred because these materials provides excellent cell characteristics.

In connection with this, when analyzed for the half width of a peak in the range between 1570 cm$^{-1}$ and 1620 cm$^{-1}$ of the Raman spectrum obtained by the argon ion laser light, carbonous materials usually having a peak width of 26 cm$^{-1}$ or less and preferably 25 cm$^{-1}$ or less because these materials provides excellent cell characteristics.

When alloys consisting of lithium and at least one metal capable of occluding and discharging lithium, or composite compound materials such as borides, oxides, nitrides, sulfides and phosphides of these metals are used as negative-electrode active materials, these alloys or composite compound materials may contain several metal elements, or composite compounds thereof. For example, these metallic alloys, or composite compounds such as borides, oxides, nitrides, sulfides and phosphides of these alloys may be further complicatedly chemically bound.

Among negative-electrode active materials consisting of these alloys or composite compound materials, preferred are those containing Si, Sn, or Pb, and more preferred are those containing Si or Sn because nonaqueous electrolyte secondary cells containing the materials will have a higher capacity per unit weight of the negative electrode.

Unless significantly impairing the advantages of the present invention, any known current collector can be used for a negative electrode. The current collectors can used either alone or in any combination thereof at any proportion.

Nonlimiting examples of the current collector materials for a negative electrode that are commonly used include such as steel, copper alloy, nickel, nickel alloy, and stainless steel. Among these preferred is copper foil due to allowing easy processing to a thin film and cost.

Furthermore, it is preferred to roughen a surface of the current collector in advance for improvement in binding efficiency between the collector and an active material layer to be formed on the surface. Examples of the surface-roughening methods include such as blasting, rolling with rough rolls; mechanical polishing the surface of the current collector with, for example, fabric coated with abrasive particles, grindstones, emery wheels, and wire brushes having steel wire; electropolishing; and chemical polishing.

Perforated collectors such as expanded metal and punching metal can be used for reduction in the weight of a current collector to increase an energy density per weight of a nonaqueous electrolyte cell. The weight of this type of collector can be varied at discretion by changing in its opening ratio. When active material layers are formed on both sides of this type of collector, the layers will barely be delaminated due to the rivet effect caused by these holes. However significantly high opening ratios of the collector will reduce the contact area between the active material layers and the collector, so that the adhesive strength may be decreased.

The thickness of the current collector is usually 1 μm or more and preferably 5 μm or more, and usually 100 μm or less and preferably 50 μm or less. A nonaqueous electrolyte secondary cell containing a significantly thick current collector may reduce its overall capacity exceedingly. On the other hand, significantly thin current collectors may be difficult to handle.

Any conventional method can be used without limitation for producing the negative electrode.

An example of such methods for producing the negative electrode involves adding additives such as a conductive material, binder, thickener, filler, and solvent to the negative-electrode active material to make slurry, applying this slurry on the current collector, pressing it to densify after drying, and forming a negative-electrode active material layer.

In this method, the slurry is made by adding a binder, thickener, filler, and solvent to the negative-electrode material. As used herein, the phrase "negative-electrode material" is defined as a combined material of negative-electrode active material and conductive material.

The amount of the negative-electrode active material is usually 70 parts by weight or more and preferably 75 parts by weight or more, and usually 97 parts by weight or less and preferably 95 parts by weight or less based on 100 parts by weight of the negative-electrode materials. Below the lower limit, the capacity of the negative electrode may be insufficient; whereas, above the upper limit, the strength of the negative electrode may be insufficient due to relative lack of the binder.

Nonlimiting examples of the conductive materials include metallic materials such as copper and nickel; and carbonous materials such as black lead or graphite, and carbon black. Especially preferred are carbonous materials because they serve as conductive materials as well as active materials. The conductive materials may be used either alone or in any combination thereof at any proportion.

The conductive materials may be used in any amount, but the amount is usually 3 parts by weight or more and preferably 5 parts by weight or more, and usually 30 parts by weight or less and preferably 25 parts by weight or less based on 100 parts by weight of the negative-electrode materials. Below the lower limit, the conductivity may be insufficient; whereas, above the upper limit, the cell capacity and strength may be insufficient due to relative lack of the negative-electrode active material.

Any material safe against solvents that are used in manufacture of electrodes and electrolytic solutions can be used as a binder. Examples include fluororesins such as polyvinylidene fluoride and polytetrafluoroethylene; polyolefins such as polyethylene and polypropylene; unsaturated polymers and copolymers thereof such as styrene/butadiene rubber, isoprene rubber, and butadiene rubber; and acrylic polymers and copolymers thereof such as ethylene-acrylic acid copolymer and ethylene-methacrylic acid copolymer. The binders may be used either alone or in any combination thereof at any proportion.

The binders may be used in any amount, but the amount is usually 0.5 part by weight or more and preferably 1 part by weight or more, and usually 10 parts by weight or less and preferably 8 parts by weight or less based on 100 parts by weight of the negative-electrode materials. Below the lower limit, the strength of the negative electrode may be insufficient; whereas above the upper limit, the cell capacity and conductivity may be insufficient due to relative lack of the negative-electrode active material.

Examples of the thickeners include such as carboxymethyl cellulose, methyl cellulose, hydroxymethyl cellulose, ethyl cellulose, polyvinyl alcohol, oxidized starch, phosphorylated starch, and caseins. The thickeners may be used either alone or in any combination thereof at any proportion.

The thickeners may be used in any amount, but the mount is usually 0.5% by weight to 5% by weight in the negative-electrode active material layers.

Examples of the fillers include lauric acid derivatives, for example, TWIN20 (trade mark). The fillers may be used either alone or in any combination thereof at any proportion.

The fillers may be used in any amount, but the amount is usually 0.5% by weight to 5% by weight in the negative-electrode active material layers.

When the slurry is prepared, any solvent can be used and include water, NMP (N-methylpyrrolidone), and DMF (N,N-dimethylformamide).

The slurry is subsequently applied to the current collector, and pressed after drying to form a negative-electrode active material layer. After drying and pressing, the negative-electrode active material layer may have any density, but the density is typically 1.0 g/cm$^3$ or more.

In addition, the negative electrode can also be prepared by adding a binder or conductive material to a negative-electrode active material and by roll-forming the mixture directly into a sheet electrode or by compression molding the mixture into a pellet electrode, or by forming a thin film from the electrode material on a current collector by such techniques as vapor deposition, sputtering, and plating.

[IV-3. Positive Electrode]

Unless impairing the advantages of the present invention, any positive electrode capable of occluding and discharging lithium ions may be used for the nonaqueous electrolyte secondary cell of the present invention. Typically, the positive electrodes have positive-electrode active materials supported on a current collector.

Any positive-electrode active material can be used, for example inorganic compounds such as transition metal oxides, composite oxides of transition metals and lithium (lithium-transition metal composite oxides), transition metal sulfides, and metal oxides; and lithium metal, lithium alloy, or composites thereof. The positive-electrode active materials may be used either alone or in any combination thereof at any proportion.

Specific examples of the positive-electrode active materials include transition metal oxides such as MnO, $V_2O_5$, $V_6O_{13}$, and $TiO_2$; lithium-transition metal composite oxides such as lithium-cobalt composite oxide having a basic composition of $LiCoO_2$, lithium-nickel composite oxide having a basic composition of $LiNiO_2$, lithium-manganese composite oxide having a basic composition of $LiMn_2O_4$ or $LiMnO_2$; lithium-nickel-manganese-cobalt composite oxide, and lithium-nickel-cobalt-aluminium composite oxide; transition metal sulfides such as TiS and FeS; and metal oxides such as $SnO_2$ or $SiO_2$.

Among these preferred are lithium-transition metal composite oxides, and particularly lithium-cobalt composite oxide, lithium-nickel composite oxide, lithium-cobalt-nickel composite oxide, lithium-nickel-manganese-cobalt composite oxide, and lithium-nickel-cobalt-aluminium composite oxide because these can exhibit both high capacity and high cycle characteristics.

Lithium-transition metal composite oxides are also preferred because the oxides can be structurally stabilized by substituting some of cobalt, nickel or manganese in the oxides with other metals such as Al, Ti, V, Cr, Mn, Fe, Co, Li, Ni, Cu, Zn, Mg, Ga, and Zr.

Unless significantly impairing the advantages of the present invention, any known current collector can be used for a positive electrode.

Nonlimiting examples of the current collector materials for a positive electrode that are commonly used include aluminium, titanium, and tantalum, and alloys thereof. Among these preferred are aluminium and alloys thereof.

The current collectors for a positive electrode are the same as those for a negative-electrode with respect to the other points including the facts that it is preferred to roughen the surface in advance and that perforated collectors may be used, and the thickness of the collectors.

Any conventional method can be used without limitation for producing the positive electrode.

As in the negative electrode, an example of such methods for producing the positive electrode involves adding additives such as a binder, thickener, conductive material, filler, and solvent to the positive-electrode active material to make slurry, applying this slurry on the current collector, pressing it to densify after drying, and forming a negative-electrode active material layer on the current collection. Like the negative electrode, the positive electrode may also contain a thickener, conductive material, or filler in order to increase its mechanical strength and conductivity.

After drying and pressing, the positive-electrode active material layer may any density, but the density is typically 3.0 g/cm³ or more.

Like the negative electrode, the positive electrode can also be prepared by adding a binder or conductive material to a positive-electrode active material and by roll-forming the mixture directly into a sheet electrode or by compression molding the mixture into a pellet electrode, or by forming a thin film from the electrode material on a current collector by such techniques as vapor deposition, sputtering, and plating.

[IV-4. Separator]

A separator is typically interposed between the positive and negative electrodes in order to prevent short circuiting therebetween. In this case, the separator is typically impregnated with a nonaqueous electrolytic solution of the present invention.

Unless significantly impairing the advantages of the present invention, any known separator can be used. The separator may be of any material and shape. Preferred examples are separators in the form of porous sheet or nonwoven fabric that is made from a material stable against the nonaqueous electrolytic solution of the present invention and that has excellent liquid retention properties.

Examples of the separator materials can include polyolefins such as polyethylene and polypropylene, polytetrafluoroethylene, polyethersulfone, and glass filter. Among these preferred are glass filter andpolyolefins, and more preferred are polyolefins. These materials may be used either alone or in any combination thereof at any proportion.

The separator has any thickness, but the thickness is usually 1 μm or more, preferably 5 μm or more, and more preferably 10 μm or more, and usually 50 μm or less, preferably 40 μm or less, and more preferably 30 μm or less. A significantly thin separator may have reduced insulating properties and reduced mechanical strength. A nonaqueous electrolyte secondary cell containing a significantly thick separator may have not only impaired cell characteristics such as discharge rate characteristics, but also decreased energy density as a whole.

The separators in the form of porous film such as porous sheet or nonwoven fabric have any porosity, but the porosity is usually 20% or more, preferably 35% or more, and more preferably 45% or more, and usually 90% or less, preferably 85% or less, and more preferably 75% or less. A separator having a significantly low porosity tends to have such an increased film resistance that the cell containing the separator will have impaired rate characteristics. A separator having a significantly high porosity tends to have reduced mechanical strength and reduced insulating properties.

The separator have any average pore size, but the size is usually 0.5 μm or less and preferably 0.2 μm or less, and usually 0.05 μm or more. A separator with a significantly large average pore size may tend to cause short circuiting. A separator with a significantly small average pore size may to have such an increased film resistance that the cell containing the separator will have impaired rate characteristics.

[5. External Case]

The nonaqueous electrolyte secondary cell of the present invention is composed of the above nonaqueous electrolytic solution, negative electrode, positive electrode, and separator accommodated in an external case. Unless significantly impairing the advantages of the present invention, any known external case can be used.

Any material can be used for the external case, for example nickel-plated iron, stainless steel, aluminium or alloys thereof, nickel, and titanium.

The case can be of any shape, for example cylindrical, rectangular, laminated, coin-shaped, and large-scaled.

[V. Carbonate Compound]

The novel carbonate compounds of the present invention will now be described.

[V-1. Chemical Structure]

The carbonate compounds of the present invention are linear carbonate compounds represented by the following formula (4) (hereinafter referred to as "novel carbonate compound").

[Chemical Formula 10]

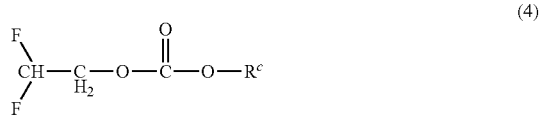

(4)

wherein $R^c$ represents linear unsubstituted alkyl having one to four carbon atoms. That is, $R^c$ is selected from methyl, ethyl, n-propyl, and n-butyl.

Examples of novel carbonate compounds of the present invention include 2,2-difluoroethyl methyl carbonate, 2,2-difluoroethyl ethyl carbonate, 2,2-difluoroethyl n-propyl carbonate, and n-butyl 2,2-difluoroethyl carbonate.

These novel carbonate compounds have a structure having the ethyl group at one end of the linear carbonate compound substituted with two fluorine atoms.

[V-2. Properties]

The novel carbonate compounds of the present invention have higher boiling points compared to conventional carbonate compounds.

The novel carbonate compounds of the present invention also have higher oxidation resistance compared to conventional carbonate compounds. Thus, the novel carbonate compounds of the present invention exhibits higher electrochemical stability compared to conventional carbonate compounds.

[V-3. Production Method]

The novel carbonate compounds of the present invention can be produced by any method, for example synthesis by reaction of 2,2-difluoroethanol with at least one of alkyl chlorocarbonates, i.e., methyl chlorocarbonate, ethyl chlorocarbonate, propyl chlorocarbonate, and butyl chlorocarbonate.

It is desired to ensure that the above synthesis is conducted in any reaction medium that can provide the novel carbonate compounds of the present invention, for example dichloromethane and diethyl ether. The reaction media may be used either alone or in any combination thereof at any proportion.

The above synthesis can be conducted at any reaction temperature that can provide the novel carbonate compounds of the present invention, but the reaction temperature is usually −30° C. or more, preferably −10° C. or more, and more preferably 0° C. or more, and usually 100° C. or less, preferably 80° C. or less, and more preferably 50° C. or less. Below the lower limit, the reaction rate may decrease, resulting in the extended reaction time. Above the upper limit, the alkyl chlorocarbonate may exit from the reaction system. It is especially desired to keep the reaction temperature at 30° C. or less during adding dropwise the alkyl chlorocarbonate.

The reaction time of the above synthesis can be conducted at any reaction time that can provide the novel carbonate compounds of the present invention, but the reaction time is usually 30 minutes or more and preferably one hour or more, and usually 48 hours or less, preferably 24 hours or less, and more preferably 12 hours or less. Below the lower limit, the reaction may be incomplete, resulting in the decreased reaction yield. Above the upper limit, undesired reactions such as transesterification may occur within the system, resulting in the decreased yield of the target product.

In the above synthesis, 2,2-difluoroethanol and the alkyl chlorocarbonate can be used as the materials in any ratio that can provide the novel carbonate compounds of the present invention, but the ratio expressed by "the molar quantity of 2,2-difluoroethanol/the molar quantity of the alkyl chlorocarbonate" is usually 1.2 or more, preferably 1.3 or more, and more preferably 1.5 or more, and usually 2.0 or less, preferably 1.8 or less, and more preferably 1.7 or less. Below the lower limit, the material alcohol may remain unreacted, leading to the decreased reaction yield. Above the upper limit, it may take long time to add dropwise the alcohol.

Typically, products obtained by the above synthesis are purified to provide the novel carbonate compounds of the present invention. In this case, any purification can be used, for example purification by distillation.

[V-4. Application]

The novel carbonate compounds of the present invention can be used in any industrial field. Preferably, these compounds, which have a high boiling point, dielectric constant, oxidation resistance, and electrochemical stability as described above, are used in industrial fields where such properties can be efficiently utilized. For example, these compounds are useful as reaction solvents for organic synthesis, materials for polymer compounds, extraction solvents for various inorganic and organic substances, dilution solvents for paint and ink, materials and dilution solvents for pharmaceuticals and agricultural chemicals, and solvents and additives for electrolytic solutions for energy storage devices.

In particular, when an electrolytic solution for a secondary cell contains the novel carbonate compounds of the present invention as additives, the cycle characteristics of the secondary cell can be enhanced. Therefore, it is especially preferred to contain the novel carbonate compounds of the present invention in an electrolytic solution for a secondary cell.

EXAMPLES

The present invention will now be described in detail by reference to, but not limited to, the following examples. Any modification that does not depart from the sprit of the present invention can be made.

I. Examples on Nonaqueous Electrolytic Solution and Nonaqueous Electrolyte Secondary Cell in Accordance with First Embodiment of Present Invention Examples I-1 to I-24 and Comparative Examples I-1 to I-4

In Examples I-1 to I-24 and Comparative Examples I-1 to I-4, nonaqueous electrolyte secondary cells were assembled and evaluated according to the following procedure. Tables I-1 and I-2 show the results.

[Production of Positive Electrode]

To 85% by weight of $LiCoO_2$ ("C5" available from NIPPON CHEMICAL INDUSTRIAL CO., LTD.) as a positive-electrode active material, 6% by weight of carbon black ("DENKA BLACK" (trademark) available from DENKI KAGAKU KOGYO KABUSHIKI KAISHA) and 9% by weight of polyvinylidene fluoride ("KF-1000" (trade mark) available from Kureha Corporation) were added and mixed. The mixture was then dispersed in N-methyl-2-pyrrolidone to make slurry. The resultant slurry was evenly coated on a 20-μm thick aluminium foil as a positive-electrode current collector so that the capacity of the positive electrode corresponded to 90% of the theoretical capacity of the negative electrode used. After drying for 12 hours at 100° C., the coated aluminium foil was punched into a disk of 12.5 mm in diameter, as a positive electrode.

[Production of Negative Electrode]
[Production of Graphite Negative Electrode]

Slurry was prepared by mixing 83.5 parts by weight of a solution containing 12% by weight of PVDF (polyvinylidene fluoride) in N-methylpyrrolidone, 50 parts by weight of N-methylpyrrolidone, and 100 parts by weight of artificial graphite powder ("KS-6" (trade mark) available from Timcal Corporation) in a disperser. The resultant slurry was evenly coated on an 18-μm thick copper foil as a negative-electrode current collector. After drying, the coated copper foil was pressed into an electrode density of about 1.5 g/cm$^3$. The pressed copper foil was then punched into a disk of 12.5 mm in diameter, as a negative electrode made of graphite (a graphite negative electrode).

[Production of Silicon Alloy Negative Electrode]

Slurry was prepared by mixing 13.3% by weight of artificial graphite powder ("KS-6" (trade mark) available from Timcal Corporation), 54.2 parts by weight of a solution containing 12% by weight of PVDF in N-methylpyrrolidone, 50 parts by weight of N-methylpyrrolidone, and a noncarbonous material for the negative-electrode active material containing 73.2 parts by weight of Silicon and 8.1 parts by weight of copper in a disperser. The resultant slurry was evenly coated on an 18-μm thick copper foil as a negative-electrode current collector. After drying, the coated copper foil was pressed into an electrode density of about 1.5 g/cm$^3$. The pressed copper foil was then punched into a disk of 12.5 mm in diameter, as a negative electrode made of silicon alloy (a silicon alloy negative electrode).

[Preparation of Nonaqueous Electrolytic Solution]

In Examples I-1 to I-24 and Comparative Examples I-1 to I-4, each of the nonaqueous electrolytic solutions, the composition of which was as shown in Tables I-1 and I-2, was prepared by mixing ethylene carbonate (EC) and the respective carbonate compound (the particular linear carbonates for Examples I-1 to I-5, and Examples I-13 to I-17) in the respective volume ratio to make a solution (a nonaqueous solvent), and dissolving $LiPF_6$ as the electrolyte in a concentration of one mole/liter in the solvent. In Examples I-6 to I-10 and Examples I-18 to I-22, each of the nonaqueous electrolytic solutions was prepared by adding the respective predetermined carbonate as the additive in the ratio shown in Tables I-1 and I-2 to the electrolytic solution as used in Example I-2 and Example I-14. In Examples I-11 and I-12 and Examples I-23 and I-24, each of the nonaqueous electrolytic solutions was prepared by adding the respective particular linear carbonate as the additive in the ratio shown in Tables I-1 and I-2 to the electrolytic solution as used in Comparative Example I-2 and Comparative Example I-4.

In Tables I-1 and I-2, the denotation in parentheses in the column of the electrolyte indicates the concentration of the electrolyte in the nonaqueous electrolytic solution; the denotation in parentheses in the column of the nonaqueous solvent indicates the volume ratio of ethylene carbonate to the respective carbonate compound in the nonaqueous solvent used for the nonaqueous electrolytic solution; and the denotation in parentheses in the column of the additive indicates the concentration of the additive (the particular linear carbonates) in the nonaqueous solvent. In Tables I-1 and I-2, DFEMC represents 2,2-difluoroethyl methyl carbonate; DFEEC represents 2,2-difluoroethyl ethyl carbonate; DFEPC represents 2,2-difluoroethyl n-propyl carbonate; BDFEC represents bis(2,2-difluoroethyl)carbonate; FEC represents fluoroethylene carbonate; VC represents vinylene carbonate; DFEC represents 4,5-difluoroethylene carbonate; EMC represents ethyl methyl carbonate; and DEC represents diethyl carbonate.

[Production of Coin Cell]

The above positive electrode was housed in a stainless steel can serving also as a positive-electrode conductor, and then the above negative electrode was placed on the positive electrode via a polyethylene separator impregnated with the nonaqueous electrolytic solution prepared in each Example and Comparative Example. This can and a sealing plate serving also as a negative-electrode conductor were caulked and hermetically sealed with an insulating gasket to produce a coin cell.

A silicon alloy negative electrode was used in Examples I-1 to I-12 and Comparative Examples I-1 and I-2, and a graphite negative electrode in Examples I-13 to I-24 and Comparative Examples I-3 and I-4.

[Evaluation of Coin Cell]

These coin cells were subjected to 100 cycles of charging and discharging at 25° C., the one cycle consisting of constant-current and constant-voltage charging at a charging termination voltage of 4.2 V, a constant current of 3 mA, and a charging termination current of 0.15 µA and constant-current discharging at a discharging termination voltage of 3.0 V and a constant current of 3 mA. During the charge and discharge cycles, the discharge capacities were determined at the first cycle, and at the tenth cycle for Examples and Comparative Examples employing the silicon alloy negative electrode, or at the 100th cycle for Examples and Comparative Examples employing the graphite negative electrode. The capacity retentions at the respective cycles were calculated according to the following equations. The capacity was represented by per unit weight of the negative-electrode active material.

Capacity retention at 10th cycle (%)={Discharge capacity at 10th cycle)/(Discharge capacity at 1st cycle)}×100   [Equation 1]

Capacity retention at 100th cycle (%)={(Discharge capacity at 100th cycle)/(Discharge capacity at 1st cycle)}×100   [Equation 2]

TABLE I-1

Use of silicon alloy negative electrode

| | Composition of nonaqueous electrolytic solution | | | Capacity at first cycle (mAh/g) | After tenth cycle | |
|---|---|---|---|---|---|---|
| | Electrolyte | Nonaqueous solvent | Additive | | Capacity (mAh/g) | Capacity retention (%) |
| Example I-1 | LiPF$_6$ (1M) | EC + DFEMC (30:70) | None | 597 | 489 | 81.9 |
| Example I-2 | LiPF$_6$ (1M) | EC + DFEEC (30:70) | None | 600 | 494 | 82.4 |
| Example I-3 | LiPF$_6$ (1M) | EC + DFEPC (30:70) | None | 602 | 486 | 80.8 |
| Example I-4 | LiPF$_6$ (1M) | EC + BDFEC (30:70) | None | 601 | 508 | 84.5 |
| Example I-5 | LiPF$_6$ (1M) | EC + DEC + DFEMC (30:40:30) | None | 598 | 477 | 79.8 |
| Comparative Example I-1 | LiPF$_6$ (1M) | EC + EMC (30:70) | None | 603 | 321 | 53.2 |
| Comparative Example I-2 | LiPF$_6$ (1M) | EC + DEC (30:70) | None | 601 | 341 | 56.7 |
| Example I-6 | LiPF$_6$ (1M) | EC + DFEEC (30:70) | FEC (2 wt. %) | 604 | 513 | 85.0 |
| Example I-7 | LiPF$_6$ (1M) | EC + DFEEC (30:70) | FEC (30 wt. %) | 599 | 513 | 85.7 |
| Example I-8 | LiPF$_6$ (1M) | EC + DFEEC (30:70) | VC (2 wt. %) | 597 | 507 | 84.9 |
| Example I-9 | LiPF$_6$ (1M) | EC + DFEEC (30:70) | DFEC (2 wt. %) | 602 | 512 | 85.1 |
| Example I-10 | LiPF$_6$ (1M) | EC + DFEEC (30:70) | DFEC (30 wt. %) | 603 | 514 | 85.3 |
| Example I-11 | LiPF$_6$ (1M) | EC + DEC (30:70) | DFEMC (0.5 wt. %) | 598 | 422 | 70.5 |
| Example I-12 | LiPF$_6$ (1M) | EC + DEC (30:70) | DFEMC (2 wt. %) | 602 | 438 | 72.8 |

DFEMC: 2,2-Difluoroethyl methyl carbonate
DFEEC: 2,2-Difluoroethyl ethyl carbonate
DFEPC: 2,2-Difluoroethyl n-propyl carbonate
BDFEC: Bis(2,2-difluoroethyl) carbonate
FEC: Fluoroethylene carbonate: predetermined carbonate
VC: Vinylene carbonate: predetermined carbonate
DFEC: 4,5-Difluoroethylene carbonate: predetermined carbonate
EMC: Ethyl methyl carbonate
DEC: Diethyl carbonate

TABLE I-2

Use of graphite negative electrode

| | Nonaqueous electrolytic solution | | | Capacity at first cycle (mAh/g) | After tenth cycle | |
|---|---|---|---|---|---|---|
| | Electrolyte | Nonaqueous solvent | Additive | | Capacity (mAh/g) | Capacity retention (%) |
| Example I-13 | $LiPF_6$ (1M) | EC + DFEMC (30:70) | None | 350 | 343 | 98.1 |
| Example I-14 | $LiPF_6$ (1M) | EC + DFEEC (30:70) | None | 349 | 342 | 98.0 |
| Example I-15 | $LiPF_6$ (1M) | EC + DFEPC (30:70) | None | 353 | 347 | 98.3 |
| Example I-16 | $LiPF_6$ (1M) | EC + BDFEC (30:70) | None | 351 | 343 | 97.8 |
| Example I-17 | $LiPF_6$ (1M) | EC + DEC + DFEMC (30:40:30) | None | 348 | 341 | 97.9 |
| Example I-18 | $LiPF_6$ (1M) | EC + DFEEC (30:70) | FEC (2 wt. %) | 350 | 344 | 98.2 |
| Example I-19 | $LiPF_6$ (1M) | EC + DFEEC (30:70) | FEC (30 wt. %) | 352 | 347 | 98.6 |
| Example I-20 | $LiPF_6$ (1M) | EC + DFEEC (30:70) | VC (2 wt. %) | 354 | 348 | 98.4 |
| Example I-21 | $LiPF_6$ (1M) | EC + DFEEC (30:70) | DFEC (2 wt. %) | 356 | 350 | 98.4 |
| Example I-22 | $LiPF_6$ (1M) | EC + DFEEC (30:70) | DFEC (30 wt. %) | 357 | 352 | 98.7 |
| Comparative Example I-3 | $LiPF_6$ (1M) | EC + EMC (30:70) | None | 345 | 328 | 95.0 |
| Comparative Example I-4 | $LiPF_6$ (1M) | EC + DEC (30:70) | None | 343 | 322 | 93.8 |
| Example I-23 | $LiPF_6$ (1M) | EC + DEC (30:70) | DFEMC (0.5 wt. %) | 347 | 337 | 97.2 |
| Example I-24 | $LiPF_6$ (1M) | EC + DEC (30:70) | DFEMC (2 wt. %) | 349 | 340 | 97.5 |

DFEMC: 2,2-Difluoroethyl methyl carbonate
DFEEC: 2,2-Difluoroethyl ethyl carbonate
DFEPC: 2,2-Difluoroethyl n-propyl carbonate
BDFEC: Bis(2,2-difluoroethyl) carbonate
FEC: Fluoroethylene carbonate: predetermined carbonate
VC: Vinylene carbonate: predetermined carbonate
DFEC: 4,5-Difluoroethylene carbonate: predetermined carbonate
EMC: Ethyl methyl carbonate
DEC: Diethyl carbonate Tables I-1 and I-2 show that the cells of Examples I-1 to I-12 and Examples I-13 to I-24 containing the particular linear carbonate had a higher capacity retention after cycles and had superior cycle characteristics to those of Comparative Examples I-1 and I-2 and Comparative Examples I-3 and I-4 containing no particular linear carbonate.

II. Examples on Nonaqueous Electrolytic Solution and Nonaqueous Electrolyte Secondary Cell in Accordance with Second Embodiment of Present Invention Examples II-1 to II-11 and Comparative Examples II-1 to II-3

In Examples II-1 to II-11 and Comparative Examples II-1 to II-3, nonaqueous electrolyte secondary cells were fabricated and evaluated according to the following procedure. Tables II-1 and II-2 show the results.

[Production of Positive Electrode]

To 85% by weight of $LiCoO_2$ ("C5" available from NIPPON CHEMICAL INDUSTRIAL CO., LTD.) as a positive-electrode active material, 6% by weight of carbon black ("DENKA BLACK" (trademark) available from DENKI KAGAKU KOGYO KABUSHIKI KAISHA) and 9% by weight of polyvinylidene fluoride ("KF-1000" (trade mark) available from Kureha Corporation) were added and mixed. The mixture was then dispersed in N-methyl-2-pyrrolidone to make slurry. The resultant slurry was evenly coated on a 20-μm thick aluminium foil as a positive-electrode current collector so that the capacity of the positive electrode corresponded to 90% of the theoretical capacity of the negative electrode used. After drying at 100° C. for 12 hours, the coated aluminium foil was punched into a disk of 12.5 mm in diameter, as a positive electrode.

[Production of Graphite Negative Electrode]

Slurry was prepared by mixing 83.5 parts by weight of a solution containing 12% by weight of PVDF (polyvinylidene fluoride) in N-methylpyrrolidone, 50 parts by weight of N-methylpyrrolidone, and 100 parts by weight of artificial graphite powder ("KS-6" (trade mark) available from Timcal Corporation) in a disperser. The resultant slurry was evenly coated on an 18-μm thick copper foil as a negative-electrode current collector. After drying, the coated copper foil was pressed into an electrode density of about 1.5 g/cm³. The pressed copper foil was then punched into a disk of 12.5 μm in diameter, as a negative electrode.

[Preparation of Nonaqueous Electrolytic Solution]

Nonaqueous electrolytic solution were prepared by mixing ethylene carbonate and ethyl methyl carbonate in a volume ratio of 3:7 to prepare a solvent, adding to the solvent a particular compound (2) and/or a respective predetermined carbonate in a ratio shown in Tables II-1 and II-2 appropriately, and dissolving $LiPF_6$ as the electrolyte in a concentration of one mole/liter in the solvent. The mark "-" used in Tables II-1 and II-2 means that no particular compound (2) or predetermined carbonate was used in the sample.

[Production of Coin Cell]

The above positive electrode was housed in a stainless steel can, which also serves as a positive-electrode conductor, and then the above negative electrode was placed on the positive electrode via a polyethylene separator impregnated with the electrolytic solution prepared in each Example and Comparative Example. This can and a sealing plate also serving as a negative-electrode conductor were caulked and hermetically sealed with an insulating gasket to produce a coin cell.

[Evaluation of Coin Cell]

These coin cells were subjected to 100 cycles of charging and discharging at 25° C., the one cycle consisting of constant-current and constant-voltage charging at a charging termination voltage of 4.2 V, a constant current of 3 mA, and a charging termination current of 0.15 µA and constant-current discharging at a discharging termination voltage of 3.0 V and a constant current of 3 mA. During the charge and discharge cycles, the discharge capacities were determined at the first cycle and at the 100th cycle. The capacity retentions at the 100th cycle were calculated according to the following equation. The capacity was represented by per unit weight of the negative-electrode active material.

Capacity retention at 100th cycle (%)={(Discharge capacity at 100th cycle)/(Discharge capacity at 1st cycle)}×100      [Equation 3]

TABLE 3

[Table II-1]

| | Particular compound (2) | | Predetermined carbonate | | Negative electrode material | Capacity retention at the 100$^{th}$ cycle |
|---|---|---|---|---|---|---|
| | Structure | Amount | Structure | Amount | | |
| Example II-1 | F—CH$_2$—CH(—CH$_2$—O—)O—C(=O)— (fluoroethylene carbonate) | 2 wt. % | — | — | Graphite | 89% |
| Example II-2 | F—CH$_2$—CH(—CH$_2$—O—)O—C(=O)— | 2 wt. % | HC=CH—O—C(=O)—O— (vinylene carbonate) | 2 wt. % | Graphite | 94% |
| Example II-3 | F—CH$_2$—CH(—CH$_2$—O—)O—C(=O)— | 2 wt. % | HC=CH—O—C(=O)—O— + H$_2$C=CH—CH(—CH$_2$—O—)O—C(=O)— | 2 wt. % + 2 wt. % | Graphite | 96% |
| Example II-4 | F—CH$_2$—CH(—CH$_2$—O—)O—C(=O)— | 2 wt. % | F—CH(—CH$_2$—O—)O—C(=O)— | 2 wt. % | Graphite | 95% |

TABLE 3-continued

[Table II-1]

| | Particular compound (2) | | Predetermined carbonate | | Negative electrode material | Capacity retention at the 100$^{th}$ cycle |
|---|---|---|---|---|---|---|
| | Structure | Amount | Structure | Amount | | |
| Example II-5 | F—CH$_2$—CH(—O—)CH$_2$(—O—)C=O (fluoromethyl ethylene carbonate) | 2 wt. % | F—CH(—O—)CH$_2$(—O—)C=O (fluoroethylene carbonate) | 30 wt. % | Graphite | 97% |
| Example II-6 | F—CH$_2$—CH(—O—)CH$_2$(—O—)C=O | 2 wt. % | F—CH(—O—)CH—F(—O—)C=O (difluoroethylene carbonate) | 2 wt. % | Graphite | 95% |
| Example II-7 | F—CH$_2$—CH(—O—)CH$_2$(—O—)C=O | 2 wt. % | F—CH(—O—)CH—F(—O—)C=O | 30 wt. % | Graphite | 98% |
| Example II-8 | F$_2$CH—CH(—O—)CH$_2$(—O—)C=O (difluoromethyl ethylene carbonate) | 2 wt. % | — | — | Graphite | 91% |
| Example II-9 | FCH$_2$—CH$_2$—CH(—CH$_2$—O—)C=O (γ-butyrolactone derivative) | 2 wt. % | — | — | Graphite | 89% |
| Example II-10 | F—CH$_2$—CH(—CH$_2$—O—)CH$_2$(—O—)C=O | 2 wt. % | — | — | Graphite | 89% |
| Example II-11 | H$_2$C—F, H$_2$C—CH, H$_2$C(—O—)C=O | 2 wt. % | — | — | Graphite | 89% |

TABLE 4

[Table II-2]

| | Particular compound (2) | | Predetermined carbonate | | Negative electrode material | Capacity retention at the 100$^{th}$ cycle |
|---|---|---|---|---|---|---|
| | Structure | Amount | Structure | Amount | | |
| Comparative Example II-1 | — | — | — | — | Graphite | 79% |
| Comparative Example II-2 | — | — | HC=CH, O, O, C=O (vinylene carbonate) | 2 wt. % | Graphite | 88% |
| Comparative Example II-3 | — | — | F,F,F—C—CH—CH$_2$, O, O, C=O | 2 wt. % | Graphite | 81% |

Examples II-12 to II-18 and Comparative Examples II-4 and II-5

In Examples II-12 to II-18 and Comparative Examples II-4 and II-5, nonaqueous electrolyte secondary cells were fabricated and evaluated as in Examples II-1 to II-11 and Comparative Examples II-1 to II-3, except that a silicon alloy negative electrode was used, a particular compound (2) and/or a predetermined carbonate shown in Table II-3 was used to be dissolved in a nonaqueous electrolytic solution, and the discharge capacities at the tenth cycle were determined to calculate the capacity retentions at the tenth cycle instead of those at the 100th cycle. Table II-3 shows the results. The mark "-" used in Table II-3 means that no particular compound (2) or predetermined carbonate was used in the sample. The capacity retentions at the tenth cycle were calculated according to the following equation. The capacity was represented by per unit weight of the negative-electrode active material.

Capacity retention at 10th cycle (%)={(Discharge capacity at 10th cycle)/(Discharge capacity at 1st cycle)}×100    [Equation 4]

The silicon alloy negative electrode was produced as follows.

[Production of Silicon Alloy Negative Electrode]

Slurry was prepared by mixing 12.2% by weight of artificial graphite powder ("KS-6" (trade mark) available from Timcal Corporation), 54.2 parts by weight of a solution containing 12% by weight of PVDF in N-methylpyrrolidone, 50 parts by weight of N-methylpyrrolidone, and a noncarbonous material for the negative-electrode active material containing 73.2 parts by weight of silicon and 8.1 parts by weight of copper in a disperser. The resultant slurry was evenly coated on an 18-μm thick copper foil as a negative-electrode current collector. After drying, the coated copper foil was pressed into an electrode density of about 1.5 g/cm$^3$. The pressed copper foil was then punched into a disk of 12.5 mm in diameter, as a negative electrode made of silicon alloy (a silicon alloy negative electrode).

TABLE 5

[Table II-3]

| | Particular compound (2) | | Predetermined carbonate | | Negative electrode material | Capacity retention at the 100$^{th}$ cycle |
|---|---|---|---|---|---|---|
| | Structure | Amount | Structure | Amount | | |
| Example II-12 | F—CH$_2$, CH—CH$_2$, O, O, C=O | 2 wt. % | — | — | Silicon alloy | 91% |

TABLE 5-continued

[Table II-3]

| | Particular compound (2) | | Predetermined carbonate | | Negative electrode material | Capacity retention at the 100th cycle |
|---|---|---|---|---|---|---|
| | Structure | Amount | Structure | Amount | | |
| Example II-13 | F—CH₂–CH–CH₂ (fluorinated cyclic carbonate) | 2 wt. % | HC=CH (vinylene carbonate) | 2 wt. % | Silicon alloy | 93% |
| Example II-14 | F—CH₂–CH–CH₂ | 2 wt. % | F–CH–CH₂ (fluorinated cyclic carbonate) + HC=CH | 2 wt. % + 2 wt. % | Silicon alloy | 94% |
| Example II-15 | F—CH₂–CH–CH₂ | 2 wt. % | F–CH–CH₂ | 2 wt. % | Silicon alloy | 95% |
| Example II-16 | F—CH₂–CH–CH₂ | 2 wt. % | F–CH–CH₂ | 30 wt. % | Silicon alloy | 97% |
| Example II-17 | F—CH₂–CH–CH₂ | 2 wt. % | F–CH–CH–F | 2 wt. % | Silicon alloy | 94% |
| Example 18 | F—CH₂–CH–CH₂ | 2 wt. % | F–CH–CH–F | 30 wt. % | Silicon alloy | 97% |
| Comparative Example II-4 | — | — | — | — | Silicon alloy | 89% |
| Comparative Example II-5 | — | — | HC=CH | 2 wt. % | Silicon alloy | 90% |

[Conclusion]

Tables II-1 to II-3 show that with the graphite negative electrode, the cells of Examples II-1 to II-11 containing the particular compound (2) in a nonaqueous electrolytic solution had excellent cycle characteristics compared to those of Comparative Examples II-1 to II-3.

Comparing Examples II-1 through II-7, these tables also show that the cells of Examples II-2 to II-7 containing a combination of a known compound to improve cycle characteristics (a predetermined carbonate) and a particular compound (2) have further improved cycle characteristics compared to that of Example II-1.

The tables also show that a similar trend is observed by comparison of the cells of Examples II-12 to II-18 containing a silicon alloy negative electrode with those of Comparative Examples II-4 and II-5.

III. Examples on Nonaqueous Electrolytic Solution and Nonaqueous Electrolyte Secondary Cell in Accordance with Second Embodiment of Present Invention

Examples III-1 to III-11 and Comparative Examples III-1 and III-2

In Examples III-1 to III-11 and Comparative Examples III-1 and III-2, nonaqueous electrolyte secondary cells were fabricated and evaluated according to the following procedure. Table III-1 shows the results.

[Production of Positive Electrode]

To 85% by weight of $LiCoO_2$ ("C5" available from NIPPON CHEMICAL INDUSTRIAL CO., LTD.) as a positive-electrode active material, 6% by weight of carbon black ("DENKA BLACK" (trademark) available from DENKI KAGAKU KOGYO KABUSHIKI KAISHA) and 9% by weight of polyvinylidene fluoride ("KF-1000" (trade mark) available from Kureha Corporation) were added and mixed. The mixture was then dispersed in N-methyl-2-pyrrolidone to make slurry. The resultant slurry was evenly coated on a 20-μm thick aluminium foil as a positive-electrode current collector so that the capacity of the positive electrode corresponded to 90% of the theoretical capacity of the negative electrode used. After drying at 100° C. for 12 hours, the coated aluminium foil was punched into a disk of 12.5 mm in diameter, as a positive electrode.

[Production of Graphite Negative Electrode]

Slurry was prepared by mixing 83.5 parts by weight of a solution containing 12% by weight of PVDF (polyvinylidene fluoride) in N-methylpyrrolidone, 50 parts by weight of N-methylpyrrolidone, and 100 parts by weight of artificial graphite powder ("KS-6" (trade mark) available from Timcal Corporation) in a disperser. The resultant slurry was evenly coated on an 18-1 μm thick copper foil as a negative-electrode current collector. After drying, the coated copper foil was pressed into an electrode density of about 1.5 $g/cm^3$. The pressed copper foil was then punched into a disk of 12.5 μm in diameter, as a negative electrode made of graphite (a graphite negative electrode).

[Preparation of Nonaqueous Electrolytic Solution]

Nonaqueous electrolytic solutions were prepared by mixing ethylene carbonate and ethyl methyl carbonate in a volume ratio of 3:7 to prepare a solvent, adding to the solvent a particular compound (3) and/or a respective predetermined carbonate in the respective ratio shown in Table III-1 appropriately, and dissolving $LiPF_6$ as the electrolyte in a concentration of one mole/liter in the solvent. The mark "-" used in Table III-1 means that no particular compound (3) or predetermined carbonate was used in this sample.

[Production of Coin Cell]

The above positive electrode was housed in a stainless steel can, which also serves as a positive-electrode conductor, and then the above negative electrode was placed on the positive electrode via a polyethylene separator impregnated with the nonaqueous electrolytic solution prepared in each Example and Comparative Example.

This can and a sealing plate serving also as a negative-electrode conductor were caulked and hermetically sealed with an insulating gasket to produce a coin cell.

[Evaluation of Coin Cell]

These coin cells were subjected to 100 cycles of charging and discharging at 25° C., the one cycle consisting of constant-current and constant-voltage charging at a charging termination voltage of 4.2 V, a constant current of 3 mA, and a charging termination current of 0.15 μA and constant-current discharging at a discharging termination voltage of 3.0 V and a constant current of 3 mA. During the charge and discharge cycles, the discharge capacities were determined at the first cycle and at the 100th cycle. The capacity retentions at the 100th cycle were calculated according to the following equation. The capacity was represented by per unit weight of the negative-electrode active material.

Capacity retention at 10th or 100th cycle (%)={(Discharge capacity at 10th or 100th cycle)/(Discharge capacity at 1st cycle)}×100    [Equation 5]

TABLE 6

[Table III-1]

| | Particular compound (3) | | Predetermined carbonate | | Negative electrode | Capacity retention at the 100$^{th}$ |
|---|---|---|---|---|---|---|
| | Structure | Amount | Structure | Amount | material | cycle |
| Example III-1 | F–CH$_2$–C(=O)–O–CH$_3$ | 2 wt. % | — | — | Graphite | 90% |

TABLE 6-continued

[Table III-1]

| | Particular compound (3) | | Predetermined carbonate | | Negative electrode material | Capacity retention at the 100$^{th}$ cycle |
|---|---|---|---|---|---|---|
| | Structure | Amount | Structure | Amount | | |
| Example III-2 | F-CH$_2$-CH$_2$-C(O)-O-CH$_3$ | 2 wt. % | Vinylene carbonate (HC=CH, O-C(=O)-O) | 2 wt. % | Graphite | 94% |
| Example III-3 | F-CH$_2$-CH$_2$-C(O)-O-CH$_3$ | 2 wt. % | Vinylene carbonate + vinyl ethylene carbonate | 2 wt. % + 2 wt. % | Graphite | 96% |
| Example III-4 | F-CH$_2$-CH$_2$-C(O)-O-CH$_3$ | 2 wt. % | Fluoroethylene carbonate | 2 wt. % | Graphite | 93% |
| Example III-5 | F-CH$_2$-CH$_2$-C(O)-O-CH$_3$ | 2 wt. % | Fluoroethylene carbonate | 30 wt. % | Graphite | 95% |
| Example III-6 | F-CH$_2$-CH$_2$-C(O)-O-CH$_3$ | 2 wt. % | Difluoroethylene carbonate | 2 wt. % | Graphite | 93% |
| Example III-7 | F-CH$_2$-CH$_2$-C(O)-O-CH$_3$ | 2 wt. % | Difluoroethylene carbonate | 30 wt. % | Graphite | 96% |
| Example III-8 | F-CH$_2$-CH$_2$-C(O)-O-CH$_2$-CH$_3$ | 2 wt. % | — | — | Graphite | 90% |
| Example III-9 | F-CH$_2$-CH$_2$-C(O)-O-CH$_2$-CH$_2$-F | 2 wt. % | — | — | Graphite | 91% |

TABLE 6-continued

[Table III-1]

| | Particular compound (3) | | Predetermined carbonate | | Negative electrode material | Capacity retention at the 100$^{th}$ cycle |
|---|---|---|---|---|---|---|
| | Structure | Amount | Structure | Amount | | |
| Example III-10 | F–CH$_2$–CH$_2$–C(=O)–NH$_2$ | 2 wt. % | — | — | Graphite | 89% |
| Example III-11 | F–CH$_2$–CH$_2$–C(=O)–N(CH$_3$)$_2$ | 2 wt. % | — | — | Graphite | 90% |
| Comparative Example III-1 | — | — | — | — | Graphite | 79% |
| Comparative Example III-2 | — | — | vinylene carbonate (HC=CH with O–C(=O)–O ring) | 2 wt. % | Graphite | 88% |

Examples III-12 to III-18 and Comparative Examples III-3 and III-4

In Examples III-12 to III-18 and Comparative Examples III-3 and III-4, nonaqueous electrolyte secondary cells were fabricated and evaluated as in Examples III-1 to III-11 and Comparative Examples III-1 and III-2, except that a silicon alloy negative electrode was used, a particular compound (3) and/or a predetermined carbonate shown in Table III-2 was used to be dissolved in a nonaqueous electrolytic solution, and the discharge capacities at the tenth cycle were determined to calculate the capacity retentions at the tenth cycle instead of those at the 100th cycle. Table III-2 shows the results. The mark "-" used in Table III-2 means that no particular compound (3) or predetermined carbonate was used in this sample. The capacity retentions at the tenth cycle were calculated according to the following equations. The capacity was represented by per unit weight of the negative-electrode active material.

Capacity retention at 10th or 100th cycle (%)={(Discharge capacity at 10th or 100th cycle)/(Discharge capacity at 1st cycle)}×100  [Equation 6]

The silicon alloy negative electrode was produced as follows.

[Production of Silicon Alloy Negative Electrode]

Slurry was prepared by mixing 12.2% by weight of artificial graphite powder ("KS-6" (trade mark) available from Timcal Corporation), 54.2 parts by weight of a solution containing 12% by weight of PVDF in N-methylpyrrolidone, 50 parts by weight of N-methylpyrrolidone, and a noncarbonous material for the negative-electrode active material containing 73.2 parts by weight of silicon and 8.1 parts by weight of copper in a disperser. The resultant slurry was evenly coated on an 18-μm thick copper foil as a negative-electrode current collector. After drying, the coated copper foil was pressed into an electrode density of about 1.5 g/cm$^3$. The pressed copper foil was then punched into a disk of 12.5 mm in diameter, as a negative electrode made of silicon alloy (a silicon alloy negative electrode).

TABLE 7

[Table III-2]

| | Particular compound (3) | | Predetermined carbonate | | Negative electrode material | Capacity retention at the 100$^{th}$ cycle |
|---|---|---|---|---|---|---|
| | Structure | Amount | Structure | Amount | | |
| Example III-12 | F–CH$_2$–CH$_2$–C(=O)–O–CH$_3$ | 2 wt. % | — | — | Silicon alloy | 92% |

TABLE 7-continued

[Table III-2]

| | Particular compound (3) | | Predetermined carbonate | | Negative electrode material | Capacity retention at the 100$^{th}$ cycle |
|---|---|---|---|---|---|---|
| | Structure | Amount | Structure | Amount | | |
| Example III-13 | F-CH$_2$-CH$_2$-C(=O)-O-CH$_3$ | 2 wt. % | Vinylene carbonate (HC=CH, O-C(=O)-O) | 2 wt. % | Silicon alloy | 94% |
| Example III-14 | F-CH$_2$-CH$_2$-C(=O)-O-CH$_3$ | 2 wt. % | Fluoroethylene carbonate (F-CH-CH$_2$, O-C(=O)-O) + Vinylene carbonate (HC=CH, O-C(=O)-O) | 2 wt. % + 2 wt. % | Silicon alloy | 95% |
| Example III-15 | F-CH$_2$-CH$_2$-C(=O)-O-CH$_3$ | 2 wt. % | Fluoroethylene carbonate (F-CH-CH$_2$, O-C(=O)-O) | 2 wt. % | Silicon alloy | 96% |
| Example III-16 | F-CH$_2$-CH$_2$-C(=O)-O-CH$_3$ | 2 wt. % | Fluoroethylene carbonate (F-CH-CH$_2$, O-C(=O)-O) | 30 wt. % | Silicon alloy | 98% |
| Example III-17 | F-CH$_2$-CH$_2$-C(=O)-O-CH$_3$ | 2 wt. % | Difluoroethylene carbonate (F-CH-CH-F, O-C(=O)-O) | 2 wt. % | Silicon alloy | 95% |
| Example III-18 | F-CH$_2$-CH$_2$-C(=O)-O-CH$_3$ | 2 wt. % | Difluoroethylene carbonate (F-CH-CH-F, O-C(=O)-O) | 30 wt. % | Silicon alloy | 98% |
| Compound Example III-3 | — | — | — | — | Silicon alloy | 89% |
| Compound Example III-4 | — | — | Vinylene carbonate (HC=CH, O-C(=O)-O) | 2 wt. % | Silicon alloy | 90% |

[Conclusion]

Tables III-1 and III-2 show that when containing a graphite negative electrode, the cells of Examples III-1 to III-11 containing a particular compound (3) in a nonaqueous electrolytic solution had excellent cycle characteristics compared to those of Comparative Examples III-1 and III-2.

Comparing Examples III-1 through III-7, these tables also show that the cells of Examples III-2 to III-7 containing a combination of a compound previously known to improve cycle characteristics (a predetermined carbonate) and a particular compound (3) have further improved cycle characteristics compared to that of Example III-1.

The tables also show that a similar trend is observed by comparison of the cells of Examples III-12 to III-18 containing a silicon alloy negative electrode with those of Comparative Examples III-3 and III-4.

IV. Examples on Carbonate Compound of the Invention

Example IV-1

Synthesis of Difluoroacetic Acid

To a 500 ml pressure vessel, ethanol (46 g, 1 mol) and sodium metal (2 g) were added and cooled with dry ice. To the vessel, tetrafluoroethylene (67 g, 0.67 mol) was then added and sealed.

The sealed vessel was shaken for four hours at 55° C. To the resultant difluoroethyl ethyl ether (42 g, 0.3 mol), fuming nitric acid (42 ml) was added dropwise, and heated at 55° C. for eight hours with stirring. The resultant mixture was poured into water, and then extracted with diethyl ether. The diethyl ether extract was dried over diphosphorus pentoxide and was subjected to distillation to give ethyl difluoroacetate.

The resultant ethyl difluoroacetate was hydrolyzed with diluted sulfuric acid to yield difluoroacetic acid.

Synthesis of 2,2-Difluoroethanol

Difluoroacetic acid (85.5 g, 0.89 mol) was slowly added dropwise to benzyl chloride (140 ml, 1.2 mol), followed by heating at 170° C. The mixture was then cooled, and was added dropwise to a solution of lithium aluminium hydroxide (15 g, 0.4 mol) in diethyl ether (700 ml) with vigorous stirring.

After the addition was complete, the reaction mixture was refluxed with heat for one hour. After Water (75 ml) was added, the solution was poured onto a mixture of ice and concentrated sulfuric acid (500 ml) in a vessel. The resultant aqueous phase was extracted with diethyl ether to yield 2,2-difluoroethanol.

Synthesis of 2,2-Difluoroethyl Methyl Carbonate

To a flask charged with difluoroethanol (5 g, 0.06 mol), methylene chloride (20 g), and pyridine (7.9 g, 0.1 mol), methyl chlorocarbonate (6.9 g, 0.073 mol) was added dropwise with ice cooling, followed by stirring at room temperature for one hour. To the resultant mixture, 1 N hydrochloric acid was added, and the mixture was washed and was subjected to extraction with water and saturated saline.

The solvent was distilled off from the extracted organic phase, and the residue was distilled to yield a product (2,2-difluoroethyl methyl carbonate). The product obtained was 4.5 g (yield: 54%). The structure of the resulting compound was determined by analysis of $^1H$, $^{13}C$, and $^{19}F$ NMR spectra, and a mass spectrum (M/e=140).

Peak data in the measured $^1H$, $^{13}C$, and $^{19}F$ NMR spectra is listed with the structure determined from the spectra. In the structural formula and the peak data, each of a, b, c, and d represents the notation for the carbon at the corresponding position in the following structural formula.

[Chemical Formula 11]

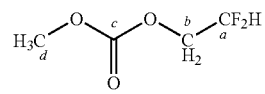

Figure 2:
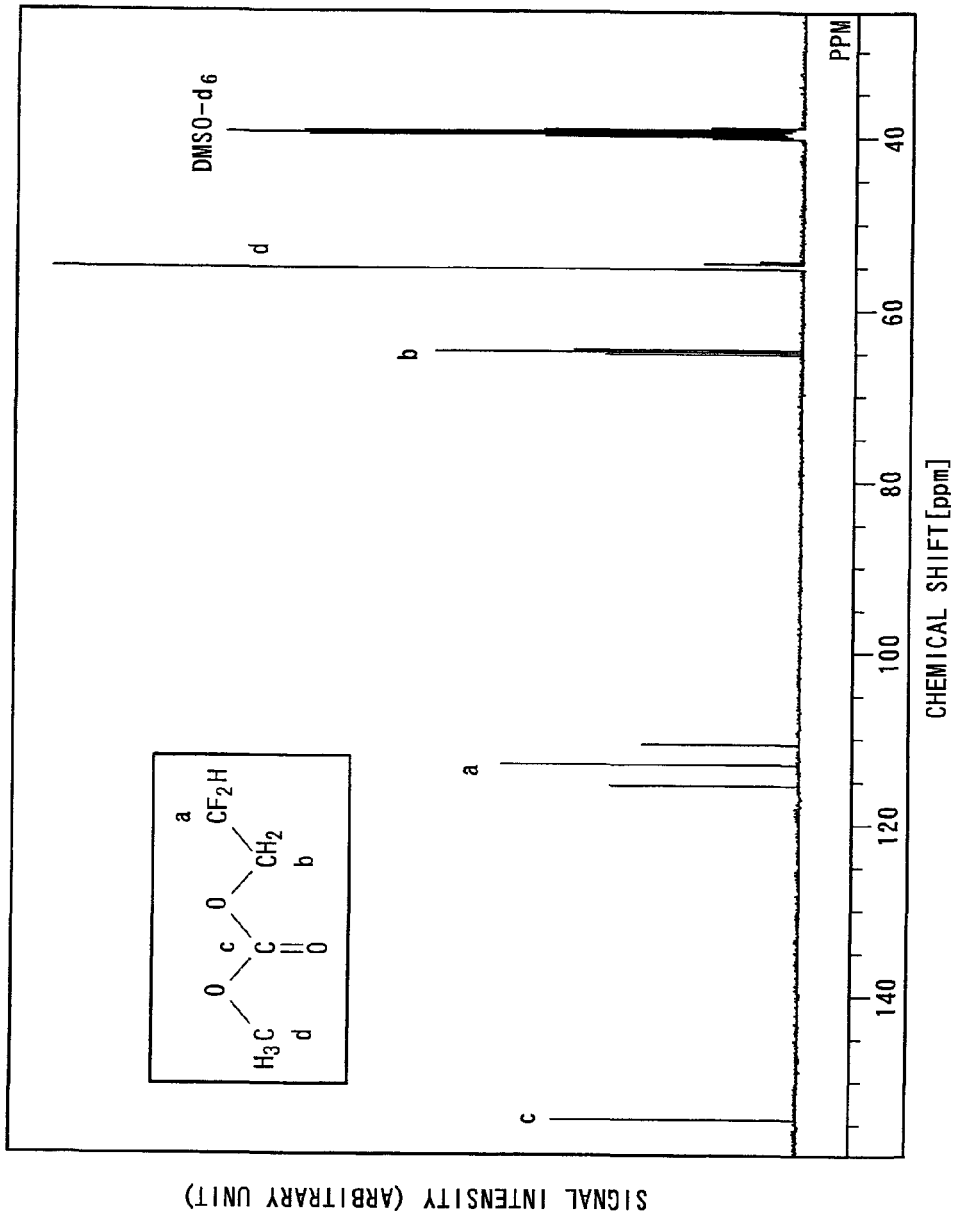
FIG. 2 shows a $^{13}$C NMR spectrum of a product prepared according to Example IV-1 of the present invention.

$^1H$ NMR (DMSO-d6)
δ 3.75 s (d)
δ 4.38 td $J_{H-F}$=15 Hz, $J_{H-H}$=3 Hz (b)
δ 6.26 tt $J_{H-F}$=54 Hz, $J_{H-H}$=3 Hz (a)
$^{13}C$ NMR (DMSO-d6)
δ 55.20 s (d)
δ 64.89 t $J_{C-F}$=26 Hz (b)
δ 113.07 t $J_{C-F}$=239 Hz (a)
δ 154.42 s (c)
$^{19}F$ NMR (DMSO-d6, Internal Standard: C6F6)
δ −126.7 dt $J_{F-H}$=54 Hz, $J_{F-H}$=15 Hz FIG. 1 shows the $^1H$ NMR spectrum of the product (2,2-difluoroethyl methyl carbonate) obtained in Example IV-1, and FIG. 2 shows the $^{13}C$ NMR spectrum.

Example IV-2

Synthesis of 2,2-Difluoroethyl Ethyl Carbonate 2,2-Difluoroethyl ethyl carbonate was prepared as in [Synthesis of 2,2-Difluoroethyl Methyl Carbonate] of Example IV-1, except that ethyl chlorocarbonate (7.9 g, 0.073 mol) was substituted for methyl chlorocarbonate (6.9 g, 0.073 mol).

The product 2,2-difluoroethyl ethyl carbonate obtained was 5.1 g (yield: 55%). The structure of the compound obtained was determined by analysis of $^1H$, $^{13}C$, and $^{19}F$ NMR spectra, and a mass spectrum (M/e=154).

Peak data in the measured $^1H$, $^{13}C$, and $^{19}F$ NMR spectra is listed with the structure determined from the spectra. In the structural formula and the peak data, each of a, b, c, d, and e represents the notation for the carbon at the corresponding position in the following structural formula.

[Chemical Formula 12]

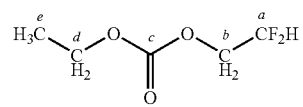

$^1H$ NMR (DMSO-d6)
δ 1.22 t $J_{H-H}$=7 Hz (e)
δ 4.14 q $J_{H-H}$=7 Hz (d)
δ 4.37 t d $J_{H-F}$=15 Hz, $J_{H-H}$=3 Hz (b)
δ 6.26 t t $J_{H-F}$=54 Hz, $J_{H-H}$=3 Hz (a)
$^{13}C$ NMR (DMSO-d6)
δ 13.94 s (e)
δ 64.30 s (d)
δ 64.68 t $J_{C-F}$=26 Hz (b)
δ 113.09 t $J_{C-F}$=238 Hz (a)
δ 153.76 s (c)
$^{19}F$ NMR
δ −126.7 d t $J_{F-H}$=54 Hz, $J_{F-H}$=15 Hz

Figure 3:
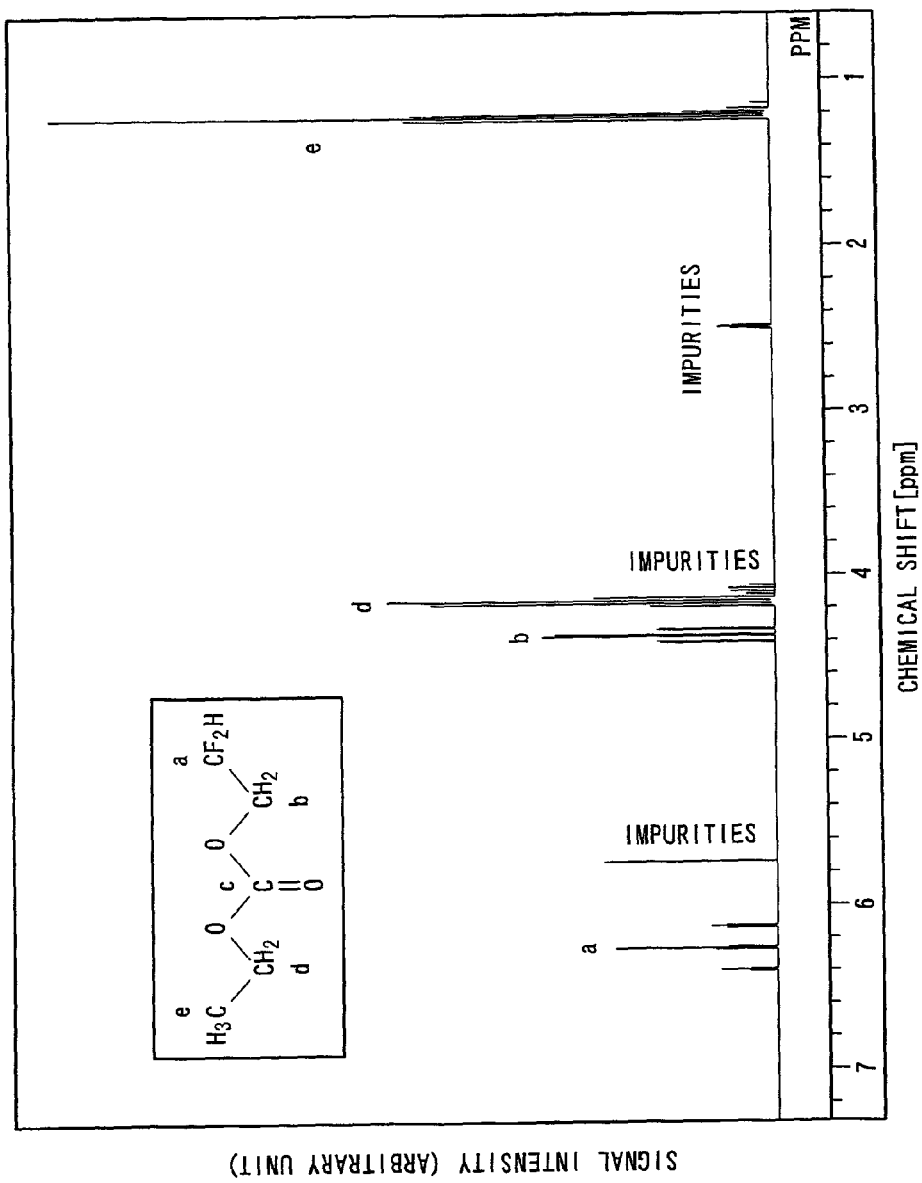
FIG. 3 shows a $^1$H NMR spectrum of a product prepared according to Example IV-2 of the present invention.
Figure 4:
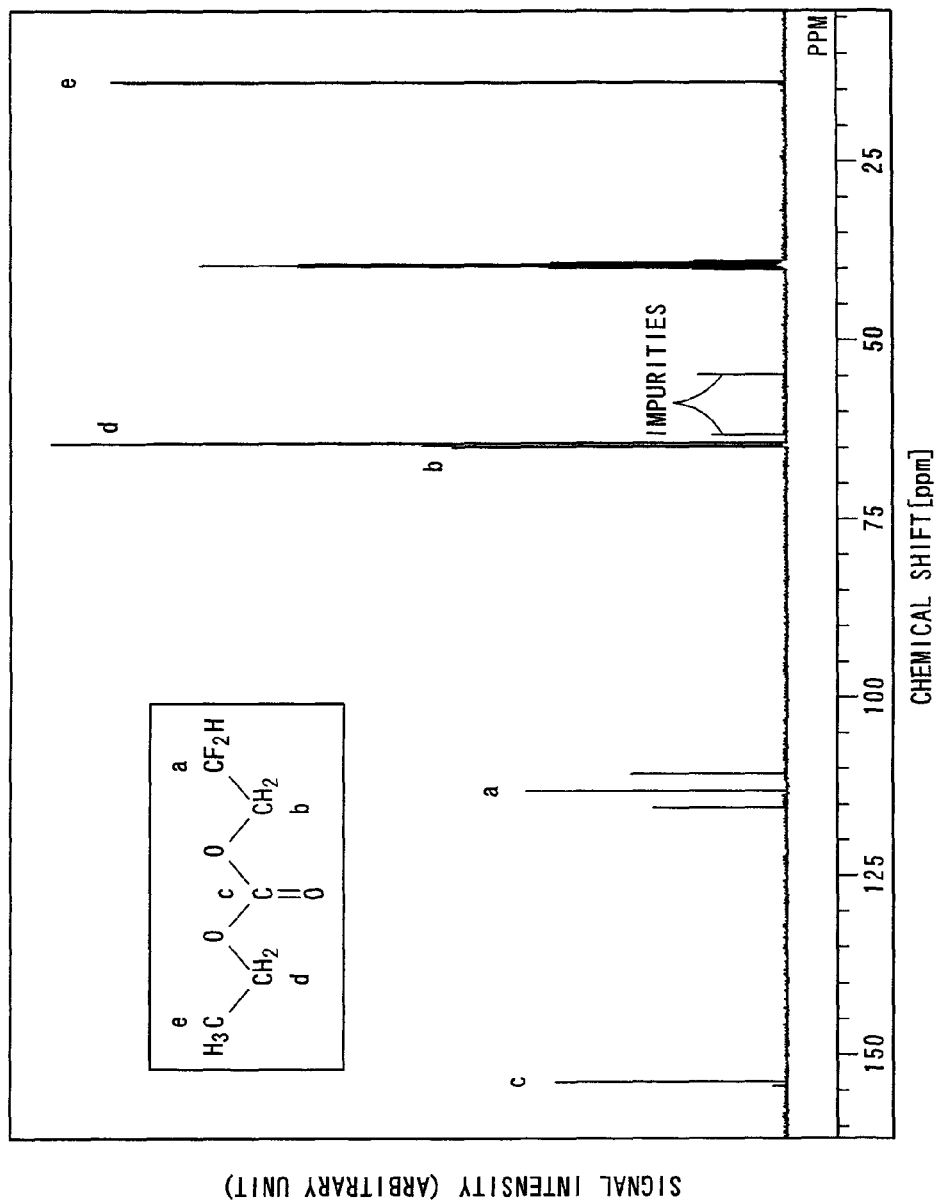
FIG. 4 shows a $^{13}$C NMR spectrum of a product prepared according to Example IV-2 of the present invention.

FIG. 3 shows the $^1$H NMR spectrum of the product (2,2-difluoroethyl ethyl carbonate) obtained in Example IV-2, and FIG. 4 shows the $^{13}$C NMR spectrum.

Example IV-3

Synthesis of 2,2-Difluoroethyl n-Propyl Carbonate 2,2-Difluoroethyl n-propyl carbonate was prepared as in [Synthesis of 2,2-Difluoroethyl Methyl Carbonate] of Example IV-1, except that propyl chlorocarbonate (7.4 g, 0.073 mol) was substituted for methyl chlorocarbonate (6.9 g, 0.073 mol).

The product 2,2-difluoroethyl n-propyl carbonate obtained was 5.4 g (yield: 53%). The structure of the compound obtained was determined by analysis of $^1$H, $^{13}$C, and $^{19}$F NMR spectra, and a mass spectrum (M/e=168).

Peak data in the measured $^1$H, $^{13}$C, and $^{19}$F NMR spectra is listed with the structure determined from the spectra. In the structural formula and the peak data, each of a, b, c, d, e, and f represents the notation for the carbon at the corresponding position in the following structural formula.

[Chemical Formula 13]

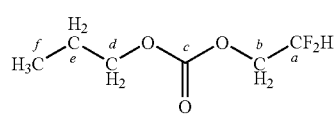

Figure 5:
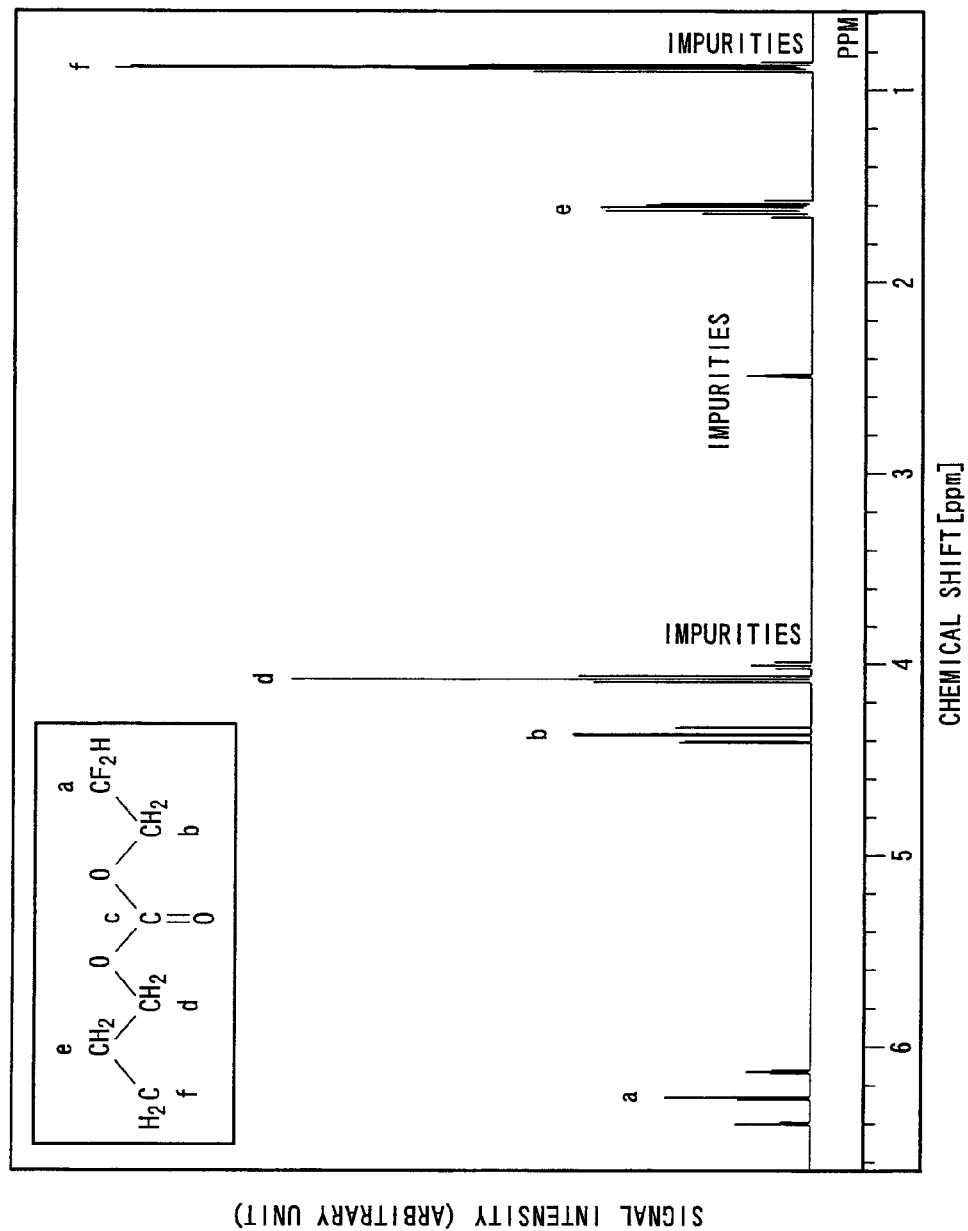
FIG. 5 shows a $^1$H NMR spectrum of a product prepared according to Example IV-3 of the present invention.
Figure 6:
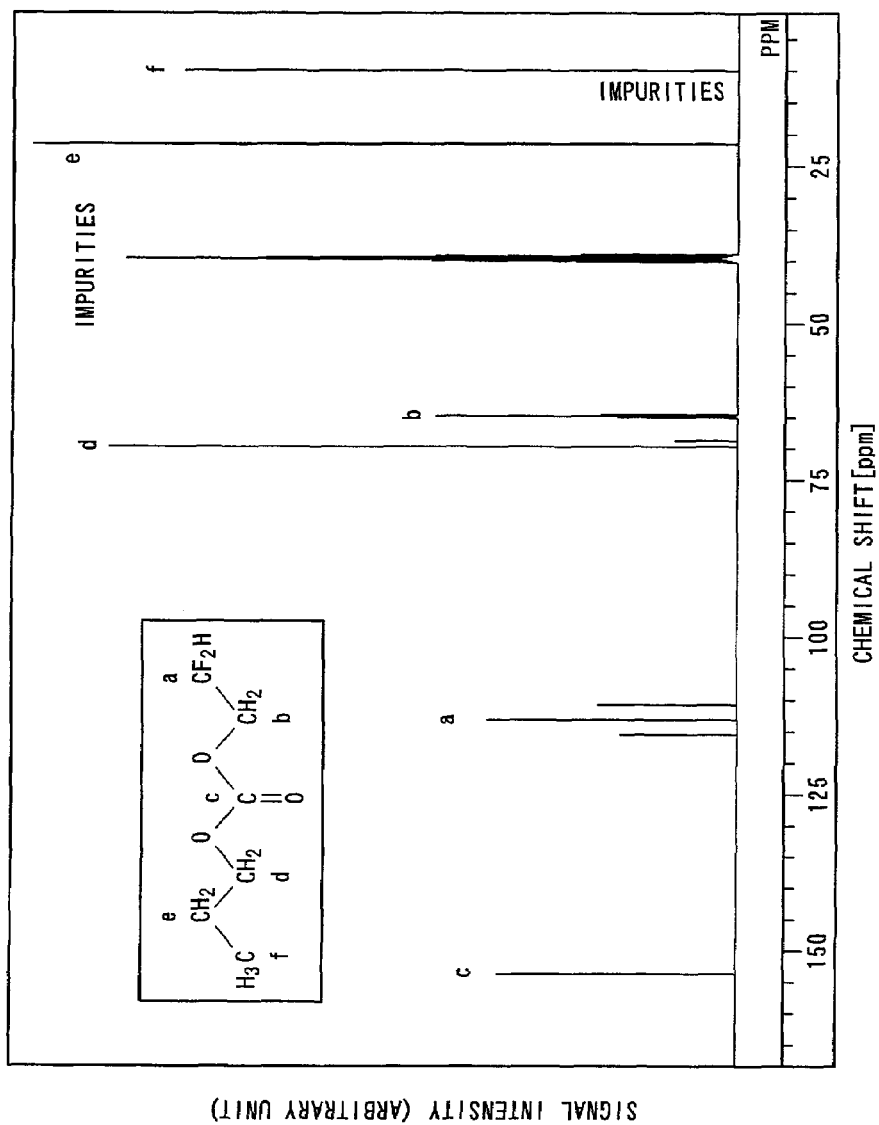
FIG. 6 shows a $^{13}$C NMR spectrum of a product prepared according to Example IV-3 of the present invention.

$^1$H NMR (DMSO-d6)
δ 0.89 t $J_{H-H}$=7 Hz (f)
δ 1.62 Sextet $J_{H-H}$=7 Hz (e)
δ 4.08 t $J_{H-H}$=7 Hz (d)
δ 4.37 t d $J_{H-F}$=15 Hz, $J_{H-H}$=3 Hz (b)
δ 6.27 t t $J_{H-F}$=54 Hz, $J_{H-H}$=3 Hz (a)
$^{13}$C NMR (DMSO-d6)
δ 9.93 s (f)
δ 21.43 s (e)
δ 69.66 t $J_{C-F}$=26 Hz (b)
δ 64.70 s (d)
δ 113.09 t $J_{C-F}$=238 Hz (a)
δ 153.87 s (c)
$^{19}$F NMR
δ −126.7 d t $J_{F-H}$=54 Hz, $J_{F-H}$=15 Hz FIG. 5 shows the $^1$H NMR spectrum of the product (2,2-difluoroethyl n-propyl carbonate) obtained in Example IV-3, and FIG. 6 shows the $^{13}$C NMR spectrum.

Example IV-4

Synthesis of n-Butyl-2,2-Difluoroethyl Carbonate n-Butyl-2,2-difluoroethyl carbonate was prepared as in [Synthesis of 2,2-Difluoroethyl Methyl Carbonate] of Example IV-1, except that butyl chlorocarbonate (10.0 g, 0.073 mol) was substituted for methyl chlorocarbonate (6.9 g, 0.073 mol).

The product n-butyl 2,2-difluoroethyl carbonate obtained was 5.9 g (yield: 54%). The structure of the compound obtained was determined by analysis of $^1$H, $^{13}$C, and $^{19}$F NMR spectra, and a mass spectrum (M/e=182).

Peak data in the measured $^1$H, $^{13}$C, and $^{19}$F NMR spectra is listed with the structure determined from the spectra. In the structural formula and the peak data, each of a, b, c, d, e, f, and g represents the notation for the carbon at the corresponding position in the following structural formula.

[Chemical Formula 14]

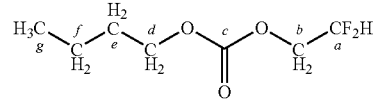

Figure 7:
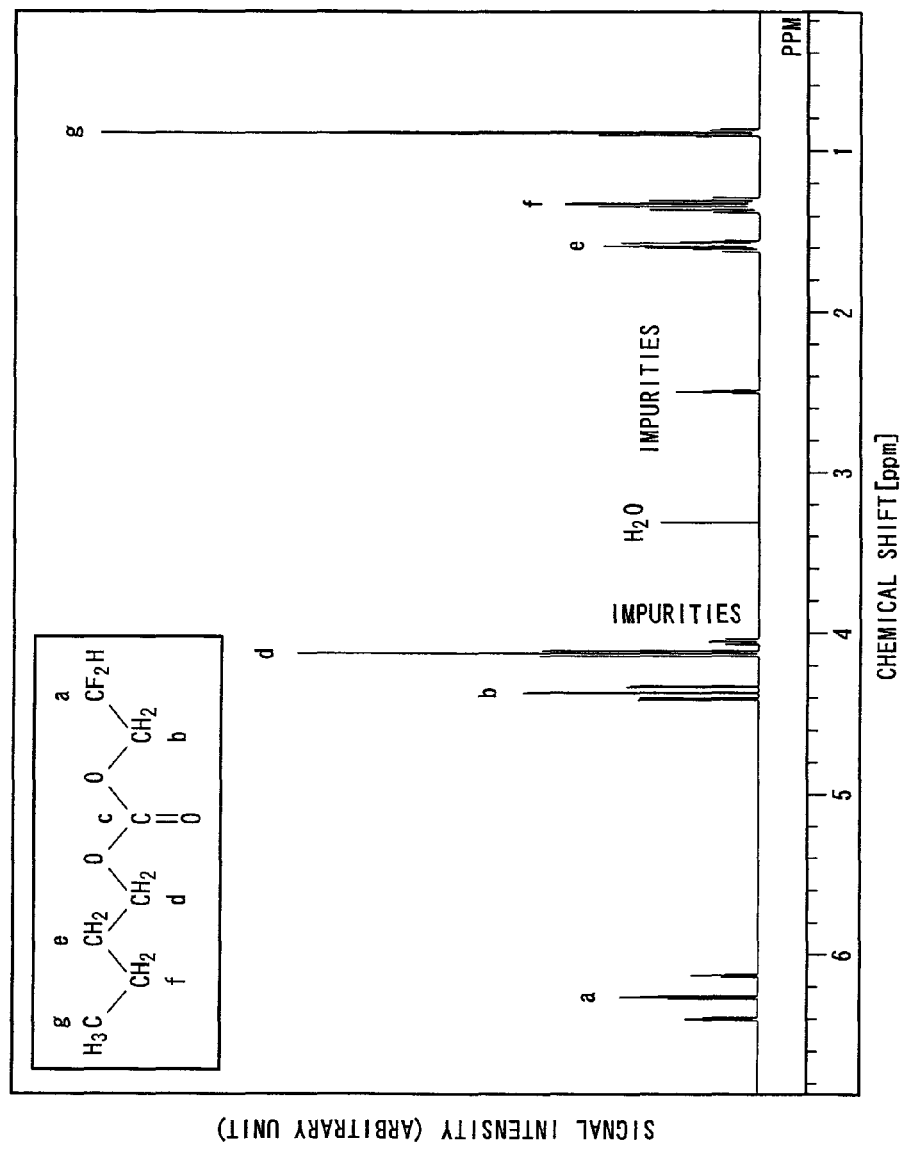
FIG. 7 shows a $^1$H NMR spectrum of a product prepared according to Example IV-4 of the present invention.
Figure 8:
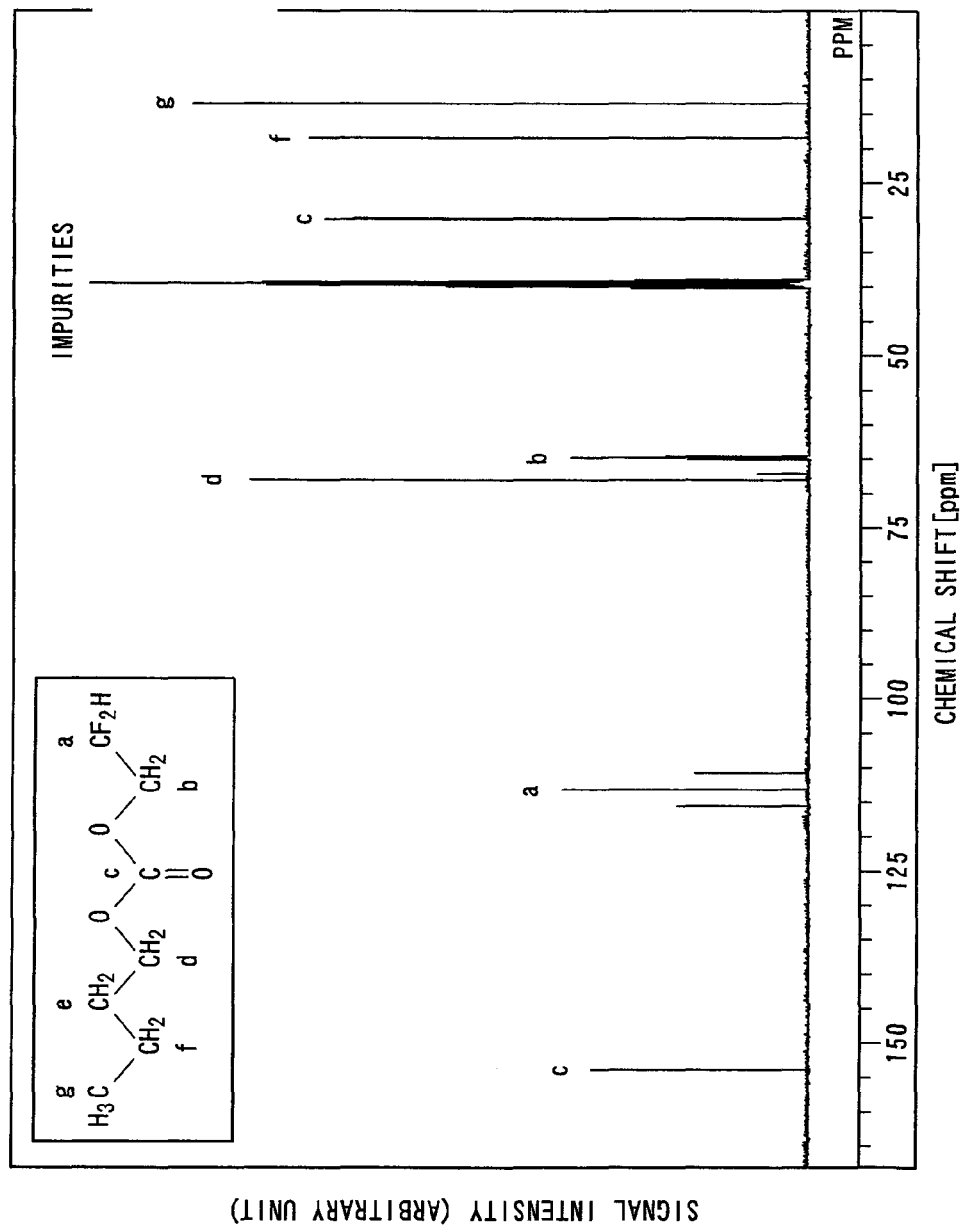
FIG. 8 shows a $^{13}$C NMR spectrum of a product prepared according to Example IV-4 of the present invention.

$^1$H NMR (DMSO-d6)
δ 0.90 t $J_{H-H}$=7 Hz (g)
δ 1.32 sextet $J_{H-H}$=7 Hz (f)
δ 1.58 quintet $J_{H-H}$=7 Hz (e)
δ 4.12 t $J_{H-H}$=7 Hz (d)
δ 4.37 t d $J_{H-F}$=15 Hz, $J_{H-H}$=3 Hz (b)
δ 6.26 t t $J_{H-F}$=54 Hz, $J_{H-H}$=3 Hz (a)
$^{13}$C NMR (DMSO-d6)
δ 13.44 s (g)
δ 18.36 s (f)
δ 30.03 s (e)
δ 64.71 t $J_{C-F}$=26 Hz (b)
δ 67.94 s (d)
δ 113.09 t $J_{C-F}$=238 Hz (a)
δ 153.86 s (c)
$^{19}$F NMR
δ −126.6 d t $J_{F-H}$=54 Hz, $J_{F-H}$=15 Hz FIG. 7 shows the $^1$H NMR spectrum of the product (n-butyl 2,2-difluoroethyl carbonate) obtained in Example IV-4, and FIG. 8 shows the $^{13}$C NMR spectrum.

Industrial Applicability

Any nonaqueous electrolytic solution and nonaqueous electrolyte secondary cell of the first, second, and third aspects of the present invention, which may be widely applied in any field of industry, is especially excellent in long-term charge-discharge cycle characteristics and therefore, is suitably used as power sources of notebook personal computers, pen-input personal computers, mobile computers, electronic book players, cellular phones, portable facsimiles, portable copiers, portable printers, headphone stereos, video movies, liquid crystal television sets, handy cleaners, portable CD players, mini disc players, transceivers, electronic notebooks, electronic calculators, memory cards, portable tape recorders, radios, backup power sources, motors, illuminators, toys, game machines, watches, stroboscopes, cameras, and load leveling of power and is also used in electric bicycles, electric scooters, and electric cars, for example.

The carbonate compounds of the present invention may be widely applied in any field of industry, and is suitably used as reaction solvents for organic synthesis, materials for polymer compounds, extraction solvents for various inorganic and organic substances, dilution solvents for paint and ink, materials and dilution solvents for pharmaceuticals and agricultural chemicals, and solvents and additives for electrolytic solutions for energy storage devices, for example.

Although the present invention has been described in detail with reference to particular embodiments thereof, it is apparent to those skilled in the art that various changes can be made thereto without departing from the spirit and scope of the present invention.

The present application is based on Japanese Patent Application (Patent Application No. 2005-170911) filed on Jun. 10, 2005, Japanese Patent Application (Patent Application No. 2005-170912) filed on Jun. 10, 2005, Japanese Patent Application (Patent Application No. 2005-170913) filed on Jun. 10, 2005, Japanese Patent Application (Patent Application No. 2005-170910) filed on Jun. 10, 2005, Japanese Patent Application (Patent Application No. 2005-190351) filed on Jun. 29, 2005, Japanese Patent Application (Patent Application No.

2006-161353) filed on Jun. 9, 2006, Japanese Patent Application (Patent Application No. 2006-161354) filed on Jun. 9, 2006, and Japanese Patent Application (Patent Application No. 2006-161355) filed on Jun. 9, 2006, which are herein incorporated in their entireties by reference.

The invention claimed is:

1. A nonaqueous electrolytic solution, comprising:
a linear carbonate of formula (1):

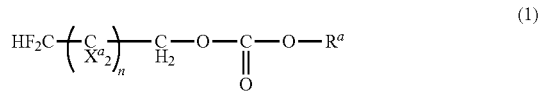

(1)

wherein
$X^a$ is hydrogen;
$R^a$ is an alkyl group selected from the group consisting of methyl, ethyl, n-propyl and n-butyl; and
n is an integer of 0 to 7.

2. The nonaqueous electrolytic solution according to claim 1, further comprising a carbonate having at least one of an unsaturated bond and a halogen atom, with the proviso that the linear carbonates are excluded.

3. The nonaqueous electrolytic solution according to claim 2, wherein a concentration of the carbonate having at least one of an unsaturated bond and a halogen atom in the nonaqueous electrolytic solution is 0.01% by weight to 70% by weight.

4. The nonaqueous electrolytic solution according to claim 2, wherein the carbonate having at least one of an unsaturated bond and a halogen atom is at least one carbonate selected from the group consisting of vinylene carbonate, vinyl ethylene carbonate, fluoroethylene carbonate, difluoroethylene carbonate, and derivatives thereof.

5. The nonaqueous electrolytic solution according to claim 1, further comprising ethylene carbonate, propylene carbonate or a mixture thereof.

6. The nonaqueous electrolytic solution according to claim 1, further comprising at least one selected from the group consisting of dimethyl carbonate, ethyl methyl carbonate, diethyl carbonate, methyl n-propyl carbonate, ethyl n-propyl carbonate, and di-n-propyl carbonate.

7. A nonaqueous electrolyte secondary cell, comprising:
a negative electrode;
a positive electrode; and
a nonaqueous electrolytic solution according to claim 1;
wherein the negative and positive electrodes occlude and discharge lithium ions.

8. The nonaqueous electrolyte secondary cell according to claim 7, wherein the nonaqueous electrolyte further comprises a carbonate having at least one of an unsaturated bond and a halogen atom, with the proviso that the linear carbonates are excluded.

9. The nonaqueous electrolytic secondary cell according to claim 8, wherein a concentration of the carbonate having at least one of an unsaturated bond and a halogen atom in the nonaqueous electrolytic solution is 0.01% by weight to 70% by weight.

10. The nonaqueous electrolytic secondary cell according to claim 8, wherein the carbonate having at least one of an unsaturated bond and a halogen atom is at least one carbonate selected from the group consisting of vinylene carbonate, vinyl ethylene carbonate, fluoroethylene carbonate, difluoroethylene carbonate, and derivatives thereof.

11. The nonaqueous electrolytic secondary cell according to claim 7, wherein the nonaqueous electrolyte further comprises ethylene carbonate, propylene carbonate or a mixture thereof.

12. The nonaqueous electrolytic secondary cell according to claim 7, wherein the nonaqueous electrolyte further comprises at least one selected from the group consisting of dimethyl carbonate, ethyl methyl carbonate, diethyl carbonate, methyl n-propyl carbonate, ethyl n-propyl carbonate, and di-n-propyl carbonate.

* * * * *